United States Patent
Nebel et al.

(10) Patent No.: US 6,204,221 B1
(45) Date of Patent: Mar. 20, 2001

(54) HERBICIDES

(75) Inventors: Kurt Nebel, Hochwald; Hans-Georg Brunner, Lausen; Rolf Schurter, Binningen, all of (CH)

(73) Assignee: Syngenta Crop Protection, Inc.

( * ) Notice: Subject to any disclaimer, the term of this patent is extended or adjusted under 35 U.S.C. 154(b) by 0 days.

(21) Appl. No.: 09/297,783

(22) PCT Filed: Nov. 10, 1997

(86) PCT No.: PCT/EP97/06243

§ 371 Date: May 7, 1999

§ 102(e) Date: May 7, 1999

(87) PCT Pub. No.: WO98/21199

PCT Pub. Date: May 22, 1998

(30) Foreign Application Priority Data

Nov. 12, 1996  (CH) .................................................... 2797/96

(51) Int. Cl.⁷ .......................... A01N 43/56; C07D 401/04
(52) U.S. Cl. .................... 504/253; 546/275.4; 546/276.1
(58) Field of Search ...................... 504/253; 546/275.4, 546/276.1

(56) References Cited

U.S. PATENT DOCUMENTS

| | | | |
|---|---|---|---|
| 4,526,895 | 7/1985 | Jarreau et al. | 514/341 |
| 5,032,165 | 7/1991 | Miura et al. | 544/69 |

FOREIGN PATENT DOCUMENTS

| | | |
|---|---|---|
| 195 30 606 | 2/1997 | (DE) . |
| 0 107 619 | 5/1984 | (EP) . |
| 0 284 030 | 9/1988 | (EP) . |
| 0 361 114 | 4/1990 | (EP) . |
| 8-193067 | 7/1996 | (JP) . |
| WO 92/02509 | 2/1992 | (WO) . |
| WO 92/06962 | 4/1992 | (WO) . |
| WO 93/07138 | 4/1993 | (WO) . |
| WO 94 29300 | 12/1994 | (WO) . |
| WO 95/33728 | 12/1995 | (WO) . |
| WO 96/01254 | 1/1996 | (WO) . |
| WO 97 11943 | 4/1997 | (WO) . |
| WO 97/13756 | 4/1997 | (WO) . |

OTHER PUBLICATIONS

Chemical Abstract 97–225868/20, May 29, 1996 (of WO 97/11943).
Derwent Abstract 97–146353/199714, 1997 (of DE 19530606).
Derwent Abstract 95–036368/199505, 1995 (of WO 94/29300).
Derwent Abstract 93–134355/16, Jul. 2, 1992 (of WO 93/07138).
Derwent Abstract 96–397231/40, Nov. 16, 1994 (of JP 08 193 067).

*Primary Examiner*—Jane Fan
(74) *Attorney, Agent, or Firm*—William A. Teoli, Jr.

(57) ABSTRACT

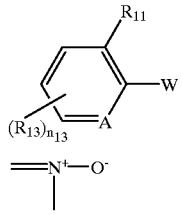

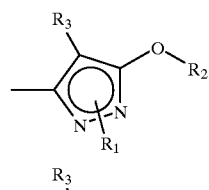

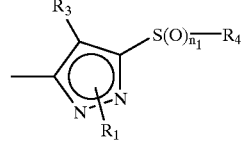

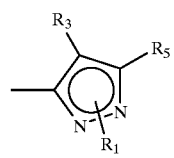

Compounds of formula (I) in which A is =N— or (a); W is a group (W1), (W2) or (W3); $R_{11}$ is hydrogen, fluorine, chlorine, bromine or methyl; and $R_1$ to $R_5$, $R_{13}$, $n_1$ and $n_{13}$ are as defined in claim 1, and the pyrazole N-oxydes, agrochemically tolerated salts and stereoisomers of these compounds of formula (I), have good pre- and post-emergent selective herbicidal properties. The preparation of these compounds and their use as herbicidal active substances are described.

14 Claims, No Drawings

HERBICIDES

This is a 371 of PCT/EP97/06243 Nov. 10, 1997, now WO98/21199.

The present invention relates to novel herbicidally active substituted pyrazole derivatives, a process for their preparation, compositions comprising these compounds and their use for controlling weeds, in particular in crops of useful plants, for example cereals, maize, rice, cotton, soya, oilseed rape, sorghum, sugarcane, sugarbeet, sunflowers, vegetables, plantations and fodder plants, or for inhibiting plant growth. Phenyl-pyrazole compounds having a herbicidal action are known and are described, for example, in EP-A-0 361 114, U.S. Pat. No. 5,032,165, WO 92/02509, WO 92106962, WO 95133728 and WO 96/01254. It has now been found, surprisingly, that substituted pyridyl-pyrazole derivatives have outstanding herbicidal and growth-inhibiting properties.

The present invention therefore relates to compounds of the formula I

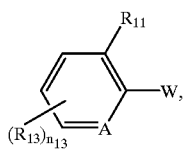

(I)

in which
A is =N— or

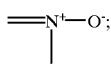

$n_{13}$ is 1, 2 or 3;

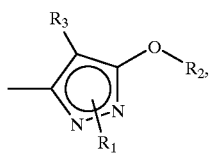

(W1)

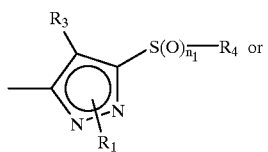

(W2)

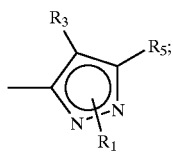

(W3)

$R_1$ is hydrogen, $C_1$–$C_4$alkyl, $C_1$–$C_4$halogenoalkyl, cyano-$C_1$–$C_4$alkyl, $C_3$- or $C_4$alkenyl, $C_3$- or $C_4$halogenoalkenyl, $C_3$- or $C_4$alkynyl or $C_3$–$C_6$cycloalkyl;

$R_2$ is hydrogen, $C_1$–$C_4$alkyl, $C_1$–$C_4$halogenoalkyl, $C_3$–$C_6$alkenyl, $C_3$–$C_6$halogenoalkenyl, $C_3$–$C_6$alkynyl, $C_1$–$C_4$alkylsulfonyl, $C_1$–$C_4$halogenoalkylsulfonyl, $C_2$–$C_4$alkenylsulfonyl or $C_2$–$C_4$halogenoalkenylsulfonyl;

$R_3$ is hydrogen, $C_1$–$C_4$alkyl, $C_1$–$C_4$halogenoalkyl, $C_1$–$C_4$hydroxyalkyl, $C_2$–$C_6$alkenyl, $C_2$–$C_6$-halogenoalkenyl, $C_2$–$C_6$alkynyl, halogen, cyano, $NH_2C(S)$—, nitro, OHC— or $R_{18}R_{19}N$—;

$R_{18}$ and $R_{19}$ independently of one another are hydrogen, $C_1$–$C_4$alkyl, $C_1$–$C_4$halogenoalkyl, $C_3$–$C_4$alkenyl, $C_3$–$C_4$halogenoalkenyl, $C_3$–$C_4$cycloalkyl, $C_3$–$C_6$alkynyl, $C_1$–$C_6$alkylcarbonyl, $C_1$–$C_6$halogenoalkylcarbonyl, $C_2$–$C_6$alkenylcarbonyl, $C_2$–$C_6$halogenoalkenylcarbonyl, $C_1$–$C_6$alkylsulfonyl or $C_1$–$C_6$halogenoalkylsulfonyl;

$n_1$ is 0, 1 or 2;

$R_4$ is hydrogen, $C_1$–$C_4$alkyl, $C_1$–$C_4$halogenoalkyl, $C_3$–$C_6$alkenyl, $C_3$–$C_4$halogenoalkenyl, $C_3$–$C_6$alkynyl or C36ecycloalkyl;

$R_5$ is hydrogen, halogen, $C_1$–$C_4$alkyl, $C_1$–$C_4$halogenoalkyl, cyano, nitro, amino, $NH_2C(S)$—, $C_1$–$C_4$alkylcarbonyl, $C_1$–$C_4$halogenoalkylcarbonyl, $C_2$–$C_4$alkenylcarbonyl, $C_2$–$C_4$halogenoalkenylcarbonyl or $C_2$–$C_4$alkynylcarbonyl;

$R_{11}$ is hydrogen, fluorine, chlorine, bromine or methyl;

$R_{13}$ is hydrogen, halogen, cyano, $ClS(O)_2$—, $ClC(O)$—, nitro, amino,

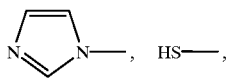, HS—, $R_{20}NH$— or $R_{20}R_{21}N$—;

$R_{20}$ and $R_{21}$ independently of one another are $C_1$–$C_8$alkyl, $C_3$–$C_8$alkenyl, $C_3$–$C_9$alkynyl, $C_3$–$C_6$cycloalkyl, $C_1$–$C_8$halogenoalkyl, $C_3$–$C_8$halogenoalkenyl, $C_1$–$C_4$alkylcarbonyl, $C_1$–$C_4$-halogenoalkylcarbonyl, $C_1$–$C_4$alkylsuffonyl, $C_1$–$C_4$halogenalkylsulfonyl, benzyl or benzyl which is substituted on the phenyl ring once to three times by halogen, $C_1$–$C_4$alkyl or $C_1$–$C_4$halogenoalkyl; or $R_{13}$ is $R_{30}O$—;

$R_{30}$ is hydrogen, $C_1$–$C_8$alkyl, $C_3$–$C_8$alkenyl, $C_3$–$C_8$alkynyl, $C_3$–$C_6$cycloalkyl, $C_1$–$C_8$halogenoalkyl, $C_3$–$C_8$halogenoalkenyl, $C_1$–$C_4$alkoxy-$C_1$–$C_4$alkyl, $C_3$–$C_6$alkenyloxy-$C_1$–$C_4$alkyl, $C_3$–$C_6$lkynyloxy-$C_1$–$C_4$alkyl, $C_1$–$C_4$alkoxy-$C_1$–$C_4$alkoxy-$C_1$–$C_4$alkyl, $C_1$–$C_4$alkylthio-$C_1$–$C_4$alkyl, $C_1$–$C_8$alkoxycarbonyl, $C_3$–$C_8$alkenyloxycarbonyl, benzyloxycarbonyl, phenyl, benzyl, pyridyl, pyrimidinyl, pyrazinyl or pyridazinyl, where these aromatic and heteroaromatic rings mentioned can be unsubstituted or substituted once to three times by halogen, $C_1$–$C_4$alkyl or $C_1$–$C_4$halogenoalkyl; or $R_{30}$ is $R_{31}X_1C(O)$—$C_1$–$C_9$alkyl- or

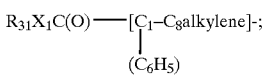

$X_1$ is oxygen, sulfur or

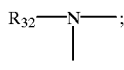

$R_3$, is hydrogen, $C_1$–$C_8$alkyl, $C_3$–$C_8$alkenyl, $C_3$–$C_8$alkynyl, $C_3$–$C_6$cycloalkyl, $C_1$–$C_8$-halogenoalkyl, $C_3$–$C_8$halogenoalkenyl, $C_1$–$C_4$alkoxy-$C_1$–$C_4$alkyl, $C_3$–$C_6$alkenyloxy-$C_1$–$C_4$alkyl, $C_1$–$C_4$alkyl-thio-$C_1$–$C_4$alkyl, phenyl, phenyl which is substituted once to three times by halogen, $C_1$–$C_4$alkyl or $C_1$–$C_4$halogenoalkyl, benzyl or benzyl which is substituted once to three times on the phenyl ring by halogen, $C_1$–$C_4$alkyl or $C_1$–$C_4$halogenoalkyl;

$R_{32}$ is hydrogen, $C_1$–$C_8$alkyl, $C_3$–$G_8$alkenyl, $C_3$–$C_8$alkynyl, $C_3$–$C_6$cycloalkyl or $C_1$–$C_8$-halogenoalkyl; or $R_{13}$ is $R_{33}S(O)_{n2}$—;

$n_2$ is 0, 1 or 2;

$R_{33}$ is $C_1$–$C_8$alkyl, $C_3$–$C_8$alkenyl, $C_3$–$C_8$alkynyl, $C_3$–$C_6$cycloalkyl, $C_1$–$C_8$halogenoalkyl, $C_3$–$C_8$halogenoalkenyl, $C_1$–$C_4$alkoxy-$C_1$–$C_4$alkyl, $C_3$–$C_6$alkenyloxy-$C_1$–$C_4$alkyl, $C_1$–$C_4$alkylthio-$C_1$–$C_4$alkyl, phenyl, phenyl which is substituted once to three times by halogen, $C_1$–$C_4$alkyl or $C_1$–$C_4$halogenoalkyl, benzyl or benzyl which is substituted once to three times on the phenyl ring by halogen, $C_1$–$C_4$alkyl or $C_1$–$C_4$halogenoalkyl, and, if $n_2$ is 0, R33 is hydrogen, $C_1$–$C_8$alkylcarbonyl or $R_{34}X_2C(O)$—;

$X_2$ is oxygen, sulfur or

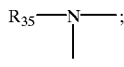

$R_{34}$ is hydrogen, $C_1$–$C_8$alkyl, $C_3$–$C_8$alkenyl, $C_3$–$C_8$alkynyl, $C_3$–$C_6$cycloalkyl, $C_1$–$C_8$-halogenoalkyl, $C_3$–$C_8$halogenoalkenyl, $C_1$–$C_4$alkoxy-$C_1$–$C_4$alkyl, $C_3$–$C_6$alkenyloxy-$C_1$–$C_4$alkyl, $C_1$–$C_4$alkyl-thio-$C_1$–$C_4$alkyl, phenyl, phenyl which is substituted once to three times by halogen, $C_1$–$C_4$alkyl or $C_1$–$C_4$halogenoalkyl, benzyl or benzyl which is substituted once to three times on the phenyl ring by halogen, $C_1$–$C_4$alkyl or $C_1$–$C_4$halogenoalkyl;

$R_{35}$ is hydrogen, $C_1$–$C_8$alkyl or $C_3$–$C_8$alkenyl; or $R_{13}$ is $R_{36}R_{37}NS(O)_2$—;

$R_{36}$ is hydrogen, $C_1$–$C_8$alkyl, $C_2$–$C_8$alkenyl, $C_3$–$C_8$alkynyl or $C_3$–$C_8$cycloalkyl;

$R_{37}$ is hydrogen, $C_1$–$C_8$alkyl, $C_3$–$C_8$alkenyl, $C_3$–$C_8$alkynyl, $C_1$–$C_8$halogenoalkyl, $C_1$–$C_4$-alkylcarbonyl, $C_1$–$C_4$halogenoalkylcarbonyl, benzoyl or benzoyl which is substituted once to three times on the phenyl ring by halogen, $C_1$–$C_4$alkyl or $C_1$–$C_4$halogenoalkyl;

$R_{13}$ is $R_{40}C(O)$—;

$R_{40}$ is hydrogen, fluorine, chlorine, $C_1$–$C_8$alkyl, $C_2$–$C_8$alkenyl, $C_2$–$C_8$alkynyl, $C_3$–$C_6$cycloalkyl, $C_1$–$C_8$halogenoalkyl, cyano-$C_1$–$C_4$alkyl, $C_2$—$C_8$alogenoalkenyl, $C_1$–$C_4$alkoxy-$C_1$–$C_4$alkyl, $C_3$–$C_6$alkenyloxy-$C_1$–$C_4$alkyl, $C_1$–$C_4$alkylthio-$C_1$–$C_4$alkyl, phenyl, phenyl which is substituted once to three times by halogen, $C_1$–$C_4$alkyl or $C_1$–$C_4$halogenoalkyl, benzyl or benzyl which is substituted once to three times on the phenyl ring by halogen, $C_1$–$C_4$alkyl or $C_1$–$C_4$halogenoalkyl; or $R_{13}$ is $R_{50}X_3C(O)$—;

$X_3$ is oxygen, sulfur,

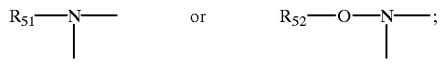

$R_{50}$ is hydrogen, $C_1$–$C_8$alkyl, $C_3$–$C_8$alkenyl, $C_3$–$C_8$alkynyl, $C_3$–$C_6$cycloalkyl, $C_1$–$C_8$-halogenoalkyl, $C_3$–$C_8$halogenoalkenyl, cyano-$C_1$–$C_4$alkyl, $C_1$–$C_4$alkoxy-$C_1$–$C_4$alkyl, $C_3$–$C_6$alkenyloxy-$C_1$–$C_4$alkyl, (oxiranyl)—$CH_2$—, oxetanyl-, $C_1$–$C_4$alkylthio-$C_1$–$C_4$alkyl, phenyl, phenyl which is substituted once to three times by halogen, $C_1$–$C_4$alkyl or $C_1$–$C_4$halogenoalkyl, benzyl or benzyl which is substituted once to three times on the phenyl ring by halogen, $C_1$–$C_4$alkyl or $C_1$–$C_4$halogenoalkyl, phenyl-$C_2$–$C_6$alkyl, $C_1$–$C_6$alkyl-CO—$C_1$–$C_4$alkyl,

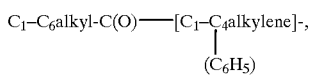

$R_{53}X_4C(O)$—$C_1$–$C_6$alkyl,

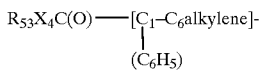

or $R_{53}X_4C(O)$—$C_3$–$C_6$cycloalkyl;

$X_4$ oxygen, sulfur,

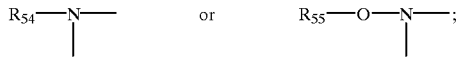

$R_{53}$ is hydrogen, $C_1$–$C_8$alkyl, $C_3$–$C_8$alkenyl, $C_3$–$C_8$alkynyl, $C_3$–$C_6$cycloalkyl, $C_1$–$C_8$-halogenoalkyl, $C_3$–$C_8$halogenoalkenyl, cyano-$C_1$–$C_4$alkyl, $C_1$–$C_4$alkoxy-$C_1$–$C_4$alkyl, $C_3$–$C_6$-alkenyloxy-$C_1$–$C_4$alkyl, (oxiranyl)—$CH_2$—, oxetanyl-, $C_1$–$C_4$alkylthio-$C_1$–$C_4$alkyl, phenyl, phenyl which is substituted once to three times by halogen, $C_1$–$C_4$alkyl or $C_1$–$C_4$halogenoalkyl, benzyl, benzyl which is substituted once to three times on the phenyl ring by halogen, $C_1$–$C_4$alkyl or $C_1$–$C_4$halogenoalkyl, or phenyl-$C_2$–$C_6$alkyl;

$R_{51}$, $R_{52}$, $R_{54}$ and $R_{55}$ independently of one another are hydrogen, $C_1$–$C_8$alkyl, $C_3$–$C_8$alkenyl, $C_3$–$C_8$alkynyl, $C_1$–$C_8$halogenoalkyl or benzyl; or $R_{13}$ is $B_1$-$C_1$–$C_8$alkyl, $B_1$-$C_2$–$C_8$alkenyl, $B_1$-$C_2$–$C_8$alkynyl, $B_1$-$C_1$–Calogenoalkyl, $B_1$-$C_2$–$C_8$halogenoalkenyl, $B_1$-$C_1$–$C_4$alkoxy-$C_1$–$C_4$alkyl, $B_1$-$C_1$–$C_4$alkylthio-$C_1$–$C_4$alkyl or $B_1$-$C_3$–$C_6$cycloalkyl;

$B_1$ is hydrogen, cyano, hydroxyl, $C_1$–$C_4$alkoxy, $C_3$–$C_8$alkenyloxy, $R_{60}X_5C(O)$—, $C_1$–$C_4$-alkylcarbonyl or $C_1$–$C_4$halogenoalkylcarbonyl;

$X_5$ has the meaning of $X_4$;

$R_{60}$ has the meaning of $R_{53}$; or $R_{13}$ is $B_2$-$C(R_{70})$=CH—;

$B_2$ is nitro, cyano or $R_{71}X_6C(O)$—;

$R_{70}$ is cyano or $R_{72}X_7C(O)$—;

$X_6$ and $X_7$ have the meaning of $X_4$; and $R_{71}$ and $R_{72}$ have the meaning of $R_{53}$, and the pyrazole N-oxides, agrochemicaiy tolerated salts and stereoisomers of these compounds of the formula I, the compounds of the formulae $I_{01}$, $I_{02}$, $I_{03}$ and $I_{04}$ being excluded:

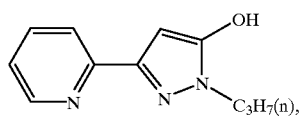

(I$_{01}$)

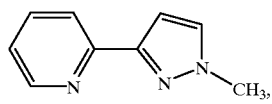

(I$_{02}$)

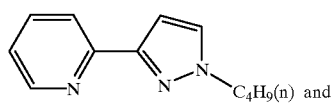

(I$_{03}$)

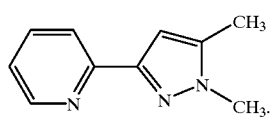

(I$_{04}$)

In the abovementioned definitions, halogen is to be understood as meaning iodine and, preferably, fluorine, chlorine and bromine.

The alkyl, alkenyl and alkynyl groups occurring in the substituent definitions can be straight-chain or branched, this also applying to the alkyl, alkenyl and alkynyl moiety of the alkylcarbonyl, alkylcarbamoyl, hydroxyalkyl, cyanoalkyl, alkoxyalkyl, alkoxyalkoxyalkyl, alkylthio, alkylthioalkyl, alkylthio-C(O), alkenylcarbamoyl, alkenylthio-C(O), alkynylthio-C(O), alkylsuffonyl, alkylaminocarbonyl, dialkylaminocarbonyl, alkylcarbonylalkyl, Bialkyl, Bialkenyl, Bialkynyl, HOC(O)alkyl, phenylalkyl, $R_{53}X_4C(O)$—$C_1$–$C_6$alkyl and $RaOX_5C(O)$—$C_1$–$C_8$-alkyl groups.

Alkyl groups are, for example, methyl, ethyl, n-propyl, isopropyl, n-butyl, sec-butyl, iso-butyl, tert-butyl and the various isomeric pentyl, hexyl, heptyl and octyl radicals. Methyl, ethyl, n-propyl, iso-propyl and n-butyl are preferred.

Examples of alkenyls are vinyl, allyl, methallyl, 1-methylvinyl, but-2-en-1-yl, pentenyl, 2-hexenyl, 3-heptenyl and 4-octenyl, preferably alkenyl radicals having a chain length of 3 to 5 carbon atoms.

Examples of alkynyls are ethynyl, propargyl, 1-methylpropargyl, 3-butynyl, but-2-yn-1-yl, 2-methylbutyn-2-yl, but-3-yn-2-yl, 1-pentynyl, pent-4-yn-1-yl or 2-hexynyl, preferably alkynyl radicals having a chain length of 2 to 4 carbon atoms.

Halogenoalkyl can be alkyl groups which are substituted once or several times, in particular once to three times, by halogen, halogen being iodine and, in particular, fluorine, chlorine and bromine, for example fluoromethyl, difluoromethyl, trifluoromethyl, chloromethyl, dichloromethyl, trichloromethyl, 2-fluoroethyl, 2,2-difluoroethyl, 2-chloroethyl, 2,2-dichloroethyl, 2,2,2-trifluoroethyl and 2,2,2-trichloroethyl.

Halogenoalkenyl can be alkenyl groups which are substituted once or several times by halogen, halogen being specifically bromine, iodine and, in particular, fluorine and chlorine, for example 2- and 3-fluoropropenyl, 2- and 3-chloropropenyl, 2- and 3-bromopropenyl, 2,3,3-trifluoropropenyl, 2,3,3-trichloropropenyl, 4,4,4-trifluoro-but-2-en-1-yl and 4,4,4-trichloro-but-2-en-1-yl. Of the alkenyl radicals substituted once, twice or three times by halogen, those which have a chain length of 3 or 4 carbon atoms are preferred. The alkenyl groups can be substituted by halogen on saturated or unsaturated carbon atoms.

Alkylsulfonyl is, for example, methylsulfonyl ethylsulfonyl, propylsulfonyl, iso-propylsulfonyl, n-butylsulfonyl, iso-butylsulfonyl, sec-butylsulfonyl and tert-butylsulfonyl; preferably methylsulfonyl and ethylsulfonyl.

Halogenoalkylsulfonyl is, for example, fluoromethylsulfonyl, difluoromethylsulfonyl, trifluoromethylsuffonyl, chloromethylsulfonyl, trichloromethylsulfonyl, 2-fluoroethylsulfonyl, 2,2,2-trifluoroethylsulfonyl and 2,2,2-trichloroethylsulfonyl.

Alkenylsulfonyl is, for example, allylsulfonyl, methallylsulfonyl, but-2-en-1-yl-sulfonyl, pentenyisulfonyl and 2-hexenyisulfonyl.

Halogenoalkenylsulfonyl is, for example, 2- and 3-fluoropropenyl-sulfonyl, 2- and 3-chloropropenyl-sulfonyl, 2- and 3-bromopropenyl-sulfonyl, 2,3,34rifluoropropenyl-sulfonyl, 2,3,3-trichloropropenyl-sulfonyl, 4,4,4-trifluoro-but-2-en-1-yl-sulfonyl and 4,4,4-trichloro-but-2-en-1-yl-sulfonyl.

Cyanoalkyl is, for example, cyanomethyl, cyanoethyl, cyanoeth-1-yl and cyanopropyl. Hydroxyalkyl is, for example, hydroxymethyl, 2-hydroxyethyl and 3-hydroxypropyl.

Alkylamino is, for example, methylamino, ethylamino and the isomeric propyl- and butylamino.

Dialkylamino is, for example, dimethylamino, diethylamino and the isomeric dipropyl- and dibutylamino.

Alkenylamino is, for example, allylamino, methallylamino and but-2-en-1-ylamino.

Alkynylamino is, for example, propargylamino and 1-methylpropargylamino.

Halogenoalkylamino is, for example, chloroethylamino, trifluoroethylamino and 3-chloropropylamino.

Di(halogenoalkyl)amino is, for example di(2-chloroethyl)amino.

Alkylcarbonyl is, in particular, acetyl and propionyl.

Halogenoalkylcarbonyl is, in particular, trifluoroacetyl, trichloroacetyl, 3,3,3-trifluoropropionyl and 3,3,3-trichloropropionyl.

Alkenylcarbonyl is, in particular, vinylcarbonyl, allylcarbonyl, methallylcarbonyl, but-2-en-1-yl-carbonyl, pentenylcarbonyl and 2-hexenylcarbonyl.

Alkynylcarbonyl is, in particular, acetylenecarbonyl, propargylcarbonyl, 1-methylpropargyl- carbonyl, 3-butynylcarbonyl, but-2-yn-1-yl-carbonyl and pent-4-yn-1-yl-carbonyl.

Alkenyloxy is, for example, allyloxy, methallyloxy and but-2-en-1-yloxy.

Alkynyloxy is, for example, propargyloxy and 1-methylpropargyloxy.

Alkoxy-alkyl is, for example, methoxymethyl, methoxyethyl, ethoxymethyl, ethoxyethyl, n-propoxymethyl, n-propoxyethyl, iso-propoxymethyl and iso-propoxyethyl.

Alkenyloxy-alkyl is, for example, aliyloxy-alkyl, methallyloxy-alkyl and but-2-en-1-yloxy-alkyl. Alkynyloxy-alkyl is, for example, propargyloxy-alkyl and 1-methylpropargyloxy-alkyl.

Alkoxycarbonyl is, for example, methoxycarbonyl, ethoxycarbonyl, n-propoxycarbonyl, iso-propoxycarbonyl and n-butoxycarbonyl, preferably methoxycarbonyl and ethoxycarbonyl.

Alkenyloxycarbonyl is, for example, allyloxycarbonyl, methallyloxycarbonyl, but-2-en-1-yl-oxycarbonyl, pentenyloxycarbonyl and 2-hexenyloxycarbonyl.

Alkynyloxycarbonyl is, for example, propargyloxycarbonyl, 3-butynyloxycarbonyl, but-2-yn-1-yl-oxycarbonyl and 2-methylbutyn-2-yl-oxycarbonyl.

Alkoxyalkoxycarbonyl is, for example, methoxymethoxycarbonyl, ethoxymethoxycarbonyl, ethoxyethoxycarbonyl, propoxymethoxycarbonyl, propoxyethoxycarbonyl, propoxypropoxycarbonyl and butoxyethoxycarbonyl.

Halogenoalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy.

The cycloalkyl radicals which are suitable substituents are, for example, cyclopropyl, cyclobutyl, cyclopentyl and cyclohexyl.

The cycloalkoxycarbonyl radicals which are suitable substituents are, for example, cyclopropoxycarbonyl, cyclobutoxycarbonyl, cyclopentoxycarbonyl and cyclohexyloxycarbonyl.

Alkylthio is, for example, methylthio, ethylthio, propylthio and butylthio and branched isomers thereof.

Alkylthioalkyl is, for example, methylthioethyl, ethylthioethyl, methylthiopropyl and ethyfthiopropyl.

Halogenoalkylthio-carbonyl is, for example, fluoromethylthio-carbonyl, difluoromethylthio-carbonyl, trffluoromethylthio-carbonyl, 2,2,2-trifluoroethylthio-carbonyl, 1,1,2,2-tetrafluoroethylthio-carbonyl, 2-fluoroethylthio-carbonyl, 2-chloroethylthiocarbonyl and 2,2,2-trichloroethylthio-carbonyl.

Phenyl, benzyl or benzoyl as part of a substituent, for example phenoxy, phenylthio, benzyloxy, benzylthio, phenoxycarbonyl, benzyloxycarbonyl, phenoxycarbonylalkyl, benzyloxycarbonylalkyl or benzylamino, are present in substituted or unsubstituted form. The substituents can then be in the ortho-, meta- or para-position. Substituents, are, for example, $C_1$–$C_4$alkyl, halogen or $C_1$–$C_4$halogenoalkyl.

Corresponding definitions can also be assigned to the substituents in composite definitions, for example halogenoalkenylcarbonyl, alkenyloxy-alkoxy, alkynyloxy-alkoxy, alkoxy-alkoxy-alkoxy, alkylthio-alkylamino, alkylthio-alkylthio, alkoxy-alkylthio, alkenyloxy-alkythio, alkenyloxy-alkylamino, $R_{30}O$—, $R_{40}C(O)$—, $R_{33}S(O)_{n2}$—, $R_{34}X_2C(O)$—, $R_{60}X_3C(O)$—, $R_{31}X_1C(O)$alkyl, $R_{53}X_4C(O)$cycloalkyl, $R_{36}R_{37}NS(O)_2$—, $B_1$alkyl, $B_1$alkenyl, $B_1$alkynyl, $B_1$halogenoalkyl, $B_1$halogenoalkenyl, $B_1$alkoxyalkyl, $B_1$alkylthioalkyl, $B_1$cycloalkyl and $E_2$—C($R_{70}$)=CH—.

In the definition of $R_{30}$, the group

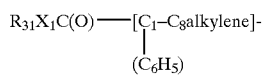

means that the $R_{31}X_1C(O)$—substituted $C_1$–$C_8$glkylene chain is additionally substituted by phenyl on one of the 8 carbon atoms, where the phenyl ring can be substituted once to three times by halogen, $C_1$–$C_4$alkyl or $C_1$–$C_4$halogenoalkyl and the alkylene chain can be straight-chain or branched and can be, for example, methylene, ethylene, methylethylene, propylene, 1-methyl-propylene and butylene.

In the definition of $R_{50}$, the groups

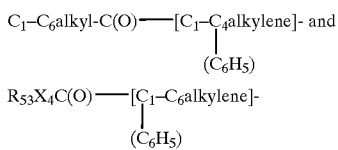

mean that the $C_1$–$C_6$alkyl-C(O)— or $R_{53}X_4C(O)$-substituted $C_1$–$C_4$or $C_1$–$C_6$alkylene chain is additionally substituted by phenyl ($C_6H_5$) on one of the 4 or, respectively, 6 carbon atoms, where the phenyl ring can be substituted once to three times by halogen, $C_1$–$C_4$alkyl or $C_1$–$C_4$halogenoalkyl and the alkylene chain can be straight-chain or branched and can be, for example, methylene, ethylene, methylethylene, propylene, 1-methyl-propylene and butylene.

In the definitions for cyanoalkyl, alkylcarbonyl, alkenylcarbonyl, halogenoalkenyl-carbonyl, alkynylcarbonyl, alkoxycarbonyl and halogenoalkylcarbonyl, the cyano or, respectively, carbonyl carbon atom is not included in the respective lower and upper carbon number limits stated.

In respect of the group W (W1 to W3), the compounds of the formula I are in general present as mixtures comprising the isomers substituted by the pyridyl group (pyrid) in the 3- and 5-position of the pyrazole ring, for example as isomers IW1a and IW1b

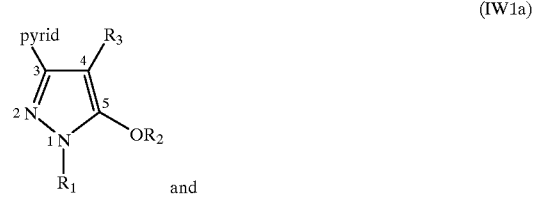

(IW1a)

and

(IW1b)

for the group W1. The isomer ratio can vary according to the synthesis process.

The invention also relates to the salts which the compounds of the formula I with acid hydrogen, in particular the derivatives with carboxylic acid and sulfonamide groups (for example carboxyl-substituted alkyl, alkylene, alkenyl, alkynyl, alkoxyalkyl, alkylfthioalkyl and cycloalkyl groups and $NH_2SO_2$—, alkylS(O)$_2$NH— and halogenoalkylS(O)$_2$NH-substituted pyridyl groups ($R_{13}$)), can form with bases. These salts are, for example, alkali metal salts, for example sodium and potassium salts; alkaline earth metal salts, for example calcium and magnesium salts; ammonium salts, i.e. unsubstituted ammonium salts and mono- or polysubstituted ammonium salts, for example triethylammonium and methylammonium salts; or salts with other organic bases.

Preferred alkali metal and alkaline earth metal hydroxides as salt-forming agents are, for example, the hydroxides of lithium, sodium, potassium, magnesium or calcium, and in particular those of sodium and potassium.

Examples of amines which are suitable for ammonium salt formation include ammonia and primary, secondary and tertiary $C_1$–$C_{18}$alkylamines, $C_1$–$C_4$hydroxyalkylamines and $C_2$–$C_4$-alkoxyalkylamines, for example methylamine, ethylamine, n-propylamine, iso-propylamine, the four isomeric butylamines, n-amylamine, iso-amylamine, hexylamine, heptylamine, octylamine, nonylamine, decylamine, pentadecylamine, hexadecylamine, heptadecylamine, octadecylamine, methyl-ethylamine, methyl-iso-propylamine, methyl-hexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, di-iso-propylamine, di-n-butylamine, di-n-amylamine, di-iso-amylamine, dihexylamine, diheptylamine, dioctylamine, ethanolamine, n-propanolamine, iso-propanolamine, N,N-diethanolamine, N-ethylpropanolamine, N-butylethanolamine, allylamine, n-butenyl-2-amine, n-pentenyl-2-amine, 2,3-dimethylbutenyl-2-amine, di-butenyl-2-amine, n-hexenyl-2-amine, propylenediamine, trimethylamine, triethylamine, tri-n-propylamine, tri-iso-propylamine, tri-n-butylamine, tri-iso-butylamine, tri-sec-butylamine, tri-n-amylamine, methoxyethylamine and ethoxyethylamine; heterocyclic amines, for example pyridine, quinoline, iso-quinoline, morpholine, thiomorpholine, piperidine, pyrrolidine, indoline, quinuclidine and azepine; and primary arylamines, for example, anilines, methoxyanilines, ethoxyanilines, o-, m- and p-toluidines, phenylenediamines, benzidines, naphthylamines and o-, m- and p-chloroanilines; and in particular triethylamine, iso-propylamine and di-iso-propylamine.

The salts of the compounds of the formula I with basic groups, in particular with basic pyridyl, pyrimidinyl, pyrazinyl, pyridazinyl and pyrazolyl rings, or of the derivatives with amino groups, for example alkylamino and dialkylamino groups, in the definition of $R_3$, $R_5$ and $R_{13}$ are, for example, salts with inorganic and organic acids, for example hydrogen halide acids, such as hydrofluoric acid, hydrochloric acid, hydrobromic acid or hydroiodic acid, and sulfuric acid, phosphoric acid and nitric acid, and organic acids, such as acetic acid, trifluoroacetic acid, trichloroacetic acid, proprionic acid, glycolic acid, thiocyanic acid, citric acid, benzoic acid, oxalic acid, formic acid, benzenesulfonic acid, p-toluenesulfonic acid and methanesuffonic acid.

The possible presence of at least one asymmetric carbon atom in the compounds of the formula I, for example in the substituent $R_{13}=OR_{30}$, in which $R_{30}$ is a branched alkyl, alkenyl, halogenoalkyl or alkoxyalkyl group, or $R_{13}=S(O)_{n_2}R_{33}$, in which, for example, $n_2=1$ and/or $R_{33}$ is a branched alkyl, alkenyl, halogenoalkyl or alkoxyalkyl group, means that the compounds can occur both in optically active individual isomers and in the form of racemic mixtures. In the present invention, the active compounds of the formula I are to be understood as meaning both the pure optical antipodes and the racemates or diastereomers.

If an aliphatic C=C double bond is present, geometric isomerism can occur. The present invention also relates to these isomers.

Preferred compounds of the formula I are those in which $R_3$ is hydrogen, $C_1$–$C_4$alkyl, $C_1$–$C_4$halogenoalkyl, $C_2$–$C_6$alkenyl, $C_2$–$C_6$alogenoalkenyl, $C_2$–$C_6$alkynyl, halogen, cyano, $NH_2C(S)$—, nitro or $R_{18}R_{19}N$—.

Preferred compounds of the formula I have the formula Ia

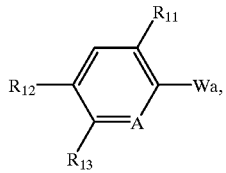

(Ia)

in which
Wa is a group

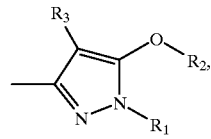

(W1a)

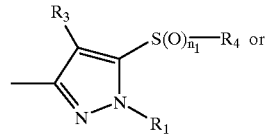

(W2a)

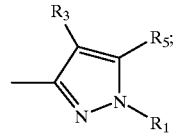

(W3a)

$R_1$, $R_2$, $R_3$, $R_4$, $R_5$, $R_{11}$, $R_{13}$ and $n_1$ are as defined under formula I; and $R_{12}$ is hydrogen, halogen, $C_1$–$C_4$alkyl, $C_2$–$C_4$alkenyl, $C_2$–$C_4$alkynyl, $C_1$–$C_4$halogenoalkyl, $C_2$–$C_4$-halogenoalkenyl, nitro, amino, CHO, $C_1$–$C_4$halogenoalkoxy, cyano, $C_3$–$C_6$cycloalkyl, phenoxy, phenoxy which is substituted once to three times by halogen, $C_1$–$C_4$alkyl or $C_1$–$C_4$halogenoalkyl, benzyloxy or benzyloxy which is substituted once to three times on the phenyl ring by halogen, $C_1$–$C_4$alkyl or $C_1$–$C_4$halogenoalkyl.

Particularly preferred compounds are those of the formula Ia in which $R_3$ is methyl, $C_1$–$C_4$halogenoalkyl, chlorine or bromine. Of these, those compounds in which Wa is the group W1a are especially preferred.

Compounds which are also especially preferred are those of the formula 1a in which Wa is the group W3a; and $R_3$ is methyl, $C_1$–$C_4$halogenoalkyl, chlorine or bromine.

Compounds which are likewise especially preferred are those of the formula Ia in which Wa is the group W3a; and $R_3$ is methyl, $C_1$–$C_4$halogenoalkyl, chlorine or bromine.

Particularly preferred compounds of the formula Ia are those in which Wa is the group W3a; and $R_3$ is $R_{18}R_{19}N$—.

Particularly important compounds of the formula Ia are those in which Wa is the group W1a; $R_1$ is $C_1$–$C_4$alkyl; $R_2$ is $C_1$- or $C_2$halogenoalkyl; $R_3$ is chlorine or bromine; A is =N—; $R_{11}$ is fluorine, chlorine or bromine; $R_{12}$ is halogen; and $R_{13}$ is hydrogen. Of these, those in which $R_1$ is methyl or ethyl; $R_2$ is halogenomethyl; $R_3$ is chlorine; $R_{11}$ is fluorine; and $R_{12}$ is chlorine are particularly important; and in particular, of these compounds, that in which $R_1$ is methyl; and $R_2$ is difluoromethyl is especially important.

The process according to the invention for the preparation of compounds of the formula I is carried out analogously to known processes, as described, for example, in WO 96/01254 and WO 97/00246, and comprises, for the purpose of preparation of those compounds of the formula I

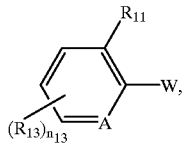

(I)

in which W is a group

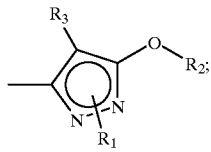

(W1)

A and $n_{13}$ are as defined under formula I; and $R_3$ is hydrogen, halogen, $C_1$–$C_4$alkyl or $C_1$–$C_4$halogenoalkyl, for example reacting a compound of the formula X

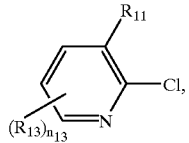

(X)

in which $R_{11}$, $R_{13}$ and $n_{13}$ are as defined, in an alcohol of the formula XV

$R_8$—OH (X), in which $R_8$ is $C_1$–$C_4$alkyl, in the presence of a suitable palladium or nickel catalyst, for example palladium bis (triphenylphosphine)dichloride ($PdCl_2(PPh_3)_2$), and a base, for example triethylamine, under an increased pressure of carbon monoxide to give the compound of the formula XI

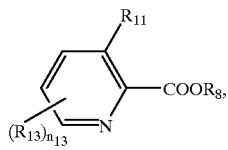

(XI)

in which $R_8$, $R_{11}$, $R_{13}$ and $n_{13}$ are as defined, hydrolysing this under acid or basic conditions to give the corresponding carboxylic acid of the formula XII

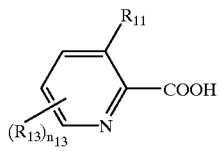

(XII)

and converting this with a carboxylic acid halogenating reagent, for example thionyl chloride, phosphorus pentachloride or oxalyl chloride, into the corresponding carboxylic acid halide of the formula XIII

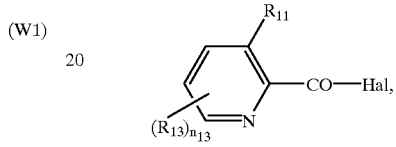

(XIII)

in which $R_{11}$, $R_{13}$ and $n_{13}$ are as defined; and Hal is halogen, preferably chlorine, and reacting this in a solvent, for example acetonitrile, in the presence of an alkaline earth metal salt, preferably magnesium chloride, and a base, for example triethylamine, with the malonic acid monoester salt of the formula XVI

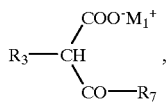

(XVI)

in which $R_3$ is hydrogen, $C_1$–$C_4$alkyl or $C_1$–$C_4$halogenoalkyl; $M_1^+$ is an alkali metal ion, preferably a potassium ion; and $R_7$ is $C_1$–$C_4$alkoxy, to give the keto ester of the formula III

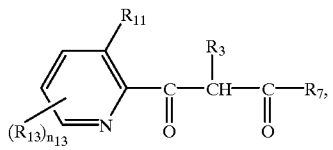

(III)

in which $R_3$, $R_7$, $R_{11}$, $R_{13}$ and $n_{13}$ are as defined, and cyclizing this in a solvent, for example glacial acetic acid, with the compound of the formula XIV $NH_2NH$—$R_1$ (XIV), in which $R_1$ is as defined under the formula I, to give the compound of the formula Ic

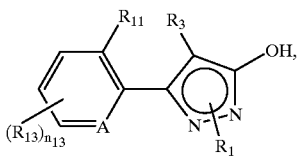

(Ic)

in which $R_1$, $R_3$, $R_{11}$, $R_{13}$ and $n_{13}$ are as defined, and then, by standard processes, functionalizing, in particular freonizing, the hydroxyl group, according to the definition of $R_2$, if appropriate halogenating the pyrazole ring ($R_3$ halogen), or oxidizing the compound to the corresponding pyridine N-oxide.

All further compounds originating from the scope of the formula I can easily be prepared in an analogous manner, in respect of the build-up of the pyrazole ring, to that described in Preparation Examples H1 to H34, or to that described, for example, in "Methoden der Organischen Chemie" [Methods of organic chemistry] (Houben-Weyl), Volume E 8b, Georg Thieme Verlag Stuttgart, 1994, page 399 et seq.; or in "Pyrazoles, Pyrazolines, Pyrazolidines, Indazoles and Condensed Rings", Editor R. H. Wiley, Interscience Publishers, John Wiley & Sons, New York, 1967, page 1 et seq.; or to that described in the following patent specifications EP-A-0 361 114, U.S. Pat. No. 5,032,165, WO 92/02509, WO 92/06962, WO 95/33728 and WO 96/01254, taking into account the chemical properties of the pyridyl moiety.

A large number of known standard processes are available for the preparation of the pyridylpyrazoles of the formula I substituted on the pyridyl ring, the choice of suitable preparation processes depending on the properties (reactivties) of the substituents in the particular intermediate. Some examples are described in Preparation Examples H1 to H34.

The starting compounds 2,5-dichloro-3-fluoropyridine, 2,3-dichloro-5-trifluoromethylpyridine and 3,5-dichloro-2-acetylpyridine used in Preparation Examples H1, H2 and H11 and the compounds of the formulae X, XIV and XVI are either known or can be prepared by processes analogous to disclosed processes.

For the preparation of the compounds of the formula I, in particular in which W is a group W3; $R_5$ is halogenoalkyl (Example H11); and $R_1$, $R_3$, $R_{11}$, $R_{13}$, A and $n_{13}$ are as defined under formula I, the compounds of the formula II

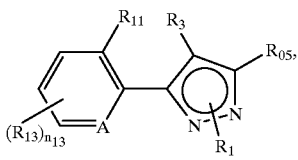

(II)

in which A, $R_1$, $R_3$, $R_{11}$, $R_{13}$ and $n_{13}$ are as defined in claim 1; $R_{05}$ is HOC(O)—, ClC(O)—, $(CH_3O)(CH_3)N$—C(O)—, $C_1$–$C_4$alkyloxycarbonyl, $NH_2C(O)$—, OHC—, $R_6O$—N=CH—, HON=CH—, $(C_1$–$C_4$alkoxy$)_2$CH—, $C_1$–$C_4$alkyl-CH (OH)—, $C_1$–$C_4$halogenoalkyl-CH(OH)—, $C_2$–$C_4$alkenyl-CH(OH)—, $C_2$–$C_4$halogenoalkenyl-CH (OH)— or $C_2$–$C_4$alkynyl-CH(OH)—; and $R_6$ is $C_1$–$C_4$alkyl, $C_1$–$C_4$halogenoalkyl, $C_1$–$C_4$alkylcarbonyl, $C_1$–$C_4$halogenoalkylcarbonyl, $C_1$–$C_4$alkylsulfonyl or $C_1$–$C_4$halogenoalkylsulfonyl, are important intermediates. The compounds of the formula IV are prepared in accordance with EP-A-0 361 114, U.S. Pat. No. 5,032,165, WO 92/02509, WO 92/06962, WO 95/33728 and WO 96/01254.

For the preparation of the compounds of the formula I in which W is a group

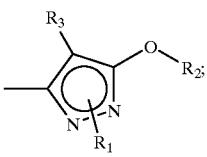

(W1)

$R_1$, $R_2$, $R_{11}$, $R_{13}$, A and $n_{13}$ are as defined under formula I; and $R_3$ is hydrogen, halogen, $C_1$–$C_4$alkyl or $C_1$–$C_4$halogenoalkyl, the compounds of the formula III

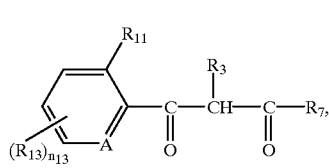

(III)

in which A, $R_{11}$, $R_{13}$ and $n_{13}$ are as defined under formula I; $R_3$ is hydrogen, $C_1$–$C_4$alkyl, halogen or $C_1$–$C_4$halogenoalkyl; and $R_7$ is $C_1$–$C_4$alkoxy, $C_1$- or $C_2$halogenoalkyl or $C_1$–$C_4$alkoxycarbonyl, the compounds of the formula III$_{01}$ and III$_{02}$

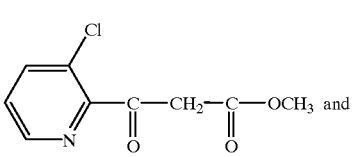

(III$_{01}$)

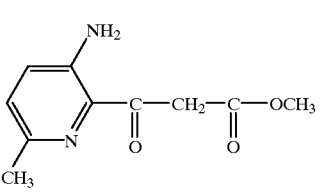

(III$_{02}$)

being excluded, are important intermediates.

For the preparation of the compounds of the formula Ia in which W is a group W3a; $R_5$ is hydrogen; and $R_1$, $R_3$, $R_{11}$, $R_{13}$, A and $n_{13}$ are as defined under formula I, the compounds of the formula IV

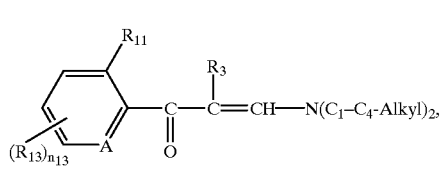

(IV)

in which A, $R_{11}$, $R_{13}$ and $n_{13}$ are as defined under formula 1; and $R_3$ is hydrogen, halogen, $C_1$–$C_4$alkyl or $C_1$–$C_4$halogenoalkyl, are important intermediates.

The compounds of the formula IV are prepared in accordance with EP-A-0 361 114, U.S. Pat. No. 5,032,165, WO 92/02509, WO 92/06962, WO 95/33728 and WO 96/01254.

For the preparation of the compounds of the formula I in which W is a group W3

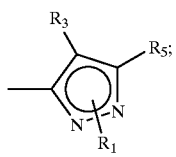
(W3)

$R_3$ is hydrogen, $C_1$–$C_4$alkyl or $C_1$–$C_4$halogenoalkyl; $R_5$ is amino;
and $R_1$, $R_{11}$, $R_{13}$, A and $n_{13}$ are as defined under formula I; the compounds of the formula V

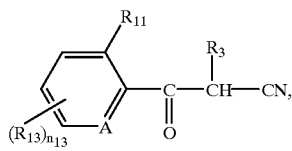
(V)

in which A, $R_{11}$, $R_{13}$ and $n_{13}$ are as defined under formula I; and $R_3$ is hydrogen, $C_1$–$C_4$alkyl or $C_1$–$C_4$halogenoalkyl, are important intermediates.
The compounds of the formula V are prepared in accordance with EP-A-0 361 114, U.S. Pat. No. 5,032,165, WO 92/02509, WO 92/06962, WO 95/33728 and WO 96/01254.

The intermediates of the formulae II, III, IV and V are novel. The invention thus also relates to these compounds, excluding the comounds of the formulae $III_{O1}$ and $III_{O2}$

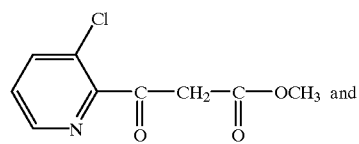
($III_{O1}$)

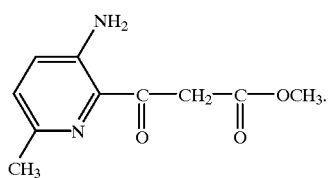
($III_{O2}$)

All further compounds originating from the scope of the formula I can easily be prepared by processes analogous to those according to Preparation Examples H1 to H34, or in a manner analogous to that described in "Methoden der Organischen Chemie" [Methods of organic chemistry] (Houben-Weyl), Volume E 8b, Georg Thieme Verlag Stuttgart, 1994, page 399 et seq.; ibid, Volume E7B, Georg Thieme Verlag Stuttgart, 1992, page 286 et seq.; in "Pyrazoles, Pyrazolines, Pyrazolidines, Indazoles and Condensed Rings", Editor R. H. Wiley, Interscience Publishers, John Wiley & Sons, New York, 1967, page 1 et seq.; or in "Comprehensive Heterocyclic Chemistry", Editors A. R. Katritzky and C. W. Rees, Pergamon Press, Oxford, 1987, or by derivatization by known standard methods, as described, for example, in "Advanced Organic Chemistry", Third Edition, Editor J. March, John Wiley & Sons, New York, 1985; in "Comprehensive Organic Transformations", Editor R. C. Larock, VCH Publishers, Inc., New York, 1989; or in "Comprehensive Organic Functional Group Transformations", Editors A. R. Katritzky, O. Meth-Cohn, C. W. Rees, Pergamon Press, Oxford, 1995, or as described in the following patent specifications EP-A-0 361114, US-A-5 032 165, WO 92/02509, WO 92106962, WO 95/33728 and WO 96/01254, taking into consideration the particular chemical reactivities.

The end products of the formula I can be isolated in the customary manner by concentration or evaporation of the solvent and can be purified by recrystallization or trituration of the solid residue in solvents in which they do not dissolve readily, such as ethers, aromatic hydrocarbons or chlorinated hydrocarbons, by distillation or by means of column chromatography and a suitable eluting agent.

The sequence in which certain reactions are advantageously to be carried out in order possibly to avoid secondary reactions is also familiar to the expert.

If no controlled synthesis is carried out for isolation of pure isomers, the product can be obtained as a mixture of two or more isomers. These isomers can be separated by methods known per se.

The compounds of the formula I or compositions comprising them can be used according to the invention by all the application methods customary in agriculture, for example preemergence application, postemergence application and seed dressing, and various methods and techniques, for example controlled release of active substances. For this, the active substance is adsorbed in solution onto mineral granule carriers or polymerized granules (urea/formaldehyde) and dried. If appropriate, a coating which allows the active substance to be released in metered form over a certain period of time can additionally be applied (coated granules).

The compounds of the formula I can be employed in unchanged form, i.e. as they are obtained in the synthesis, but they are preferably processed in a customary manner with the auxiliaries conventionally used in the art of formulation, for example to give emulsifiable concentrates, directly sprayable or dilutable solutions, dilute emulsions, wettable powders, soluble powders, dusts, granules or microcapsules. The methods of application, such as spraying, atomizing, dusting, wefting, scattering or pouring, in the same way as the nature of the compositions, are chosen according to the required aims and the given circumstances.

The formulations, i.e. the compositions, formulations or preparations comprising the active substance of the formula I or at least one active substance of the formula I and as a rule one or more solid or liquid formulation auxiliaries, are prepared in a known manner, for example by intimate mixing and/or grinding of the active substances with the formulation auxiliaries, for example solvents or solid carriers. Surface-active compounds (surfactants) can furthermore additionally be used during preparation of the formulations.

Possible solvents are: aromatic hydrocarbons, preferably fractions $C_8$ to $C_{12}$, for example xylene mixtures or substituted naphthalenes, phthalic acid esters, such as dibutyl or dioctyl phthalate, aliphatic hydrocarbons, such as cyclohexane or paraffins, alcohols and glycols, and their ethers and esters, such as ethanol, ethylene glycol, ethylene glycol monomethyl or -ethyl ether, ketones, such as cyclohexanone, strongly polar solvents, such as N-methyl-2-pyrrolidone, dimethyl sulfoxide or N,N-dimethylformamide, and epoxidized or non-epoxidized vegetable oils, such as epoxidized coconut oil or soya oil; or water.

Solid carriers which are as a rule used, for example for dusts and disposable powders, are natural rock powders, such as calcite, talc, kaolin, montmorillonite or attapulgite.

To improve the physical properties of the formulation, highly disperse silicic acid or highly disperse absorbent polymers can also be added. Granular, adsorptive granule carriers are porous types, for example pumice, crushed brick, sepiolite or bentonite, and non-sorptive carrier materials can be, for example, calcite or sand. A large number of pregranulated materials of inorganic or organic nature, such as, in particular, dolomite or comminuted plant residues, can also be used.

Possible surface-active compounds are nonionic, cationic and/or anionic surfactants and surfactant mixtures having good emulsifying, dispersing and wetting properties, depending on the nature of the active substance of the formula I to be formulated.

Suitable anionic surfactants can be both so-called water-soluble soaps and water-soluble synthetic surface-active compounds.

Possible soaps are the alkali metal, alkaline earth metal or substituted or unsubstituted ammonium salts of higher fatty acids ($C_{10}$–$C_{22}$), for example the Na or K salts of oleic or stearic acid, or of naturally occurring fatty acid mixtures, which can be obtained, for example, from coconut oil or tallow oil. Fatty acid methyl-taurine salts may furthermore also be mentioned.

More often, however, so-called synthetic surfactants are used, in particular fatty alcohol sulfonates, fatty alcohol sulfates, sulfonated benzimidazole derivatives or alkylarylsulfonates.

The fatty alcohol sulfonates or sulfates are as a rule in the form of alkali metal, alkaline earth metal or substituted or unsubstituted ammonium salts and contain an alkyl radical having 8 to 22 C atoms, alkyl also including the alkyl moiety of acyl radicals, for example the Na or Ca salt of ligninsulfonic acid, of dodecylsulfuric acid ester or of a fatty alcohol sulfate mixture prepared from naturally occurring fatty acids. These also include the salts of sulfuric acid esters and sulfonic acids of fatty alcohol/ethylene oxide adducts. The sulfonated benzimidazole derivatives preferably contain 2 sulfonic acid groups and a fatty acid radical having 8–22 C atoms. Alkylarylsulfonates are, for example, the Na, Ca or triethanolamine salts of dodecylbenzenesulfonic acid, of dibutynaphthalenesulfonic acid or of a naphthalenesulfonic acid/formaldehyde condensation product. Corresponding phosphates, for example salts of the phosphoric acid ester of a p-nonylphenol-(4-14)-ethylene oxide adduct, or phospholipids can furthermore also be used.

Nonionic surfactants are, in particular, polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols.

Further suitable nonionic surfactants are the water-soluble adducts, containing 20 to 250 ethylene glycol ether groups and 10 to 100 propylene glycol ether groups, of polyethylene oxide on polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit.

Examples of nonionic surfactants are nonyiphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, can furthermore also be used.

The cationic surfactants are, in particular, quaternary ammonium salts which contain at least one alkyl radical having 8 to 22 C atoms as N substituents, and lower, halogenated or non-halogenated alkyl, benzyl or lower hydroxyalkyl radicals as further substituents. The salts are preferably present as halides, methyl sulfates or ethyl sulfates, for example stearyltrimethylammonium chloride or benzyldi(2-chloroethyl)ethylammonium bromide.

The surfactants conventionally used in the art of formulation and which can also be used in the compositions according to the invention are described, inter alia, in "Mc Cutcheon's Detergents and Emulsifiers Annual" MC Publishing Corp., Ridgewood N.J., 1981, Stache, H., "Tensid-Taschenbuch" [Surfactant handbook], Carl Hanser Verlag, Munich/Vienna, 1981 and M. and J. Ash, "Encyclopedia of Surfactants", Vol I–III, Chemical Publishing Co., New York, 1980–81.

The herbicidal formulations as a rule comprise 0.1 to 99% by weight, in particular 0.1 to 95% by weight, of herbicide, 1 to 99.9% by weight, in particular 5 to 99.8% by weight, of a solid or liquid formulation auxiliary and 0 to 25% by weight, in particular 0.1 to 25% by weight, of a surfactant.

While concentrated compositions are rather preferred as commercial goods, the end user as a rule uses dilute compositions.

The compositions can also comprise further additives, such as stabilizers, for example epoxidized or non-epoxidized vegetable oils (epoxidized coconut oil, rapeseed oil or soya oil), defoamers, for example silicone oil, preservatives, viscosity regulators, binders, tackifiers and fertilizers or other active substances.

In particular, preferred formulations have the following compositions: (%=per cent by weight)

| Emulsifiable concentrates: | |
|---|---|
| Active substance: | 1 to 90%, preferably 5 to 50% |
| Surface-active agent: | 5 to 30%, preferably 10 to 20% |
| Solvent: | 15 to 94%, preferably 70 to 85% |
| Dusts: | |
| Active substance: | 0.1 to 50%, preferably 0.1 to 1% |
| Solid carrier: | 99.9 to 90%, preferably 999 to 99% |
| Suspension concentrates: | |
| Active substance: | 5 to 75%, preferably 10 to 50% |
| Water: | 94 to 24%, preferably 88 to 30% |
| Surface-active agent: | 1 to 40%, preferably 2 to 30% |
| Wettable powders: | |
| Active substance: | 0.5 to 90%, preferably 1 to 80% |
| Surface-active agent: | 0.5 to 20%, preferably 1 to 15% |
| Solid carrier material: | 5 to 95%, preferably 15 to 90% |
| Granules: | |
| Active substance: | 0.1 to 30%, preferably 0.1 to 15% |
| Solid carrier: | 99.5 to 70%, preferably 97 to 85% |

The active substances of the formula I, either as a mixture comprising the isomers Ia and Ib or as pure isomers Ia or Ib, can as a rule be employed successfully on plants or their environment with rates of application of 0.001 to 4 kg/ha, in particular 0.005 to 2 kg/ha. The dosage required for the desired action can be determined by tests. It depends on the nature of the action, the stage of development of the crop plants and of the weeds and on the application (location, time, method), and can vary within wide limits, depending on these parameters.

The compounds of the formula I and as a rule in particular the isomers of the formula la are distinguished by herbicidal and growth-inhibiting properties which enable them to be employed in crops of useful plants, in particular in cereals, cotton, soya, sugarbeet, sugarcane, plantations, oilseed rape, maize and rice, and for non-selective weed control ('Total Vegetation Management', TVM).

Crops are also to be understood as meaning those which have been rendered tolerant to herbicides or classes of herbicides by conventional breeding or genetic engineering methods. The weeds to be controlled can be both mono- and dicotyledon weeds, for example Stellaria, Nasturtium, Agrostis, Digitaria, Avena, Setaria, Sinapis, Lolium, Solanum, Phaseolus, Echinochioa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola and Veronica.

The following examples illustrate the invention further without limiting it.

PREPARATION EXAMPLES

Example H1
Ethyl 3-fluoro-5-chloro-2-pyridinecarboxglate

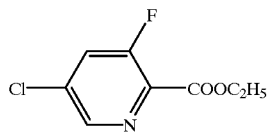

An autoclave is loaded with 31.4 g of 2,5-dichloro-3-fluoropyridine, 400 ml of dry ethanol, 27.8 ml of triethylamine and 3.5 g of palladium bis(triphenylphosphine) dichloride ($PdCl_2(PPh_3)_2$), and 180 bar of carbon monoxide are then forced in. The mixture is then kept at 90° C. for 4 days. After cooling and letting down the pressure, a further 3.5 g of $PdCl_2(PPh_3)_2$ are added, 130 bar of carbon monoxide are forced in and the temperature is kept at 90° C. for 3 days. Thereafter, the mixture is cooled to 25° C., the pressure is let down and the autoclave is unloaded. After the mixture has been concentrated in vacuo, the residue is adsorbed onto silica gel from ethyl acetate. After the silica gel has been applied to a flash chromatography column (silica gel), the column is eluted with n-hexane/ethyl acetate 3/1. 24.3 g of the desired target compound of melting point 48–50° C. are obtained.

Example H2
Ethyl 3-chloro-5trifluoromethyl-2-pyridinecarboxylate

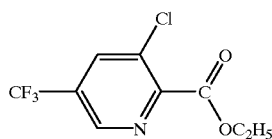

An autoclave is loaded with 200 g of 2,3-dichloro-5-trifluoromethylpyridine, 1.85 l of ethanol, 260 ml of triethylamine and 6.5 g of palladium bis(triphenylphosphine) dichloride ($PdCl_2(PPh_3)_2$). 110 bar of carbon monoxide are then forced in at 25° C. and the mixture is kept at 110° C. for 24 hours. After cooling to 25° C., the crude mixture is concentrated to a thick slurry, which is then partitioned between dilute sodium chloride solution and ethyl acetate. After extraction by shaking and separation of the phases, the ethyl acetate phase is washed with water, dried over sodium sulfate and concentrated to dryness. The crude product is distilled under a high vacuum at 0.035 mbar. 200 g of the desired product are obtained as a yellow oil of boiling point 67–70° C./0.035 mbar (yield 85% of theory)

Example H3
3-Chloro-5-trifluoromethyl-2-pyridinecarboxylic acid

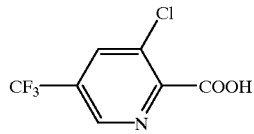

423 g of ethyl 3-chloro-5-trifluoromethyl-2-pyridinecarboxylate (Example H2) is initially introduced into a mixture of 800 ml of water and 160 ml of ethanol. 800 ml of a 2N sodium hydroxide solution are added dropwise at a temperature below 35° C. After 3 hours, the mixture is washed twice with methylene chloride and then rendered acid with an excess of concentrated hydrochloric acid, while cooling in an ice-bath. The slurry formed is filtered and the solid is washed with water and dried in vacuo. 318 g of the desired product are obtained as a white solid of melting point 135° C. (decomposition).

Example H4
3-Fluoro-5-chloro-2-pyridinecarboxylic acid

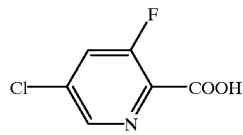

70 g of ethyl 3-fluoro-5-chloro-2-pyridinecarboxylate (Example H1) are initially introduced into 105 ml of dimethyl sulfoxide (DMSO). 230 ml of a 2N sodium hydroxide solution are added dropwise at 40° C. in the course of 30 minutes. The resulting yellow suspension is introduced into a mixture of 2 l of ice-water and 400 ml of 2N hydrochloric acid. After subsequently stirring for 20 minutes, the mixture is filtered and the material on the filter is washed twice with water. 56.4 g of the desired target compound are obtained as a white solid.

$^1$H-NMR (DMSO-$D_6$): 13.79 ppm (broad signal, 1H); 8.60 ppm (d, 1H); 8.27 ppm (dxd, 1H).

Example H5
3-Chloro-5-trifluoromethyl-2-pyridinecarbonyl chloride

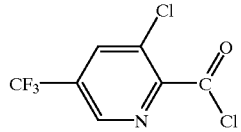

89.3 g of 3-chloro-5-trifluoromethyl-2-pyridinecarboxylic acid (Example H3) are slowly heated to reflux temperature together with 60 ml of thionyl chloride and the mixture is then subsequently stirred at this temperature for 4 hours. Thereafter, it is cooled to 25° C. and concentrated to dryness in vacuo. Toluene is added twice more and the mixture is concentrated again to dryness. 94.0 g of the desired product are obtained as a yellow residue.

$^1$H-NMR (CDCl$_3$): 8.91 ppm (d, 1H); 8.13 ppm (d, 1H).

Example H6
3-Fluoro-5-chloro-2-pyridinecarbonyl chloride

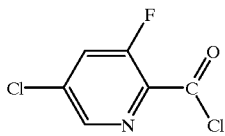

71.38 g of 3-fluoro-5-chloro-2-pyridinecarboxylic acid is initially introduced into a round-bottomed flask and heated up to 90° C. 59 ml of thionyl chloride are added dropwise from a dropping funnel in the course of 30 minutes, and the gas formed is passed into sodium hydroxide solution. The mixture is subsequently stirred at 100° C. for a further 5 hours. The thionyl chloride is then distilled off under normal pressure. After addition of 50 ml of dry toluene, 20 ml thereof are distilled off. The solution thus obtained is poured onto 200 ml of n-hexane and the mixture is stirred overnight. After cooling in an ice-bath, the mixture is filtered and the material on the filter is washed twice with n-hexane. 68.7 9 of the desired compound are obtained as a brown solid.

$^1$H-NMR (CDCl$_3$): 8.60 ppm (d, 1H); 7.69 ppm (dxd, 1H).

Example H7
3-Fluoro-5-chloro-2-pyridinecarboxamide

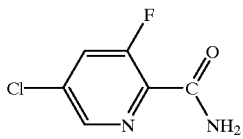

4.0 g of 3-fluoro-5chloro-2-pyridinecarbonyl chloride (Example H6) are added in portions to a stirred mixture of 26 ml of 30% aqueous ammonia solution and 4 ml of tetrahydrofuran. The yellowish suspension is subsequently stirred for 4 hours and filtered and the material on the filter is washed with water and n-hexane. After drying in vacuo at 40° C., 1.34 g of the desired compound are obtained as a white solid of melting point 162–164° C.
The combined aqueous phases are extracted with ethyl acetate. After the organic phase has been washed and dried, it is filtered and the filtrate is concentrated. A further 6.25 g of the desired target compound are isolated in this manner.

Example H8
3-Fluoro-5-chloro-2-cyanopyridine

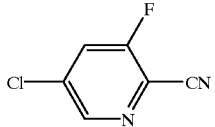

1.39 g of 3-fluoro-5-chloro-2-pyridinecarboxamide (Example H7) are initially introduced into 8 ml of absolute dioxane, and 1.3 ml of dry pyridine are added. 1.30 ml of trifluoroacetic anhydride are slowly added with a syringe, while stirring and cooling in an ice-bath, and the mixture is subsequently stirred for 30 minutes. The resulting reaction mixture is poured onto 1N hydrochloric acid at 25° C. and extracted with diethyl ether. The ether phase is washed with dilute hydrochloric acid, water, dilute sodium bicarbonate solution and water. After drying over sodium sulfate, the mixture is filtered and the filtrate is concentrated to dryness. 1.14 g of the desired compound are obtained as a slightly violet-coloured solid of melting point 72–73° C.

Example H9
3-Chloro-5-trifluoromethyl-2-acetylopridine

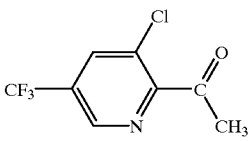

55.3 ml of dimethyl malonate are stirred together with 129 ml of triethylamine and 24.9 g of anhydrous magnesium chloride in 250 ml of dry toluene for 2 hours. Under an exothermic reaction, the reaction temperature rises to 45° C. 94.0 g of 3-chloro-5-trifluoromethyl-2-pyridinecarbonyl chloride (Example H5) in 150 ml of toluene are added dropwise at 25° C. and the reaction mixture is stirred further overnight. An excess of concentrated hydrochloric acid is then added dropwise, and the mixture is diluted with water and extracted with ethyl acetate. The organic phase is washed with brine, dried over sodium sulfate, filtered and concentrated. 142 g of a red oil are obtained, and the oil is slowly introduced into a mixture of 20 ml of water and 400 ml of dimethyl sulfoxide, which is kept under gentle reflux with the aid of an oil-bath of 150° C. When no further evolution of gas can be detected, water is added and the mixture is extracted with ether. The combined ether phases are washed with water, dried over sodium sulfate, filtered and concentrated. The residue is purified by means of column chromatography (silica gel; eluting agent: n-hexanelethyl acetate 15/1 (vN)). 61 g of the desired product are obtained as a yellow oil (70% of theory).

$^1$H-NMR (CDCA$_3$): 8.81 ppm (d, 1H); 8.05 ppm (d, 1H); 2.72 ppm (s, 3H).

Example H10
1-3-Chloro-5-trifluoromethyl-2-pyridyl-3-dimethylamino-2-propen-1-one

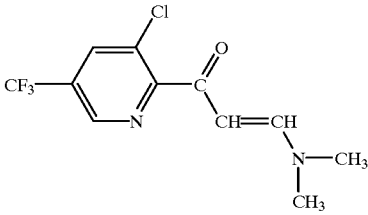

5.0 g of 3-chloro-5-trifluoromethyl-2-acetylpyridine (Example H9) are initially introduced into 30 ml of toluene, and 3.60 ml of N,N-dimethylformamide dimethyl acetal are added. The yellow solution formed is stirred overnight at 100° C. After cooling to 25° C., it is concentrated to dryness in vacuo. 6.17 g of the desired target compound are obtained as a dark yellow oil, which later solidifies.

$^1$H-NMR (CDCl$_3$): 8.74 ppm (d, 1H); 7.98 ppm (d, 1H); 7.92 ppm (broad signal, 1H); 5.54 ppm (broad d, 1H); 3.17 ppm (broad signal, 3H); 2.94 ppm (broad signal, 3H).

Example H11
3-(3,5-Dichloro-2-pyridyl)-5-trifluoromethyl-[1H]-pyrazole (Compound No. I₁₁₇.052)

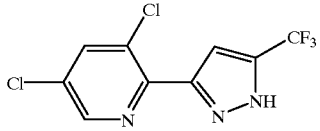

15.8 g of 3,5-dichloro-2-acetylpyridine are initially introduced into 125 ml of absolute ether together with 12.0 ml of ethyl trifluoroacetate. The mixture is cooled with an ice-bath, while stirring, and 46.6 ml of a 21% sodium ethylate solution in ethanol are added dropwise. Thereafter, the ice-bath is removed and the mixture is subsequently stirred overnight at 25° C. After the reaction mixture has been cooled in an ice-bath and 7.5 ml of glacial acetic acid have been added dropwise, the mixture is concentrated in vacuo. 39.0 g of 1-(3,5-dichloro-2-pyridyl)-3-trifluoromethyl-propane-1,3-dione, which can be used directly for the following cyclization step, are obtained.

39.0 g of 1-(3,5-dichloro-2-pyridyl)-3-trifluoromethyl-propane-1,3-dione (Compound No. III₄.052)

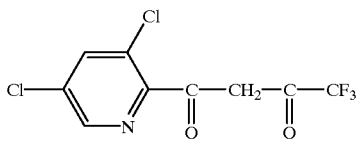

are initially introduced into ethanol, and 4.85 ml of hydrazine hydrate are slowly added. The reaction mixture is then heated to reflux, while stirring. After 1 hour, it is concentrated to dryness in vacuo and the residue is partitioned between dilute sodium bicarbonate solution and ethyl acetate. After extraction by shaking and separation of the phases, the organic phase is washed with brine, dried over sodium sulfate, filtered and concentrated to dryness. 22.25 g of a yellow oil are obtained, and this is purified by means of flash chromatography (silica gel, eluting agent: n-hexane/ethyl acetate 4/1 (v/v)). 15.0 g of the desired product are obtained as a yellow solid.

$^1$H-NMR (DMSO-D₆): 8.81 ppm (m, 1H); 8.64 ppm (m, 1H); 8.26 ppm (m, 1H); 7.45 ppm (broad signal, 1H).

Example H12

3-(3,5-Dichloro-2-pyridyl)-5-trifluoromethyl-1-methyl-[1H]-pyrazole and 5-(3,5-dichloro-2-pyridyl)-3-trifluoromethyl-1-methyl-[1H]-pyrazole (Compound No. I₁₁₅.052)

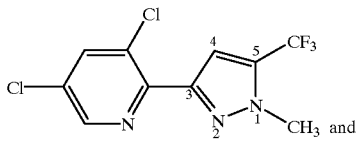

and

-continued

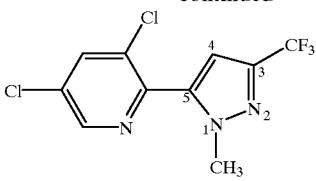

8.88 g of 3-(3,5-dichloro-2-pyridyl)-5-trifluoromethyl-[1H]-pyrazole (Example H11) are initially introduced into 35 ml of N-methylpyrrolidone. After addition of 13.0 g of potassium carbonate, the mixture is stirred and heated up to 55° C. 2.36 ml of methyl iodide in 5.0 ml of N-methylpyrrolidone are then slowly added dropwise. After the mixture has been subsequently stirred for 2 hours, diethyl ether and water are added, the mixture is extracted by shaking and the organic phase is separated off. The ether phase which has been separated off is washed with brine, dried over sodium sulfate, filtered and concentrated. The crude product is purified by means of flash chromatography (silica gel; eluting agent: toluene/ethyl acetate 100/1). First, 3.96 g of the isomeric 5-pyridylpyrazole (yield 42%) are isolated as a yellow oil, and then 1.96 g of the 3-pyridylpyrazoie (yield 21%) are isolated as a yellow solid. The Rf values of the two isomeric 3- and 5-pyridyipyrazoles are as follows on silica gel 60 F₂₅₄ with toluene/ethyl acetate 30/1 as the eluting agent (UV):
Rf value 5-pyridylpyrazole: 0.50
Rf value 3-pyridylpyrazole: 0.35

Example H13
3-(3,5-dichloro-2-pyridyl)-4-chloro-5-trifluoromethyl-1-methyl-[1H]-pyrazole (Compound No. I₄.243)

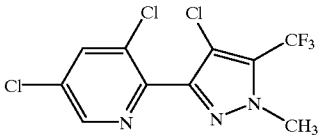

2.0 g of 3-(3,5-dichloro-2-pyridyl)-5-trifluoromethyl-1-methyl-[1H]-pyrazole (Example H12) are initially introduced into glacial acetic acid at 40° C., and chlorine gas is passed slowly over the solution, while stirring. The reaction can be monitored analytically by means of thin layer chromatography (silica gel 60 F₂₅₄, eluting agent: n-hexane/ethyl acetate 4/1, UV). When no further starting material can be detected, the glacial acetic acid is removed in vacuo and the residue is partitioned between dilute aqueous sodium hydroxide solution and ethyl acetate. After extraction by shaking, the organic phase which has been separated off is washed with brine, dried over sodium sulfate, filtered and concentrated. The yellow oil is purified by means of flash chromatography (silica gel, eluting agent: n-hexane/ethyl acetate 5/1). 1.6 g of the desired compound are obtained as a yellow oil (70% of theory).

$^1$H-NMR (DMSO-D₆): 8.80 ppm (d, 1H), 8.48 ppm (d, 1H), 4.11 ppm (s, 3H)

The isomeric 5-pyridylpyrazole is also obtained analogously in a 90% yield (crude).

$^1$H-NMR (CDCl₃): 8.66 ppm (d, 1H); 7.95 ppm (d, 1H); 3.83 ppm (s, 3H).

Example H14
3-(3-Fluoro-5-chloro-2-pyridyl)-5-hydroxy-1-methyl-[1H]-pyrazole (Compound No. I₁₀₈.035)

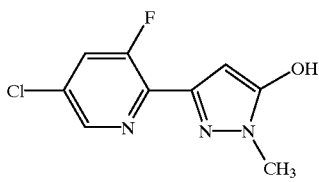

110.6 g of malonic acid monomethyl ester•potassium salt are initially introduced into 500 ml of absolute acetonitrile. The mixture is cooled in an ice-bath, while stirring, and 109 ml of triethylamine are added dropwise. 84.3 g of anhydrous magnesium chloride are then added. A mild exothermic reaction is observed. After removal of the ice-bath, the mixture is subsequently stirred at 25° C. for 2 hours. After renewed cooling in the ice-bath, 68.7 g of 3-fluoro-5-chloro-2-pyridinecarbonyl chloride (Example H6), in several portions, and 300 ml of absolute acetonitrile are added. A thick slurry gradually forms. The cooling bath is removed and the mixture is subsequently stirred for 5 hours. Thereafter, the reaction mixture is poured onto 3 l of ice-water and 200 ml of concentrated hydrochloric acid, subsequently stirred for 15 minutes and extracted with ethyl acetate. The organic phase is washed with water and brine, dried over sodium sulfate, filtered and concentrated to dryness in vacuo. 110 g of a brown oil, which is used directly for the next reaction stage, are obtained.

For this next stage, the brown oil obtained above is introduced at 25° C. into a solution of 20.5 ml of methylhydrazine in 300 ml of glacial acetic acid and the mixture is then stirred at 85° C. for 2 hours. The brown suspension formed is introduced, after cooling to 25° C., into 2.5 l of ice-water in portions, the mixture is stirred for 1 hour and filtered and the solid is washed with water and n-hexane. After drying at 60° C. in vacuo, 65.8 g of the desired title compound of melting point 195–199° C. are obtained.

Example H15
3-(3-Fluoro-5chloro-2-pyridyl)-5-difluoromethoxy-1-methyl-[1H]-pyrazole (Compound No. I₁₀₇.035)

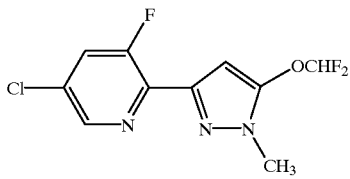

46.0 g of 3-(3-fluoro-5-chloro-2-pyridyl)-5-hydroxy-1-methyl-[1H]-pyrazole (Example H14) and 84 g of potassium carbonate are initially introduced into 250 ml of dry dimethylformamide and the mixture is heated up to 85° C. Freon 22 (chlorodifluoromethane) is then passed in over a period of 2 hours, with thorough stirring. TLC analysis of a worked-up sample (silica gel 60 F₂₅₄; n-hexane/ethyl acetate/glacial acetic acid 20/20/1, UV) shows that no further starting material is present. The reaction mixture is partitioned between water and diethyl ether (foaming on addition of water). After extraction by shaking and separation of the phases, the ether phase is washed twice with water and once with brine. After the organic phase has been dried over sodium sulfate and filtered, the filtrate is concentrated in vacuo and the residue is purified by means of flash chromatography (silica gel; eluting agent: n-hexane/ethyl acetate 2/1 (v/v)). 22.0 g of the desired title compound are obtained as a pale yellow solid.

$^1$H-NMR (CDCl₃): 8.51 ppm (broad signal, ₁H); 7.56 ppm (dxd, 1H); 6.61 ppm (t, 1H); 6.53 ppm (d, 1H); 3.89 ppm (s, 3H).

Example H16
3-(3-Fluoro-5-chloro-2-pyridyl)-4-chloro-5-difluoromethoxy-1-methyl-[1H]-pyrazole (Compound No. I₁.002)

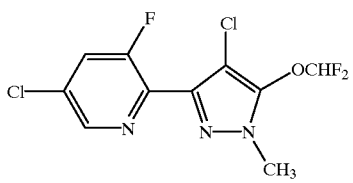

17.92 g of 3-(3-fluoro-5-chloro-2-pyridyl)-5-difluoromethoxy-1-methyl-[1H]-pyrazole (Example H15) are initially introduced into 60 ml of glacial acetic acid together with 10.6 g of sodium acetate. The mixture is heated up to 60° C., while stirring, and a saturated solution of chlorine in glacial acetic acid is added until TLC analysis of a worked-up sample shows a complete conversion (silica gel 60 F₂₅₄; eluting agent: n-hexane/ethyl acetate 2/1; UV; Rf value of the starting material 0.34; Rf value of the product 0.48). The mixture is then concentrated to dryness in vacuo and the resulting residue is partitioned between sodium bicarbonate solution and ethyl acetate. The organic phase is washed with brine, dried over sodium sulfate, filtered and evaporated to dryness in vacuo. 19.8 g of the desired target compound (pure according to TLC) are obtained. Melting point 95–96° C.

Example H18
3-(5-Chloro-2-pyridyl-N-oxide)-4-chloro-5-trifluoromethyl-1-methyl-[1H]-pyrazole (Compound No. I₆₃.001)

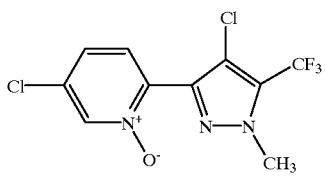

6.82 g of 3-(5-chloro-2-pyridyl)-4-chloro-5-trifluoromethyl-1-methyl-[1H]-pyrazole are initially introduced into 30 ml of methylene chloride at 25° C. 7.23 g of m-chloroperbenzoic acid are added, while stirring. After 48 hours, a further 2.50 g of m-chloroperbenzoic acid are added. After a further 24 hours, the reaction mixture is taken up in ethyl acetate and extracted twice with dilute sodium hydroxide solution, rinsed with brine, dried over sodium sulfate and concentrated. The residue is then chromatographed (silica gel; eluting agent. n-hexane/ethyl acetate 1/1 (v/v)). 6.31 g of the desired compound are isolated as a white solid.

$^1$H-NMR (DMSO-D₆): 8.75 ppm (d, 1H); 7.66 ppm (d, 1H); 7.59 ppm (dxd, 1H); 4.08 ppm (s, 3H).

Starting from the isomeric 5-(5-chloro-2-pyridyl)-4-chloro-3-trifluormmethyl-1-methyl-[1H]-pyrazole, the isomeric 5-(5-chloro-2-pyridyl-N-oxide)-4-chloro-3-trifluomomethyl-1-methyl-[1H]-pyrazole can be obtained in a 70% yield

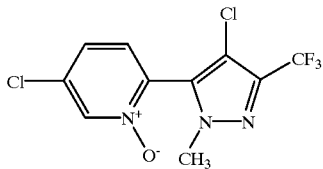

Example H19
3-(3-Fluoro-5-chloro-2-pyridyl-N-oxide)-4-chloro-5-difluoromethoxy-1-methyl-[1H]-pyrazole (Compound No. $I_{68}.002$)

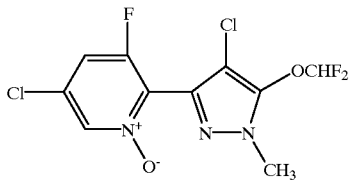

0.57 g of 3-(3-fluoro-5-chloro-2-pyridyl)-4-chloro-5-difluoromethoxy-1-methyl-[1H]-pyrazole (Example H16) is initially introduced into 5 ml of methylene chloride, and 0.63 g of a 55% m-chloroperbenzoic acid is added. After the crude mixture has been stirred at 25° C. for 4 days, it is taken up in ethyl acetate and washed successively with sodium bicarbonate solution, water and brine. After drying over sodium sulfate and filtering, the filtrate is concentrated and the residue is purified by means of flash chromatography. 0.45 g of the desired target compound is obtained as a white solid of melting point 115–120° C.

Example H20
3-(5,6-Dichloro-2-pyridyl)- and 3-(4.5-dichloro-2-pyridyl)-4-chloro-5-trifluoromethyl-1-methyl-[1H]-pyrazole (isomer A and B)

(Compound No. $I_4.485$)

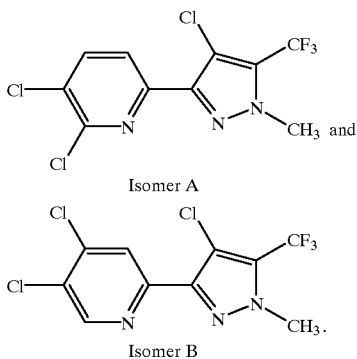

20 ml of phosphorus oxychloride (POCl$_3$) are heated up to 90° C. 10.37 g of 3-(5-chloro-2-pyridyl-N-oxide)-4-chloro-5trifluoromethyl-1-methyl-[1H]-pyrazole (Example H18) are introduced in several portions at this temperature, while stirring, and the mixture is subsequently stirred at 90° C. for 1 hour. The phosphorus oxychloride is then removed in vacuo and the residue is taken up in diethyl ether. The organic phase is then washed successively with water, 0.5 N sodium hydroxide solution and brine. After drying over sodium sulfate and filtering, the filtrate is concentrated. 8.93 g of a brown precipitate are obtained. This crude product is purified by column chromatography (silica gel; eluting agent: n-hexane/ethyl acetate 10/1). First, 0.57 g of isomer B is isolated, and then 5.11 g of isomer A are isolated as a white solid.

TLC analysis: silica gel 60 $F_{254}$; eluting agent: n-hexane/ethyl acetate 4/1 (v/v), UV:
Rf value isomer A: 0.31
Rf value isomer B: 0.41

If 6.3 g of 3-(5-chloro-2-pyridyl-N-oxide)-4-chloro-5-trifluoromethyl-1-methyl-[1H]-pyrazole (Example H18) are treated with 6.3 g of phosphorus pentachloride in 20 ml of phosphorus oxychloride at 90° C. for 1 hour, 4.36 g of isomer A and 1.01 g of isomer B are obtained after the above working up.

Example H21
3-(3Fluoro-5,6-dichloro-2-pyridyl)- and 3-(3-fluoro-4,5dichloro-2-pyridyl)-4-chloro-5-difluoromethoxy-1-methyl-[1H]-pyrazole (isomer A and B)

(Compound No. $I_1.003$)

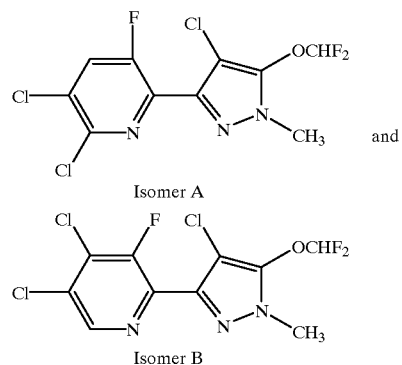

A mixture of 2.1 g of phosphorus pentachloride and 7 ml of phosphorus oxychloride is heated up to 90° C., 2.8 g 3-(3-fluoro-5-chloro-2-pyridyl-N-oxide)-4-chloro-5-difluoromethoxy-1-methyl-[1H]-pyrazole (Example H19) is then introduced in portions at this temperature and the mixture is stirred at the same temperature for 0.5 hour. Most of the phosphorus oxychloride is then removed in vacuo and the remaining mixture is stirred with warm water and ethyl acetate. The organic phase which has been separated off is washed with aqueous sodium bicarbonate solution and brine. After drying over sodium sulfate and filtering, the filtrate is concentrated in vacuo and the residue is purified by means of flash chromatography (silica gel; eluting agent: toluene/ethyl acetate 50/1). 0.69 g of isomer A is first isolated as a yellow oil, which later solidifies; melting point 63–67° C. 0.64 g of isomer B is then obtained as a white solid of melting point 121–123° C.

Example H22
3-(6-Ethoxycarbonyl-5-chloro-2-pyridyl)-4-chloro-5-trifluoromethyl-1-methyl-[1H]-pyrazole (Compound No. I4.733)

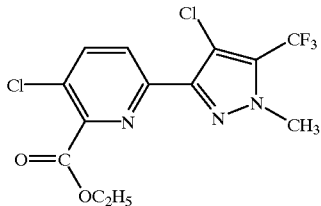

An autoclave is loaded with 7.0 g of 3-(5,6-dichloro-2-pyridyl)-4chloro 5trifluoromethyl-1-methyl-[1H]-pyrazole (Example H20), 100 ml of dry ethanol, 9.0 ml of triethylamine and 0.83 g of palladium bistriphenylphosphine dichloride (PdCl$_2$(PPh$_3$)$_2$). 140 bar of carbon monoxide are forced in at 25° C. and the mixture is then kept at 120° C. for 15 hours. After cooling to 25° C., the mixture is concentrated and the residue is then absorbed onto silica gel from ethyl acetate. This silica gel is introduced onto a flash chromatography column and the column is then eluted with a mixture of n-hexane/ethyl acetate 7/1 (v/v). 4.51 g of the desired title compound are obtained as a yellow solid (58% of theory). TLC analysis: Rf value of the product (silica gel 60 F$_{254}$, n-hexane/ethyl acetate 4/1 (v/v)): 0.19.

Example H23

3-(6-Chlorocarbonyl-5-chloro-2-pyridyl)-4-chloro-5trifluoromethyl-1-methyl-1-[1H]-pyrazole (Compound No. I4.546)

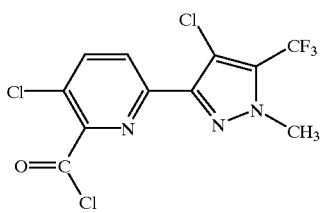

5.44 g of 3-(6-ethoxycarbonyl-5-chloro-2-pyridyl)-4-chloro-5trifluoromethyl-1-methyl-[1H]-pyrazole are initially introduced into a flask, and 4.1 ml of a 4 N solution of sodium hydroxide in 4.1 ml of a mixture of methano/water 2/1 are added. The reaction mixture is heated up to 40° C. and kept at this temperature overnight. It is then concentrated to dryness under a high vacuum and 2.2 ml of thionyl chloride are added to the resulting residue. The mixture is heated up to 80° C. in the course of 2 hours. After cooling to 25° C., it is concentrated to dryness in vacuo. The residue is then diluted 3 times with carbon tetrachloride and in each case concentrated to dryness in vacuo. 5.56 g of a solid, which is used directly for the next reaction stage, are obtained.

Example H24

3-[5-Chloro-6-(carboxylic acid 1-allyloxycarbonyl-1-methyl-ethyl ester)-2-pyridyl]-4-chloro-5-trifluoromethyl-1-methyl-[1H]-pyrazole (Compound No. I4.566)

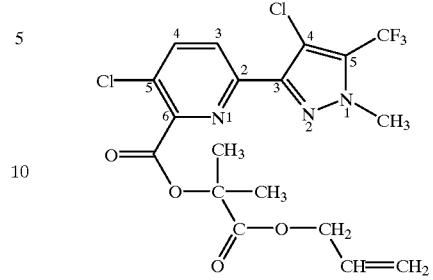

2.56 g of allyl hydroxyisobutyrate are initially introduced into 15 ml of dry pyridine. 5.30 g of 3-(6-chlorocarbonyl-5-chloro-2-pyridyl)-4-chloro-5-trifluoromethyl-1-methyl-[1 H]-pyrazole (Example H23) are added in several portions at 25° C., under an exothermic reaction, and the mixture is subsequently stirred overnight at 25° C. The reaction mixture is then concentrated in vacuo and the residue is taken up in ethyl acetate. The ethyl acetate phase is washed successively with water, dilute ammonium chloride solution, water, dilute sodium bicarbonate solution and water. 5.5 g of the desired title compound are obtained as a brown solid.
$^1$H-NMR (CDCl$_3$): 7.94 ppm (d, 1H); 7.84 ppm (d, 1H); 5.94 ppm (m, 1H); 5.29 ppm (m, 2H); 4.70 ppm (d, 2H); 4.07 ppm (s, 3H); 1.75 ppm (s, 6H)

Example H25

3-[5-Chloro-6-(carboxylic acid 1-carboxy-1-methyl-ethyl ester)-2-pyridyl]-4-chloro-5-trifluoromethyl-1-methyl-[1H]-pyrazole (Compound No. I4.562)

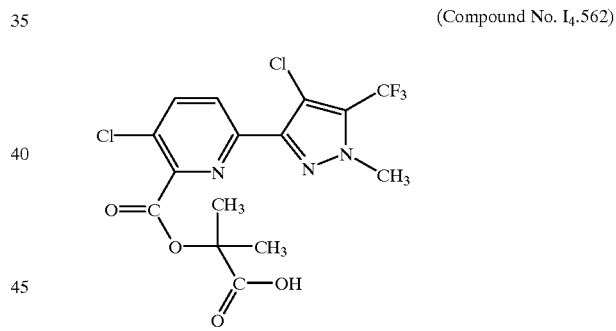

3.53 g of 3-[5-chloro-6-(carboxylic acid 1-allyloxycarbonyl-1-methyl-ethyl ester)-2-pyridyl]-4-chloro-5trifluoromethyl-1-methyl-[1 H]-pyrazole (Example H24) are initially introduced into 30 ml of acetonitrile together with 0.1 g of triphenylphosphine. After five evacuations under a water pump vacuum and subsequent gassing with argon, 0.22 g of Pd(PPh$_3$)$_4$ and, after cooling to 0° C., 0.70 ml of pyrrolidine are added under argon. The mixture is stirred at 25° C. for 4 hours. It is then concentrated in vacuo and the resulting residue is partitioned between ethyl acetate and a phosphate buffer pH =3. The organic phase is washed with the buffer solution and then with brine. After drying over sodium sulfate and filtering, it is concentrated to dryness in vacuo, 3.92 g of a brown solid remaining. After purification over a flash chromatography column (silica gel; eluting agent: n-hexanelethyl acetate/acetic acid 100/100/3), 3.23 g of the desired title compound are obtained.
$^1$H-NMR (DMSO-D$_6$): 13.60 ppm (broad signal, 1H); 8.22 ppm (d, 1H); 8.03 ppm (d, 1H); 4.11 ppm (s, 3H); 1.62 ppm (s, 6H).

Example H26
3-[5-Chloro-6-(carboxylic acid 1-chlorocarbonyl-1-methyl-ethyl ester)-2-pyridyl-4-chloro-5-trifluoromethyl-1-methyl-[1H]-pyrazole (Compound No. I4.804)

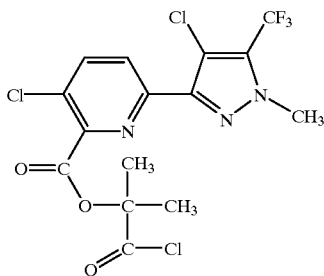

3.12 g of 3-[5-chloro-6-(carboxylic acid 1-carboxy-1-methyl-ethyl ester)-2-pyridyl]-4-chloro-5-trifluoromethyl-1-methyl-[1H]-pyrazole (Example H 25) are initially introduced into 20 ml of dry toluene and the mixture is heated up to 80° C. After addition of one drop of N,N-dimethylformamide, 1.1 ml of thionyl chloride are added dropwise, while stirring. After the mixture has been subsequently stirred at 80° C. for 1 hour, it is cooled to 25° C. and concentrated in vacuo. After dissolving the resulting residue in 25 ml of absolute toluene and concentrating the solution again, 3.21 g of a yellow solid, which is used directly for the next reaction stage, are obtained.

Example H27
3-[5-Chloro-6-(carboxylic acid 1-allylcarbamoyl-1-methyl-ethyl ester)-2-pyridyl]-4-chloro-5-trifluoromethyl-1-methyl-[1H]-pyrazole (Compound No. I4.570)

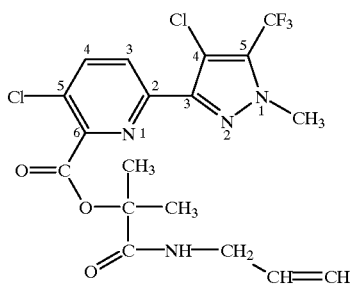

0.15 ml of allylamine is initially introduced into 4.0 ml of dry pyridine. 0.81 g of 3-[5-Chloro-6-(carboxylic acid 1-chlorocarbonyl-1-methyl-ethyl ester)-2-pyridyl]-4-chloro-5-trifluoromethyl-1-methyl-[1H]-pyrazole (Example H26) is added in several portions, while stirring, at a temperature below 5° C. and the mixture is then stirred at 25° C. for 3 hours. The resulting dark red solution is partitioned between dilute hydrochloric acid and ethyl acetate. After extraction by shaking and separation of the phases, the organic phase is washed successively with water, dilute sodium hydroxide solution and finally with brine. After drying over sodium sulfate, the mixture is filtered and the filtrate is concentrated to dryness. 0.79 g of the desired title compound is obtained as an orange solid.

$^1$N-NMR (CDCl$_3$): 7.99 ppm (d, 1H); 7.89 ppm (d, 1H); 7.07 ppm (broad signal, 1H); 5.81 ppm (m, 1H); 5.09 ppm (m, 2H); 4.08 ppm (s, 3H); 1.88 ppm (s, 6H).

Example H28
3-(5-Chloro-6-methoxy-2-pyridyl)-4-chloro-5-trifluoromethyl-1-methyl-[1H]-pyrazole (Compound No. I4.498)

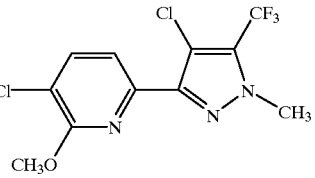

1.0 g of 3-(5,6-dichloro-2-pyridyl)-4-chloro-5-trifluoromethyl-1-methyl-[1 H]-pyrazole (Example H20) is initially introduced into 5 ml of dry dimethoxyethane. After the solution has been cooled to 0° C., 0.61 ml of a 5.4 molar solution of sodium methylate in methanol is added dropwise and the mixture is subsequently stirred at 25° C. for 2 days. The reaction mixture is taken up in diethyl ether and washed successively with 0.5 N hydrochloric acid, water and brine. After drying over sodium sulfate, the mixture is filtered and the filtrate is concentrated to dryness in vacuo. 0.94 g of the desired title compound is obtained as a white solid.

$^1$H-NMR (DMSO-D$_6$): 7.99 ppm (d, 1H); 7.50 ppm (d, 1H); 4.08 ppm (s, 3H); 4.02 ppm (s, 3H).

Example H29
3-[5-Chloro-6-(imidazol-1-yl)-2-pyridyl]-4-chloro-5-trifluoromethyl-1-methyl-[1H]-pyrazole (Compound No. I4.729)

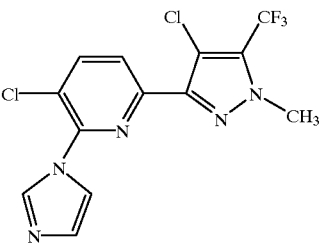

0.60 g of 3-(5,6-dichloro-2-pyridyl)-4-chloro-5-trifluoromethyl-1-methyl-[1]-pyrazole (Example H20), 0.28 g of imidazole and 0.50 g of potassium carbonate are initially introduced into 10 ml of dry N-methylpyrrolidone. The mixture is stirred overnight at 100° C. and then cooled to 25° C. and partitioned between water and diethyl ether. After extraction by shaking and separation of the phases, the ether phase is washed with water, ammonium chloride solution and water. After drying over sodium sulfate and filtering, the filtrate is concentrated in vacuo and the residue is purified over a flash chromatography column (silica gel; eluting agent: n-hexane/ethyl acetate 1/2). 0.42 g of the desired compound is obtained as a white solid.

TLC analysis: silica gel 60 F$_{254}$; eluting agent: n-hexane/ethyl acetate 1/2;
R$_1$ value starting material: 0.71
R$_f$ value target compound: 0.27.

Example H30
3-(3-Fluoro-5-chloro-6-hydroxy-2-pyridyl)-4-chloro-5-difluoromethoxy-methyl-[1H]-pyrazole (Compound No. I₁.005)

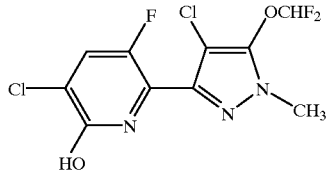

1.0 g of 3-(3-fluoro-5-chloro-2-pyridine-N-oxide)-4-chloro-5-difluoromethoxy-1-methyl-[1H]-pyrazole is initially introduced into 12 ml of dry N,N-dimethylformamide. 4.2 ml of trifluoroacetic anhydride is added dropwise from a syringe, while stirring and cooling with an ice-bath, and the mixture is then subsequently stirred overnight at 25° C. It is then evaporated in vacuo and the residue is partitioned between diethyl ether and water. After extraction by shaking and separation of the phases, the ether phase is washed with dilute aqueous sodium bicarbonate solution and brine, dried over sodium sulfate, filtered and concentrated. 1.23 g of a yellow oil are obtained, and this is purified by means of flash chromatography (silica gel; eluting agent: n-hexane/ethyl acetate 2/3 (v/v) and 1% glacial acetic acid). 0.59 g of the desired compound is obtained as a yellow solid of melting point 126–128° C.

Example H31

3-(3-Fluoro-5-chloro-6-methoxy-2-pyridyl)-4-chloro-5-difluoromethoxy-1-methyl-[1H]-pyrazole (Compound No. I₁.022)

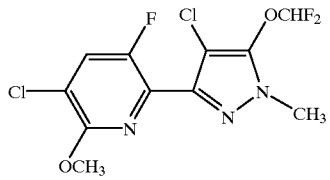

0.1 g of 3-(3-fluoro-5-chloro-6-hydroxy-2-pyridyl)-4-chloro-5-difluoromethoxy-1-methyl-[1H]-pyrazole (Example H30) is initially introduced into 2.0 ml of dry N,N-dimethylformamide.

After addition of 0.12 g of dry powdered potassium carbonate, 0.06 g of methyl iodide in 1 ml of dry N,N-dimethylformamide is added at 25° C., while stirring. After 3 hours, the reaction mixture is partitioned between water and diethyl ether. The ether phase which has been separated off is washed with water and brine, dried over sodium sulfate, filtered and concentrated. After purification over a flash chromatography column (silica gel; eluting agent: n-hexane/ethyl acetate 2/1 (v/v)), 0.07 g of the desired product is isolated as a white solid.
TLC analysis: silica gel 60 F₂₅₄; eluting agent: n-hexane/ethyl acetate 1/1 (v/v):
$R_f$ value product: 0.57
$R_f$ value precursor: 0.14.

Example H32

3-(3-Fluoro-5-chloro-2-pyridyl)-4-difluoromethyl-5-difluoromethoxy-1-methyl-[1H]-pyrazole (Compound No. I₁₀₃.002)

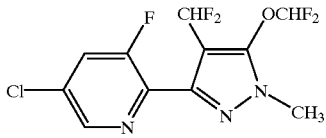

0.13 g of 3-(3-fluoro-5-chloro-2-pyridyl)-4-formyl-5-difluoromethoxy-1-methyl-[1H]-pyrazole is initially introduced into 3.0 ml of dry 1,2-dichloroethane. 0.11 ml of diethylaminosulfur trifluoride (DAST) is added dropwise with a syringe, while stirring, the reaction mixture assuming a dark colour. The mixture is then stirred at 50° C. for 1 hour. After cooling to 25° C., the reaction solution is applied directly to a flash chromatography column (silica gel) and eluted with n-hexane/ethyl acetate 5/1 (v/v). 0.07 g of the desired compound is obtained as a pale yellow solid of melting point 79–81° C.

Example H33

3-(3-Fluoro-5-chloro-2-pyridyl)-4-formyl-5-difluoromethoxy-1-methyl-[1H]-pyrazole (Compound No. I₁₀₄.002)

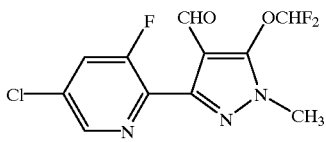

2.41 ml of phosphorus oxychloride are introduced into 5 ml of N,N-dimethylformamide, while cooling in an ice-bath, and the mixture is subsequently stirred at 25° C. for 2 hours. This mixture is then added dropwise to 5.0 g of 3-(3-fluoro-5-chloro-2-pyridyl)-5-hydroxy-1-methyl-[1H]-pyrazole (Example H14) in 15 ml of N,N-dimethylformamide at 80° C. in the course of 30 minutes. After the mixture has been subsequently stirred at 80° C. for 1.5 hours, it is cooled to 25° C., ice and then water are added and the mixture is extracted with diethyl ether. After washing the organic phase with water and drying over sodium sulfate, 1.1 g of a yellow solid is obtained as an intermediate. This is initially introduced into 10 ml of dry N,N-dimethylformamide together with 1.72 g of powdered anhydrous potassium carbonate. The mixture is heated up to 75° C., while stirring thoroughly, and Freon 22 (CHClF₂) is passed in slowly for 7 hours. The mixture is then cooled to 25° C. and taken up in diethyl ether. The ether phase is washed with water and then with brine, dried over sodium sulfate, filtered and concentrated. 1.50 g of crude product are obtained as a brown solid, which is purified by means of a flash chromatography column (silica gel; eluting agent: n-hexanelethyl acetate 4/1 (v/v)). 0.14 g of the desired target compound is obtained as a yellow solid of melting point 111–116° C. in this manner.

Example H34

3-(3-Fluoro-5-chloro-6cyano-2-2-pyridyl)-4-chloro-5-difluoromethoxy-1-methyl-[1H]-pyrazole (Compound No. I₁.009)

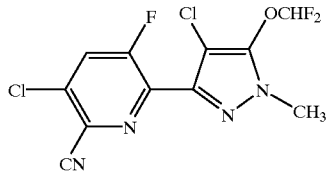

1.50 g of 3-(3-fluoro-5-chloro-2-pyridyl-N-oxide)-4-chloro-5-difluoromethoxy- 1-methyl-[1H]-pyrazole (Example H19) are initially introduced into 5 ml of dry acetonitrile, and 1.0 ml of triethylamine is then added. 1.43 ml of trimethylsilyl cyanide in 2 ml of acetonitrile are then added dropwise at 25° C. in the course of 20 minutes, and the mixture is stirred for 2 days, while heating vigorously under reflux (bath temperature 110° C.). After cooling to 25° C., the mixture is diluted with acetonitrile, adsorbed onto silica gel and introduced onto a flash chromatography column (silica gel). After eluting with a mixture of n-hexane/ethyl acetate 3/1 (v/v), 0.74 g of the desired product is obtained as a yellow solid of melting point 133–134° C.

Example H35
3-(3-Fluoro-5-chloro-6-vinyl-2-pyridyl)-4-chloro-5-difluoromethoxy-1-methyl-[1H]-pyrazole (Compound No. I₁.740)

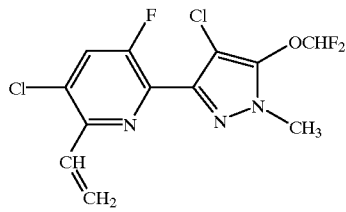

30 g of 3-(3-fluoro-5,6-dichloro-2-pyridyl)-4-chloro-5-difluoromethoxy-1-methyl-[1H]-pyrazole (Example H21) are dissolved in 200 ml of N,N-dimethylformamide (DMF). After addition of 32.9 g of vinyltributyltin, the mixture is twice evacuated and gassed with argon. A little (i.e. a spatula-tip) 2,6-di-tert-butyl-p-cresol and 3.0 g of bistriphenylphosphinepalladium dichloride (PdCl₂(PPh₃)₂) are then added and the mixture is stirred at a temperature of 67° C. for 24 hours. After cooling to 22° C., the reaction mixture is filtered over Hyflo and partitioned between dilute hydrochloric acid and diethyl ether. The ether phase which has been separated off is washed with water, dried over sodium sulfate, filtered and concentrated in vacuo. 84 g of a black oil are obtained, and this is purified over a silica gel flash column (eluting agent: n-hexanelethyl acetate 6/1). The resulting solid is stirred with 100 ml of n-hexane for a further 2 hours, filtered off, washed and dried. 16.4 g of the desired title compound are obtained as a white solid of melting point 75–77° C.

Example H36
3-(3-Fluoro-5-chloro-6-formyl-2-pyridyl)-4-chloro-5-difluoromethoxy-1-methyl-[1H]-pyrazole (Compound No. I₁.113)

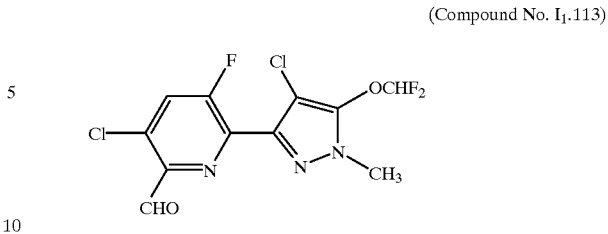

13.2 g of 3-(3-fluoro-5-chloro-6-vinyl-2-pyridyl)-4-chloro-5-difluoromethoxy-1-methyl-[1 H]-pyrazole (Example H35) are initially introduced into a mixture of 120 ml of dioxane and 40 ml of water. 16.7 g of sodium (meta)periodate (NaIO₄) and a spatula-tip of osmium tetroxide are added, while stirring, and the mixture is subsequently stirred overnight at 22° C. The following day, the resulting mixture is taken up in ethyl acetate and washed first with dilute hydrochloric acid and then with brine. After drying over sodium sulfate, the mixture is filtered and the filtrate is concentrated in vacuo. After purification over a silica gel flash column (eluting agent: n-hexane/ethyl acetate 2/1), 9.4 g of the desired title compound are obtained as a white solid of melting point 120–121° C.

Example H37
3-[3-Fluoro-5-chloro-6-(carboxylic acid 1-carboxy-1-methyl-ethyl ester)-2pyridyl]-4-chloro-5-difluoromethoxy-1-methyl-[1H]-2pyrazole (Compound No. I₁.152)

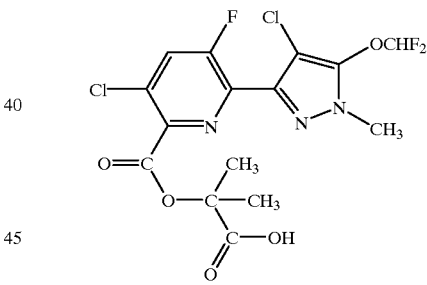

4.9 g of 3-13-Fluoro-5-chloro-6-(carboxylic acid 1-benzyloxycarbonyl-1-methyl-ethyl ester)-2-pyridyl]-4-chloro-5-difiuoromethoxy-1-methyl-[1H]-pyrazole are hydrogenated with 1.0 g of 5% palladium on active charcoal in 70 ml of ethyl acetate at 22° C. under normal pressure. After 20 minutes, the mixture is filtered over Hyflo, dried over sodium sulfate, filtered and concentrated in vacuo. The resulting crude product is purified over a silica gel flash column (eluting agent: toluene/acetic acid 10/1). 3.8 g of the desired title compound are obtained as a white solid of melting point 133–134° C.

Example H38
3-[3-Fluoro-5-chloro-6-(carboxylic acid 1-isopropylmercaptocarbonyl-1-methyl-ethyl ester)-2-pyridyl]-4-chloro-5-difluoromethogy-1-methyl-[1H]-pyrazole (Compound No. I₁.164)

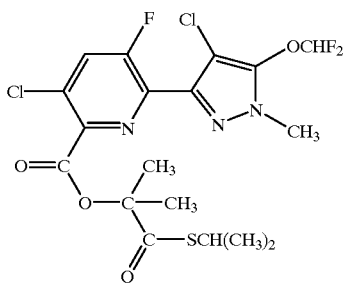

2.23 g of 3-[3-fluoro-5-chloro-6(carboxylic acid 1-carboxy-1-methyl-ethyl ester)-2-pyridyl]-4-chloro-5-difluoromethoxy-1-methyl-[1H]-pyrazole (Example H37) are initially introduced into 10 ml of methylene chloride. A catalytic amount of DMF and 0.67 g of oxalyl chloride, in portions, are added to the white suspension (evolution of gas). The mixture is subsequently stirred at 22° C. for 1 hour. The colourless acid chloride solution thus obtained can be further used directly.
0.64 g of triethylamine and 1 spatula-tip of p-dimethylaminopyridine (DMAP) are initially introduced into 10 ml of ethyl acetate. 0.23 g of 2-propanethiol is added, while cooling with ice, and half of the acid chloride solution obtained above is added dropwise in the course of 15 minutes. The mixture is then stirred at 22° C. for 3 hours. Thereafter, the remaining amount of 2-propanethiol is removed with argon gas passed over Javelle water. The resulting mixture is diluted with ethyl acetate and washed with dilute hydrochloric acid and then with brine. The resulting crude product is purified over a silica gel flash column (eluting agent: n-hexane/ethyl acetate 4/1). 1.16 g of a colourless oil which slowly crystallizes out are obtained. The solid is comminuted and stirred with 3 ml of n-hexane. After filtration with suction, washing and drying, 1.05 g of the desired title compound are obtained as white crystals of melting point 81–82° C.

Example H39
3-(3-Fluoro-5-chloro-6-methacrylic acid ethyl ester-2-pyridyl)-4-chloro-5-difluoromethoxy-1-methyl-[1H]-pyrazole (Compound No. I₁.764)

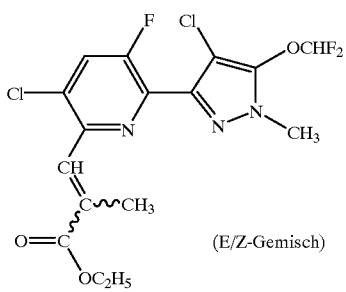

(E/Z-Gemisch)

1.00 g of 3-(3-fluoro-5-chloro-6-formyl-2-pyridyl)-4-chloro-5-difluoromethoxy-1-methyl-[1H]-pyrazole (Example H36) is initially introduced into 6 ml of dioxane and 0.1 ml of water, and 0.88 g of triethyl 2-phosphonopropionate and 1.44 g of caesium carbonate are added. The mixture is then stirred at 80° C. for 2 hours and the resulting reaction mixture is diluted with ethyl acetate and washed first with dilute hydrochloric acid and then with brine. After drying over sodium sulfate, filtering and concentrating in vacuo, the residue is purified over a silica gel flash column (eluting agent: toluene/ethyl acetate 10/1). 0.86 g of an isomer A and 0.37 g of an isomer B are obtained.
¹H-NMR (CDCl₃): Isomer A: 7.56 ppm (d, 1H); 6.86 ppm (m, 1H); 6.70 ppm (t, 1H); 4.05 ppm (q, 2H); 3.85 ppm (s, 3H); 2.15 ppm (m, 3H); 1.03 ppm (t, 3H). Isomer B: 7.85 ppm (m, 1H); 7.62 ppm (d,₁H); 6.72 ppm (t, 1H); 4.29 ppm (q, 2H); 3.87 ppm (s, 3H); 2.29 ppm (m, 3H); 1.35 ppm (t, 3H).

Example H40
3-(3-Fluoro-5-chloro-2-pyridyl)-5-bromo-1-methyl-[1H]-pyrazole (Compound No. I₁₃₁.035)

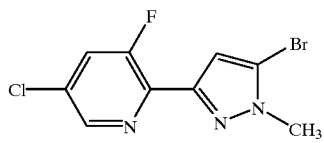

20.0 g of 3-(3-fluoro-5-chloro-2-pyridyl)-5-hydroxy-1-methyl-[1H]-pyrazole (Example H14) are initially introduced into 80 ml of tetrachloroethane. A total of 25.2 g of phosphorus oxybromide (POBr₃) are added in portions to the brown suspension and the mixture is then stirred at a temperature of 130° C. for 2 hours. Thereafter, it is cooled and 150 ml of a 2 molar sodium hydroxide solution are added dropwise, while cooling with an ice-bath. After addition of diethyl ether and separation of the phases, the organic phase is washed successively with water, dilute hydrochloric acid and brine, dried over sodium sulfate, filtered and concentrated in vacuo. 19.94 g of a brown solid are obtained as the crude product, and this solid is purified by means of digestion with 50 ml of n-hexane. 12.65 g of the desired title compound are obtained as a brown solid of melting point 110–111° C.

Example H41
3-(3-Fluoro-5-chloro-2-pyridyl)-5-ethoxycarbonyl-1-methyl-[1H]-pyrazole

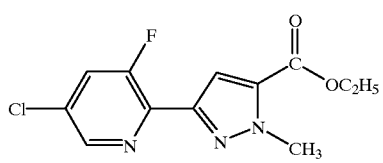

5.0 g of 3-(3-fluoro-5-chloro-2-pyridyl)-5-bromo-1-methyl-[1H]-pyrazole (Example H40) are initially introduced into an autoclave together with 7.2 ml of triethylamine, 0.48 g of bis-triphenylphosphinepalladium dichloride (PdCl₂(PPh₃)₂) and 70 ml of absolute ethanol. 100 bar of carbon monoxide are forced in at 22° C. and the mixture is then kept at 100° C. for 48 hours. In the meantime, a further 0.48 g of bis-triphenylphosphinepalladium dichloride is added. The mixture is then cooled to 22° C. and the pressure is released. The resulting reaction mixture is filtered over Hyflo and—after removal of the ethanol—taken up in ethyl acetate. The ethyl acetate phase is washed with dilute hydrochloric acid and then with brine, dried over sodium sulfate, filtered and concentrated in vacuo. 3.17 g of a brown solid are obtained, and this gives, after purification over a silica gel flash column (eluting agent: n-hexane/ethyl acetate 2/1), 2.31 g of the desired title compound as a pale yellow solid of melting point 117–118° C.

Example H42

3-(3-Fluoro-5-chloro-2-pyridyl)-4-chloro-5-trifluoromethyl-1-methyl-[1H]-pyrazole (Compound No. I$_4$.002)

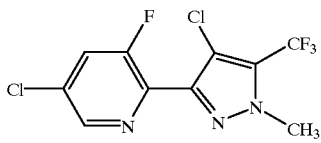

8.63 g of 3-(3-fluoro-5-chloro-2-pyridyl)-4-chloro-5-carboxy-1-methyl-[1H]-pyrazole are initially introduced into a fluorinating unit with 27 g of hydrogen fluoride (HF), 16.2 g of sulfur tetrafluoride (SF$_4$) and 270 ml of methylene chloride. This mixture is kept at 80° C. for 5 hours. It is then cooled to 22° C. and the SF$_4$ is removed via a gas elimination unit (stream of argon) and the HF is removed under a water pump vacuum. After addition of methylene chloride, the mixture is extracted three times with ice-water and the organic phase which has been separated off is dried over sodium sulfate and then concentrated in vacuo together with 40 g of silica gel. After application of this silica gel to a flash column, the column is eluted with a mixture of n-hexane/ethyl acetate 5/1. 5.48 g of the desired title compound are obtained as a beige solid of melting point 76–78° C.

Example H43

3-(3-Fluoro-5-chloro-2-pyridyl)-4-methyl-5-carboxy-1-methyl-[1H]-pyrazole (Compound No. I$_{130}$.035)

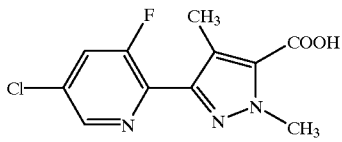

6.75 g of 3-(3-fluoro-5-chloro-2-pyridyl)-4-methyl-5methoxycarbonyl-1-methyl-[1H]-pyrazole are suspended in 40 ml of dimethyl sulfoxide. 14.3 ml of a 2 molar sodium hydroxide solution are added dropwise, while cooling occasionally in an ice-bath (temperature <30° C.). The thick yellow-brown suspension is stirred at 22° C. for 2 hours. The resulting suspension is then introduced into ice-water and the pH is brought to 1 with 2 molar hydrochloric acid. The slurry formed is filtered with suction and the solid is washed thoroughly with cold water and then dried in vacuo at 60° C. 5.97 g of the desired title compound are obtained as a beige solid of melting point 194–196° C.

Example H44

3-(3-Fluoro5-chloro-2-pyridyl)-4-methyl-5-carbamoyl-1-methyl-[1H]-pyrazole (Compound No. II$_{10}$.035)

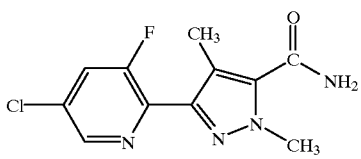

3.0 g of 3-(3-fluoro-5-chloro-2-pyridyl)-4-methyl-5-carboxyl-1-methyl-[1 H]-pyrazole (Example H43) are initially introduced into 25 ml of 1,2-dichloroethane, a total of 1.2 ml of thionyl chloride are slowly added at 80° C. and the mixture is subsequently stirred at 80° C for 5 hours. The resulting mixture is concentrated in vacuo and three times 20 ml of carbon tetrachloride are added and in each case the mixture is evaporated to dryness. The resulting acid chloride is initially introduced into 35 ml of tetrahydrofuran, and ammonia gas is passed in, while cooling in an ice-bath. A brown precipitate forms. Stirring is continued overnight at 22° C. The resulting suspension is then introduced into five times the volume of ice-water. After brief subsequent stirring, the solid is filtered off with suction, washed with cold water and dried in vacuo at 60° C. 2.0 g of the desired title compound are obtained as a brown solid of melting point 201–204° C. in this manner.

Example H45

3-(3-Fluoro-5-chloro-2-pyridyl)-4-methyl-5-cyano-1-methyl-[1H]-pyrazole (Compound No. I$_{10}$.002)

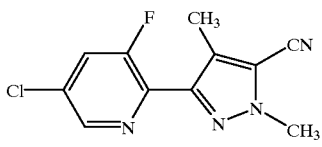

1.82 g of 3-(3-fluoro-5-chloro-2-pyridyl)-4-methyl-5-carbamoyl-1-methyl-[1H]-pyrazole (Example H44) are suspended in 20 ml of dioxane. First 1.65 ml of pyridine and then 1.44 ml of trifluoroacetic anhydride are added, while cooling in an ice-bath. 5 minutes later, the cooling bath is removed and the mixture is stirred at 22° C. for 1 hour. The brown-red solution is diluted with diethyl ether and washed with one molar hydrochloric acid and then with brine. After drying over sodium sulfate and filtering, the filtrate is concentrated directly together with twice the amount of silica gel. After application of this silica gel to a flash column, the column is eluted with n-hexane/ethyl acetate 4/1. 1.60 g of the desired title compound are obtained as a beige solid of melting point 144–146° C.

Example H46

3-(3-Fluoro-5-chloro-2-pyridyl)-4-iodo-5-difluoromethoxy-1-methyl-[1H]-pyrazole (Compound No. I₁₃₅.035)

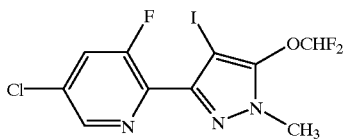

3.0 g of 3-(3-fluoro-5-chloro-2-pyridyl)-5-difluoromethoxy-1-methyl-[1H]-pyrazole (Example H15) are dissolved in 30 ml of methylene chloride, and 1.83 g of silver(I) nitrite and 3.02 g of iodine are then added. The mixture is stirred overnight at 22° C. It is then diluted with diethyl ether and extracted successively with aqueous sodium metabisulfite solution and brine. After drying of the organic phase over sodium sulfate and filtration, the filtrate is concentrated in vacuo together with twice the amount of silica gel. After application of this silica gel to a flash column, the column is eluted with n-hexane/ethyl acetate (3/1). 3.97 g of the desired title compound are obtained as a beige solid of melting point 77–78° C. in this manner.

Example H47
3-(3-Fluoro-5-chloro-2-pyridyl)-4-nitro-5-difluoromethoxy-1-methyl-[1H]-pyrazole (Compound No. I₁₃₆.035)

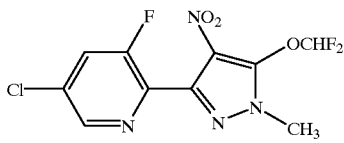

4.0 g of 3-(3-fluoro-5chloro-2-pyridyl)-5-difluoromethoxy-1-methyl-[1H]-pyrazole (Example HIS) are initially introduced into 30 ml of methylene chloride. 3.83 g of nitronium tetrafluoroborate are added, while stirring and cooling in an ice-bath, and the mixture is subsequently stirred overnight at 22° C. The following day, it is poured onto water, and ethyl acetate is added. After extraction by shaking and separation of the phases, the organic phase is washed with dilute bicarbonate solution and brine, dried over sodium sulfate, filtered and concentrated in vacuo. 4.35 g of the desired title compound are obtained as a brown solid of melting point 108–109° C.

Example H48
3-(3-Fluoro-5-chloro-2-pyridyl)-4-amino-5difluoromethoxy-1-methyl-[1H]-pyrazole (Compound No. I₁₃₄.035)

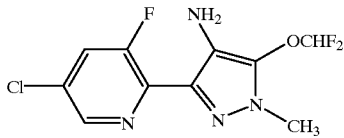

4.2 g of 3-(3-fluoro-5-chloro-2-pyridyl)-4-nitro-5-difluoromethoxy-1-methyl-[1H]-pyrazole (Example H47) are initially introduced into the reaction vessel together with 40 ml of tetrahydrofuran, and 5.8 g of Raney nickel in ethanol are added. Hydrogenation is carried out under normal pressure and at a temperature of 30–35° C. After uptake of 728 ml of hydrogen, the hydrogenation is interrupted and the reaction mixture is filtered over Hyflo. After removal of the solvent in vacuo, 3.15 g of the desired title compound are obtained as a brown solid of melting point 92–94° C.

Example H49
3-(3-Fluoro-5chloro-2-pyridyl)-4-(2-chloropropionamido-5-difluoromethoxy-1-methyl-[1H]-pyrazole (Compound No. I₁₄₇.101)

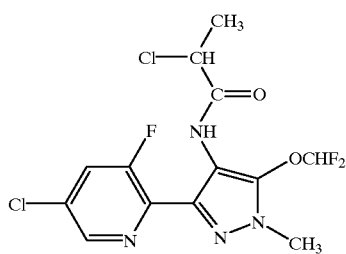

1.0 g of 3-(3-fluoro-5-chloro-2-pyridyl)-4-amino-5-difluoromethoxy-1-methyl-[1H]-pyrazole (Example H148) is initially introduced into 4 ml of pyridine. 0.46 g of racemic 2-chloropropionyl chloride in 4 ml of methylene chloride is added dropwise over 30 minutes, while stirring and cooling in an ice-bath, and the mixture is then subsequently stirred at 22° C. for 2 hours. The reaction mixture is taken up in ethyl acetate and washed with dilute hydrochloric acid and then with brine. After drying over sodium sulfate and filtering, the filtrate is concentrated in vacuo and the residue is then purified over a silica gel flash column (eluting agent: toluene/ethyl acetate 10/1). 0.98 g of the desired title compound is obtained as a white solid of melting point 153–154° C.

Example H50
3-(3 Fluoro-5-chloro-6-amino-2-pyridyl)-4-chloro-5-difluoromethoxy-1-methyl-[1H]-pyrazole (Compound No. I₁.004)

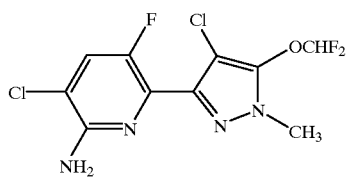

1.84 g of 3-(3-fluoro-5-chloro-6-aminocarbonyl-oxymethyl-2-pyridyl)4chloro-s-difluoromethoxy-1-methyl-[1 H]-pyrazole are initially introduced into 35 ml of N-methylpyrrolidone together with 0.66 g of potassium carbonate. A preheated oilbath of 150° C. is then applied and the mixture is heated overnight at this temperature. The following day, the reaction mixture is cooled to 22° C., poured onto ice-water and then extracted with diethyl ether. The ether phase is washed with brine and dried over sodium sulfate, fiftered and concentrated in vacuo together with twice the amount of silica gel. After application of this silica gel to a flash column, the column is eluted with a mixture of n-hexane/ethyl acetate 1/1. 0.67 g of the desired title compound is obtained as a yellow solid.
TLC analysis: silica gel 60 F₂₅₄; eluting agent: n-hexane/ethyl acetate 1/1: Rf value of the product: 0.33.

Example H51
3-(3-Fluoro-5-chloro-6-isopropylthio-2-pyridyl)-4-chloro-5difluoromethoxy-1-methyl-[1H]-pyrazole (Compound No. I$_1$.088)

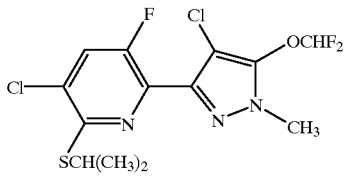

0.79 g 3-(3-fluoro-5-chloro-2-pyridyl-N-oxide)-4-chloro-5-difluoromethoxy-1-methyl-[1H]-pyrazole (Example H19) is initially introduced into 15 ml of benzene. Half of the benzene is distilled off. The mixture is cooled to 5° C. in an ice-bath, while stirring, 0.22 ml of dimethylcarbamoyl chloride is added dropwise and the mixture is subsequently stirred at a temperature below 5° C. for 30 minutes. Cooling in the ice-bath is continued, and 0.67 ml of triethylamine and 0.34 ml of 2-propanethiol are added. The mixture is then stirred overnight, while heating under reflux. After cooling in an ice-bath, 0.15 ml of dimethylcarbamoyl chloride and, 10 minutes later, 0.50 ml of triethylamine and 0.23 ml of 2-propanethiol are added. The mixture is then again boiled at the reflux temperature overnight. After diluting with diethyl ether, the mixture is washed successively with dilute hydrochloric acid, water, dilute sodium bicarbonate solution and brine. After drying over sodium sulfate and filtering, the filtrate is concentrated in vacuo and the residue is purified over a silica gel flash column (eluting agent: toluenelethyl acetate 30/1). 0.22 g of the desired title compound is obtained as a colourless oil, which then crystallizes out (melting point 63–64° C.).

Example H52
3-Fluoro-5-chloro-2-f(2-tert-butoxycarbonyl)-protanoylo-pyridine (Compound No. III$_8$.035)

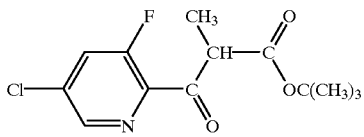

32.3 g of diisopropylamine are initially introduced into 200 ml of tetrahydrofuran, and 200 ml of a 1.6 molar solution of n-butyllithium in hexane are added dropwise, while cooling with a carbon dioxide (CO$_2$)/acetone cooling bath. Thereafter, 49.2 ml of tert-butyl propionate are added dropwise at about −75° C. and the mixture is subsequently stirred at this temperature for 45 minutes. Finally, a solution of 32.6 g of ethyl 3-fluoro-5-chloro-2-pyridinecarboxylate (Example H1) in 40 ml of tetrahydrofuran (THF) is then added dropwise at about −75° C. and the mixture is subsequently stirred at this temperature for 1 hour. Thereafter, the mixture is diluted with 250 ml of tert-butyl methyl ether, and a mixture of 100 ml of water and 200 ml of acetic acid is added. After separation of the phases, the aqueous phase is extracted again with tert-butyl methyl ether and the combined organic phases are then washed with water. After drying over magnesium sulfate, the mixture is filtered and the filtrate is concentrated to dryness in vacuo. 51 g of an oil are obtained as the crude product.

TLC analysis: silica gel 60 F$_{254}$; eluting agent: n-hexane/ethyl acetate 3/1 (UV):
Rf value of the starting material: 0.46;
Rf value of the product: 0.63.

Example H53
3-Fluoro-5-chloro-2-(2-carboxypropanoyl)-pyridine (Compound No. III$_9$.035)

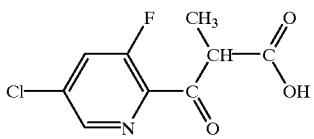

25.5 g of the crude product 3-fluoro-5-chloro-2-[(2-tert-butoxycarbonyl)-propanoyl]-pyridine (Example H52) are added dropwise to 30 ml of a 33% solution of hydrogen bromide (HBr) in glacial acetic acid, a suspension being formed. This suspension is subsequently stirred for 90 minutes. The mixture is then introduced into 300 ml of ice-water and the precipitate formed is filtered off with suction, washed with water and dried. 15.9 g of the desired title compound are obtained as a solid of melting point 101–102° C.

Example H54
3-Fluoro-5chloro-2-(2-chloropropanoyl)-pyridine

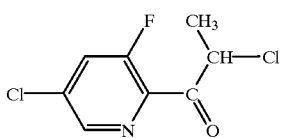

20.8 g of 3-fluoro-5-chloro 2-(2-carboxypropanoyl)-pyridine (Example H53) are initially introduced into 125 ml of glacial acetic acid. 6.3 g of chlorine gas are passed into the solution in the course of 1 hour and the mixture is then poured onto 700 ml of water and extracted with tert-butyl methyl ether. The ether phase is washed with water and dried over magnesium sulfate, filtered and evaporated in vacuo. The resulting crude product is dissolved in 180 ml of tert-butyl methyl ether, and 45 g of silica gel are added. The mixture is stirred for 30 minutes, and initially observed evolution of gas ceasing. The silica gel is then filtered off and rinsed and the combined ether phases are concentrated in vacuo. The resulting crude product (20.1 g of an oil) is purified over a silica gel flash column (eluting agent: n-hexane/ethyl acetate 4/1). 17.0 g of the desired title compound are obtained as a solid of melting point 29–32° C.

Example H55
5-(5-Chloro-3-fluoro-2-pyridyl)-3,6-dimethyl-3,6-dihydro-[1,3,4]-thiadiazine-thione

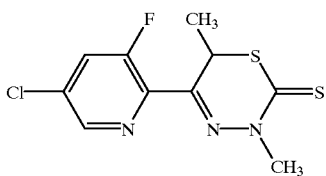

19.1 ml of a 4 molar sodium hydroxide solution and 3.5 g of methylhydrazine are initially introduced into 76 ml of ethanol. 4.5 ml of carbon disulfide are added dropwise whilst stirring at a temperature below 5° C. and the mixture is subsequently stirred for 30 minutes. 17.0 g of 3-fluoro-5-chloro-2-(2-chloropropanoyl)-pyridine (Example H54) are then added in the course of 15 minutes at a temperature below 5° C. Thereafter, the temperature is allowed to rise to 22° C. and the reaction mixture is subsequently stirred for 30 minutes. TLC analysis (silica gel 60 F$_{254}$; eluting agent: n-hexane/ethyl acetate 5/1 (UV)) of a worked-up sample shows that at this point in time no further starting material is present. 2.5 ml of a concentrated hydrochloric acid solution are then added dropwise, a yellow precipitate being formed. The mixture is stirred for 1 hour and then poured onto water and extracted with tert-butyl methyl ether. The ether phase is washed with water, dried over magnesium sulfate, filtered and concentrated in vacuo. 20.3 g of the desired title compound are obtained as a solid of melting point 107–112° C. in this manner.

Example H56
3-(3-Fluoro-5-chloro-2-pyridyl)-4-methyl-5-methylmercapto-1-methyl-[1H]-pyrazole (Compound No. I$_{18}$.002)

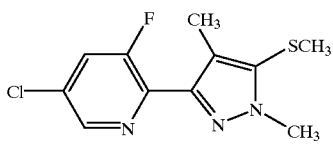

21.6 g of 5-(5-chloro-3-fluoro-2-pyridyl)-3,6-dimethyl-3,6-dihydro-[1,3,4]-thiadiazine-thione (Example H55) are initially introduced into 70 ml of tert-butanol. 19.1 g of triphenylphosphine are then added and the mixture is stirred at a temperature of 65° C. for about 15 minutes, a clear solution being formed. After cooling to 22° C., a suspension is again formed, to which 8.2 g of potassium tert-butylate are added in portions at a temperature below 40° C. (cooling in an ice-bath). The mixture is then subsequently stirred overnight and thereafter poured onto 600 ml of water, stirred, filtered with suction and washed, and the aqueous phase is extracted thoroughly with tert-butyl methyl ether. The aqueous phase is rendered strongly acid with concentrated hydrochloric acid and extracted with tert-butyl methyl ether. The ether phase is washed with water, dried over magnesium sulfate, filtered and concentrated in vacuo. 6.8 g of a crude intermediate are obtained in this manner.

1.9 g of this crude product are dissolved in 10 ml of DMF, and 2.2 g of potassium carbonate are added. Thereafter, 0.5 ml of methyl iodide in 2 ml of DMF is added dropwise under a slightly exothermic reaction. The mixture is then subsequently stirred at 22° C. for 5 hours and thereafter poured onto 120 ml of ice-water and extracted with diethyl ether. The ether phase is washed with water, dried over magnesium sulfate, filtered and concentrated in vacuo. The residue (1.8 g of an oil) is purified over a silica gel flash column (eluting agent: n-hexane/ethyl acetate 2/1. 1.3 g of the desired title compound are obtained as a solid of melting point of 61–64° C.

Example H57
3-(3-Fluoro-5-chloro-2-pyridyl)-4-methyl-5-methylsulfoxy-1-methyl-[1H]-pyrazole and 3-(3-fluoro-5-chloro-2-pyridyl)-4-methyl-5-methylsulfonyl-1-methyl-[1H]-pyrazole (Comp. No. I$_{19}$.002)

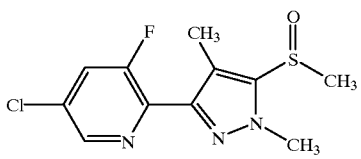

and (Comp. No. I$_{20}$.002)

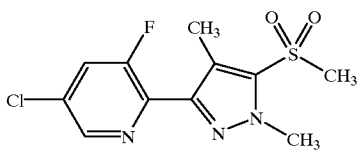

2.1 g of 3-(3-fluoro-5-chloro-2-pyridyl)-4-methyl-5-methylmercapto-1-methyl-[1H]-pyrazole (Example H56) are dissolved in 40 ml of methylene chloride, and a total of 2.84 g of 70% meta-chloroperbenzoic acid are added in portions. The mixture is then stirred at 22° C. for 4 hours. It is subsequently stirred with one molar sodium bicarbonate solution for 30 minutes. The organic phase which has been separated off is washed with water, dried over magnesium sulfate, filtered and concentrated in vacuo. 1.7 g of a solid are obtained, and this is purified over a silica gel flash column (eluting agent: n-hexane/ethyl acetate 1/1). 0.80 g of the desired sulfone of melting point 145–147° C. and 0.70 g of the desired sulfoxide of meting point 112–114° C. are obtained in this manner.

Example H58
3-(3-Fluoro-5chloro-6-(1-hydroxy-2-propyn-3-yl)-2-pyridyl)4-chloro-5-difluoromethoxy-1-methyl-[1H]-pyrazole (Comp. No. I$_1$.190)

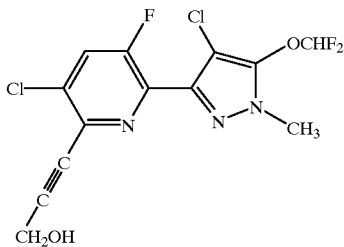

2.0 of 3-(3-fluoro-5,6-dichloro-2-pyridyl)-4-chloro-5difluoromethoxy-1-methyl-[1H]-pyrazole (Example H21) are initially introduced in 15 ml of triethylamine, and 0.37 ml of propargyl alcohol is added. The mixture is then evacuated and gassed with argon 3 times under a partial water pump vacuum. Thereafter, 0.03 g of copper(I) iodide and 0.12 g of bis-triphenylphosphine-palladium dichloride (PdCl$_2$(PPH$_3$)$_2$) are added and the mixture is stirred overnight at 67° C. under argon. The following day, after cooling to 22° C., 0.20 ml of propargyl alcohol, 0.03 g of copper(l) iodide and 0.12 g of PdCl$_2$(PPH$_3$)$_2$ are added. The mixture is then stirred at 67° C. for 6 hours. After cooling to 22° C., ethyl acetate is added and the mixture is washed successively with dilute hydrochloric acid, water and brine. After drying over sodium sulfate, filtration and concentration in vacuo, the residue is purified over a silica gel flash column (eluting agent: n-hexane/ethyl acetate 1/1). 0.97 g of the desired title compound is obtained as a yellow oil which gradually crystallizes; melting point 92–94° C.

Example H59
3-(3-Fluoro-5-chloro-6-(N-propargl-N-ethylsulfonyl)-amino-2-pyridyl)-4-chloro-5-difluoromethoxy-1-methyl-[1H]-pyrazole Comp. No. $I_1.747$

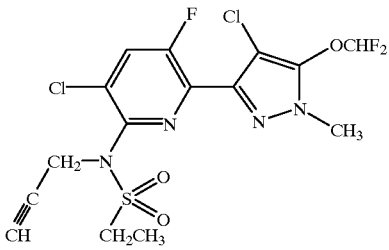

0.81 g of 3-(3-fluoro-5-chloro-6-amino-2-pyridyl)-4-chloro-5-difluoromethoxy-1-methyl-[1H]-pyrazole (Example H50) is dissolved in 10 ml of methylene chloride. 0.93 ml of triethylamine and then 0.54 ml of ethanesulfonyl chloride ($CH_3CH_2SO_2Cl$) are added, while stirring and cooling in an ice-bath, and the mixture is subsequently stirred at 22° C. for 48 hours. Diethyl ether is added to the reaction mixture and the mixture is washed with dilute hydrochloric acid and then with brine. After drying over sodium sulfate, filtering and concentrating in vacuo, 1.0 g of an intermediate product is obtained, and this is dissolved in 10 ml of dioxane. 2.0 ml of a 2 molar aqueous sodium hydroxide solution are added dropwise, while cooling in an ice-bath and stirring, and the mixture is subsequently stirred at 22° C. for 1.5 hours. It is then diluted with diethyl ether and rendered acid with hydrochloric acid. After extraction by shaking and separation of the phases, the ether phase is washed with brine, dried over sodium sulfate, filtered and concentrated in vacuo. The intermediate obtained in this manner is dissolved in 20 ml of N-methylpyrrolidone (NMP) and the solution is stirred and cooled in an ice-bath. 2.0 g of potassium carbonate are then added, and 0.45 ml of propargyl bromide is added dropwise. The mixture is subsequently stirred, with the ice-bath thawing, and is then partitioned between ice-water and diethyl ether. After extraction by shaking and separation of the phases, the ether phase is washed with brine, dried over sodium sulfate, fiftered and concentrated in vacuo together with twice the amount of silica gel. After application of the silica gel to a flash column, the column is eluted with n-hexane/ethyl acetate 2/1. 0.34 g of the desired title compound is obtained as a brown-yellow solid of melting point 138–139° C.

Example H60
3-(3-Fluoro-5-chloro-6-carbamoylmethylenoxy-2-pyridyl)-4-chloro-5-difluoromethoxy-1-methyl-[1H]-pyrazole (Comp. No. $I_1.061$)

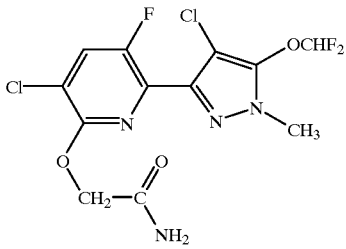

3.0 g of 3-(3-fluoro-5-chloro-6-hydroxy-2-pyridyl)-4-chloro-5-difluoromethoxy-1-methyl-[1H]-pyrazole (Example H30) are initially introduced into 30 ml of N-methylpyrrolidone (NMP) together with 2.53 g of potassium carbonate, and 0.96 g of chloroacetamide is then added. The mixture is stirred overnight at 50° C. After cooling to 22° C., it is then poured onto ice-water and a little diethyl ether is added. The slurry formed is filtered with suction and the solid is washed successively with water, diethyl ether and n-hexane. After drying in vacuo at 50° C., 2.35 g of the desired title compound are isolated as a beige solid.

$^1$H-NMR ($CDCl_3$): 7.64 ppm (d, 1H); 6.72 ppm (t, 1H); 6.50 ppm (broad, 1H); 5.60 ppm (broad, 1H); 4.6 ppm (s, 2H); 3.87 ppm (s, 3H).

Example H61
3-(3-Fluoro-5-chloro-2-pyridyl)-5-(2.2.2-trifluoroethoxy)-1-methyl-[1H]-pyrazole Comp. No. $I_{132}.035$

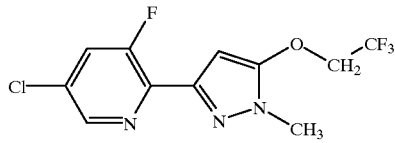

3.0 g of 3-(3-fluoro-5-chloro-2-pyridyl)-5-hydroxy-1-methyl-[1H]-pyrazole (Example H14) are initially introduced into 30 ml of N-methylpyrrolidone (NMP) together with 3.64 g of potassium carbonate, and 3.49 g of 2,2,2-trifluoro-ethanol 4-methylbenzenesulfonate are added. 0.3 g of sodium iodide is then added and the mixture is stirred overnight at 80° C. It is then cooled to 22° C. and partitioned between dilute hydrochloric acid and diethyl ether. After extraction by shaking and separation of the phases, the ether phase is washed with brine, filtered and concentrated in vacuo together with twice the amount of silica gel. After application of the silica gel to a flash column, the column is eluted with n-hexane/ethyl acetate 2/1. 2.68 g of the desired title compound are obtained as a yellow solid of melting point 72–73° C.

The compounds listed in the following tables can also be prepared in an analogous manner.

In the following tables 1 to 4, certain structures $I_n$, $II_1$–$II_{13}$, $III_1$–$III_9$, $IV_1$, $IV_2$, $V_1$ or $V_2$, for example $I_n$ to $I_{34}$ in Table 1 or $I_{107}$ to $I136$; $I_{149}$–$I_{156}$; $II_1$–$II_{13}$; $III_1$–$III_9$; $IV_1$, $IV_2$; $V_1$ and $V_2$ in Table 4, with the same substituent variations, for example $R_{11}$ and $R_{13}$ in Table 1 or $R_{11}$, $R_{12}$ and $R_{13}$ in Table 4, are combined for simplification.

In the tables mentioned, all the structures $I_n$ or $II_1$–$II_{12}$, $III_1$–$III_9$, $IV_1$, $IV_2$, $V_1$ or $V_2$, where for Table 1 n=1 to 34, mentioned in the heading of the tables should thus be combined with the definitions given in the tables. For example, in Table 1, $I_n.001$ discloses each of the 34 specific compounds $I_1.001$, $I_2.001$, $I_3.001$, $I_4.001$, $I_5.001$, $I_6.001$, $I_7.001$, $I_8.001$ and so on up to $I_{34}.001$, in which in each case $R_{11}$ and $R_{13}$ are fluorine.

TABLE 1
Compounds of the formulae I₁ to I₃₄
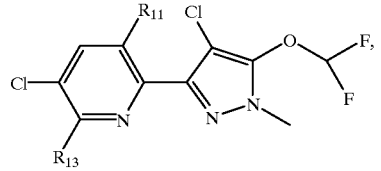 (I₁)
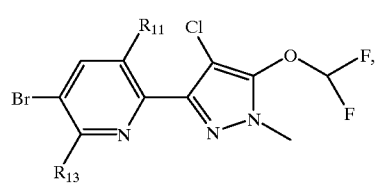 (I₂)
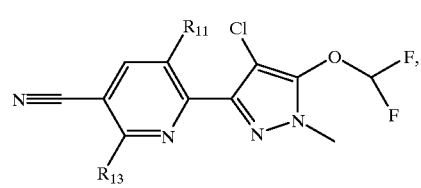 (I₃)
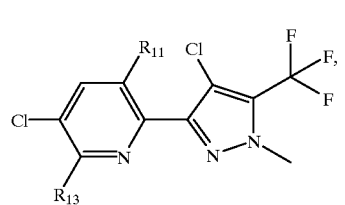 (I₄)
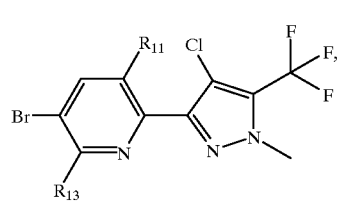 (I₅)
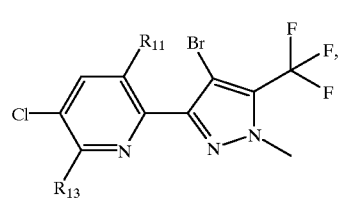 (I₆)
TABLE 1-continued
Compounds of the formulae I₁ to I₃₄
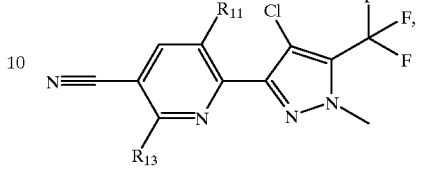 (I₇)
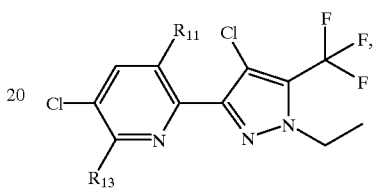 (I₈)
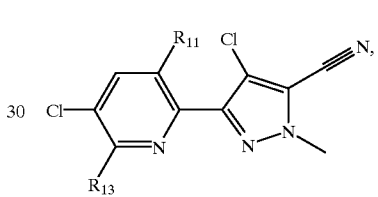 (I₉)
(I₁₀)
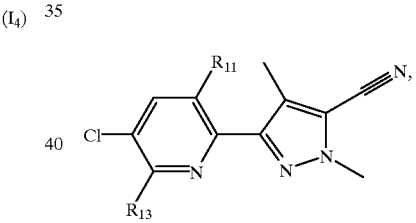 (I₁₁)
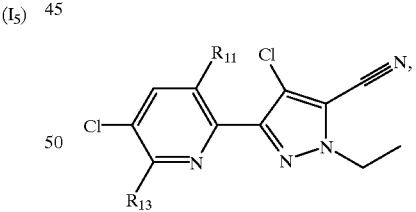 (I₁₂)

TABLE 1-continued
Compounds of the formulae $I_1$ to $I_{34}$
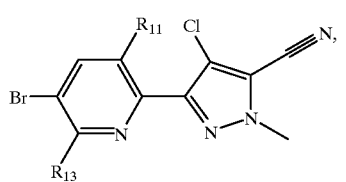
($I_{13}$)
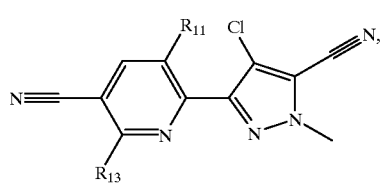
($I_{14}$)
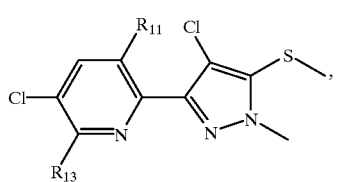
($I_{15}$)
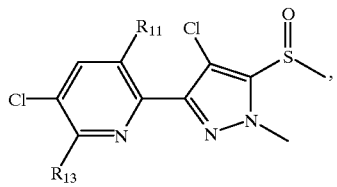
($I_{16}$)
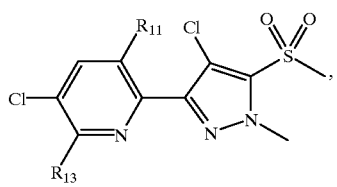
($I_{17}$)
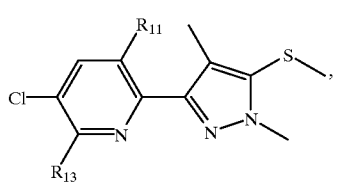
($I_{18}$)
TABLE 1-continued
Compounds of the formulae $I_1$ to $I_{34}$
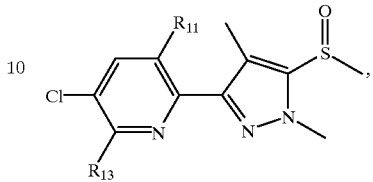
($I_{19}$)
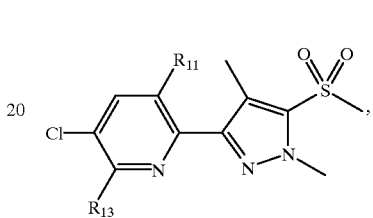
($I_{20}$)
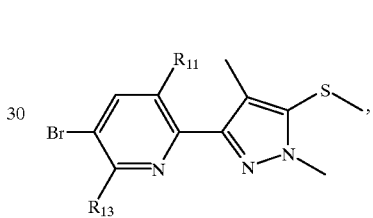
($I_{21}$)
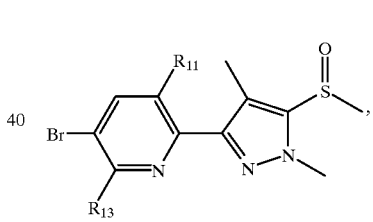
($I_{22}$)
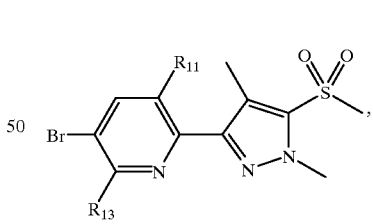
($I_{23}$)
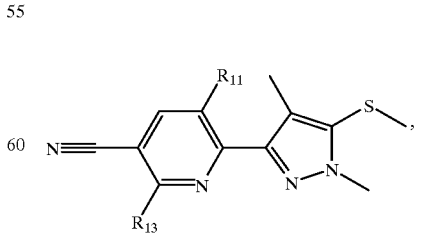
($I_{24}$)

TABLE 1-continued

Compounds of the formulae I₁ to I₃₄

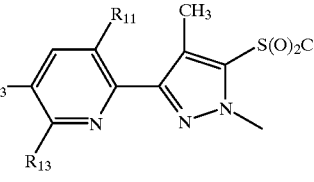

| Comp. No. I_n n = 1–34 | R₁₁ | R₁₃ |
|---|---|---|
| 001 | F | F |
| 002 | F | H |
| 003 | F | Cl |
| 004 | F | NH₂ |
| 005 | F | OH |
| 006 | F | SH |
| 007 | F | Br |
| 008 | F | I |
| 009 | F | CN |
| 010 | F | SO₂Cl |
| 011 | F | NH(CH₃) |
| 012 | F | N(CH₂CH₃)₂ |
| 013 | F | NH(COCH₃) |
| 014 | F | NH(CH₂CH=CH₂) |
| 015 | F | N(CH₃)(CH₂C≡CH) |
| 016 | F | N(SO₂CH₃)₂ |
| 017 | F | NH(SO₂CH₂CH₃) |
| 018 | F | N(CH₂CH=CH₂)(SO₂CH₂CH₃) |
| 019 | F | N(CH₂C≡CH)(SO₂CH(CH₃)₂) |
| 020 | F | N(CH₂CF₃)(CHO) |
| 021 | F | NH(CH₂C₆H₅) |
| 022 | F | OCH₃ |
| 023 | F | OCH₂CH₃ |
| 024 | F | OCH(CH₃)₂ |
| 025 | F | OCH(CH₃)CH₂CH₂CH₃ |
| 026 | F | OCH₂CH=CH₂ |
| 027 | F | OCH(CH₃)CH=CH₂ |
| 028 | F | OCH₂C≡CH |
| 029 | F | OCH(CH₃)C≡CH |
| 030 | F | OCH(cyclopentyl)₂ |
| 031 | F | OCH₂(C₆H₅) |
| 032 | F | OCH₂(2-F—C₆H₅) |
| 033 | F | OCH(CH₃)(4-CH₃—C₆H₅) |
| 034 | F | OC₆H₅ |
| 035 | F | O(4-pyrimidyl) |
| 036 | F | OCH₂CH₂Cl |
| 037 | F | OCH₂CH=CHCl |
| 038 | F | OCH₂CH₂OH |
| 039 | F | OCH₂OCH₃ |

TABLE 1-continued

Compounds of the formulae $I_1$ to $I_{34}$

| | | |
|---|---|---|
| 040 | F | $OCH_2CH_2OCH_2CH_3$ |
| 041 | F | $OCH_2CH_2OCH_2CH_2OCH_2CH_3$ |
| 042 | F | $OCH(CH_3)CH_2OCH_2CH=CH_2$ |
| 043 | F | $OCOCH_3$ |
| 044 | F | $OCOOCH_3$ |
| 045 | F | $OCOCH_2C_6H_5$ |
| 046 | F | $OCH_2SCH_3$ |
| 047 | F | $OCH_2CH_2SCH_2CH_3$ |
| 048 | F | $OCH_2COOH$ |
| 049 | F | $OCH(CH_3)COOH$ |
| 050 | F | $(R)-OCH(CH_3)COOH$ |
| 051 | F | $(S)-OCH(CH_3)COOH$ |
| 052 | F | $OCH_2COOCH_2CH_3$ |
| 053 | F | $OCH(CH_3)COOCH_3$ |
| 054 | F | $OCH(CH_3)COOCH_2CH=CH_2$ |
| 055 | F | $OCH(CH_3)COOCH_2(C_6H_5)$ |
| 056 | F | $OCH(CH_3)CH_2COOH$ |
| 057 | F | $OCH(CH_3)CH_2COOCH_2CH_3$ |
| 058 | F | $OCH_2COSCH_3$ |
| 059 | F | $OCH(CH_3)COSCH_2CH_3$ |
| 060 | F | $OCH(CH_3)COSCH(CH_3)_2$ |
| 061 | F | $OCH_2CONH_2$ |
| 062 | F | $OCH_2CON(CH_2CH_3)_2$ |
| 063 | F | $OCH(CH_3)CON(CH_3)_2$ |
| 064 | F | $OCH(CH_3)CONH(CH_2CH=CH_2)$ |
| 065 | F | $OCH(CH_3)CON(CH_3)(CH_2C\equiv CH)$ |
| 066 | F | $OCH(CH_3)CON(CH_2C_6H_5)_2$ |
| 067 | F | $OCH(CH_3)CON(CH_3)(C_6H_5)$ |
| 068 | F | $OCH_2COOCH_2CH_2SCH_3$ |
| 069 | F | $OCH(CH(CH_3)_2)COOH$ |
| 070 | F | $OCH(CH_3)COOCH_2CH_2OCH_2CH_3$ |
| 071 | F | $OCH(C_6H_5)COOH$ |
| 072 | F | $(R)-OCH(C_6H_5)COOH$ |
| 073 | F | $(S)-OCH(C_6H_5)COOH$ |
| 074 | F | $OCH(C_6H_5)COOCH_3$ |
| 075 | F | $OCH(C_6H_5)COOCH(CH_3)C\equiv CH$ |
| 076 | F | $OCH(C_6H_5)COOCH_2C_6H_5$ |
| 077 | F | $OCH(C_6H_5)COSCH(CH_3)_2$ |
| 078 | F | $OCH(C_6H_5)CONH_2$ |
| 079 | F | $OCH(C_6H_5)CONH(CH_2C\equiv CH)$ |
| 080 | F | $OCH(C_6H_5)CON(CH_2CH=CH_2)_2$ |
| 081 | F | $OCH(C_6H_5)CON(CH_3)CH_2C_6H_5$ |
| 082 | F | $OCH(C_6H_5)CONH(CH_2(2\text{-}F-C_6H_5))$ |
| 083 | F | $OCH(C_6H_5)CONH(\text{cyclopropyl})$ |
| 084 | F | $OCH_2CH_2COOH$ |
| 085 | F | $OCH_2CH_2COOCH_2CH_3$ |
| 086 | F | $OCH(CH_3)CH_2COOH$ |
| 087 | F | $SCH_3$ |
| 088 | F | $SCH(CH_3)_2$ |
| 089 | F | $SCH_2CH=CH_2$ |
| 090 | F | $SCH_2C_6H_5$ |
| 091 | F | $SCH_2CH_2OCH_3$ |
| 092 | F | $SC_6H_5$ |
| 093 | F | $SCH_2COOH$ |
| 094 | F | $SCH_2COOCH_2C_6H_5$ |
| 095 | F | $SCH(CH_3)COOH$ |
| 096 | F | $SCH(CH_3)COOCH_2CH_3$ |
| 097 | F | $SCH(CH_3)COOCH_2CH=CH_2$ |
| 098 | F | $SCH(CH_3)COSCH_3$ |
| 099 | F | $SCH(CH_3)CON(CH_3)_2$ |
| 100 | F | $SCH(CH_3)CONH(CH_2CH=CH_2)$ |
| 101 | F | $SOCH_2CH_3$ |
| 102 | F | $SO_2CH_3$ |
| 103 | F | $SO_2NH_2$ |
| 104 | F | $SO_2N(CH_3)_2$ |
| 105 | F | $SO_2N(CH_2CH_3)_2$ |
| 106 | F | $SO_2N(CH_3)(CH_2(4\text{-}CH_3-C_6H_5)$ |
| 107 | F | $SO_2NHCH_2CH_2OCH_3$ |
| 108 | F | $SCOOCH_3$ |
| 109 | F | $SCON(CH_3)_2$ |
| 110 | F | $SCONHCH_2CH=CH_2$ |
| 111 | F | $SCOOCH_2CHCH_2$ |
| 112 | F | $SCON(CH_2CH_3)COCF_3$ |
| 113 | F | $CHO$ |
| 114 | F | $COCH_3$ |
| 115 | F | $COOCH_2CH_3$ |
| 116 | F | $COOCH_2C_6H_5$ |
| 117 | F | $COCl$ |
| 118 | F | $COCH_2CH_2Cl$ |
| 119 | F | $COOH$ |
| 120 | F | $COOCH_3$ |
| 121 | F | $COOCH_2CH_3$ |
| 122 | F | $COOCH(CH_3)_2$ |
| 123 | F | $COOCH_2CH=CH_2$ |
| 124 | F | $COO(CH_2)_5CH_3$ |
| 125 | F | $COOCH(CH_3)CH=CH_2$ |
| 126 | F | $COOCH_2(2\text{-}F-C_6H_5)$ |
| 127 | F | $COOC_6H_5$ |
| 128 | F | $COOCH_2CH_2OCH_2CH_3$ |
| 129 | F | $COOCH(CH_3)CH_2SCH_3$ |
| 130 | F | $COO(\text{oxetanyl})$ |
| 131 | F | $COOCH_2(\text{oxiranyl})$ |
| 132 | F | $COO(\text{cylopentyl})$ |
| 133 | F | $COSCH_3$ |
| 134 | F | $COSCH(CH_3)_2$ |
| 135 | F | $COSCH_2C_6H_5$ |
| 136 | F | $CONH_2$ |
| 137 | F | $CONH(CH_2CH=CH_2)$ |
| 138 | F | $CONHCH_2C_6H_5$ |
| 139 | F | $CON(CH_2CH=CH_2)_2$ |
| 140 | F | $CON(CH_3)OCH_3$ |
| 141 | F | $COOCH_2CH_2COOH$ |
| 142 | F | $COOCH(CH_3)COOCH_3$ |
| 143 | F | $COOCH(CH_3)COOCH_2C_6H_5$ |
| 144 | F | $COOCH(CH_3)CH_2COOCH_2CH_3$ |
| 145 | F | $(S)-COOCH(CH_3)CH_2COOCH_2CH=CH_2$ |
| 146 | F | $(R)-COOCH(CH_3)CH_2COOCH_2CH=CH_2$ |
| 147 | F | $COOCH(CH_3)CH_2CONHCH_2CH_3$ |
| 148 | F | $COOCH(CH_3)CH_2CON(CH_3)_2$ |
| 149 | F | $COOCH(CH_3)CH_2COSCH_2CH_3$ |
| 150 | F | $COOCH(CH_3)CH_2COOCH_2CH=CH_2$ |
| 151 | F | $COOC(CH_3)_2COCH_3$ |
| 152 | F | $COOC(CH_3)_2COOH$ |
| 153 | F | $COOC(CH_3)_2COOCH_3$ |
| 154 | F | $COOC(CH_3)_2COOCH_2CH_3$ |
| 155 | F | $COOC(CH_3)_2COOCH(CH_3)_2$ |
| 156 | F | $COOC(CH_3)_2COO(CH_2)_4CH_3$ |
| 157 | F | $COOC(CH_3)_2COOCH_2C_6H_5$ |
| 158 | F | $COOC(CH_3)_2COOCH_2(2\text{-}F-C_6H_5)$ |
| 159 | F | $COOC(CH_3)_2COOCH_2CH=CH_2$ |
| 160 | F | $COOC(CH_3)_2COOCH(CH_3)CH=CH_2$ |
| 161 | F | $COOC(CH_3)_2COOCH_2C\equiv CH$ |
| 162 | F | $COO(CH_3)_2COOCH_2CH_2OCH_2CH_3$ |
| 163 | F | $COOC(CH_3)_2COSCH_3$ |
| 164 | F | $COOC(CH_3)_2COSCH(CH_3)_2$ |
| 165 | F | $COOC(CH_3)_2COSCH_2C_6H_5$ |
| 168 | F | $COOC(CH_3)_2CONH_2$ |
| 167 | F | $COOC(CH_3)_2CONHCH_2CH=CH_2$ |
| 168 | F | $COOC(CH_3)_2CON(CH_2CH_3)_2$ |
| 169 | F | $COOC(CH_3)_2CON(CH_3)CH_2CH_2OCH_3$ |
| 170 | F | $COSCH(CH_3)COOH$ |
| 171 | F | $COSCH(CH_3)COOCH_3$ |
| 172 | F | $COSCH(CH_3)CONHCH_2CH=CH_2$ |
| 173 | F | $CON(CH_3)CH_2COOH$ |
| 174 | F | $CON(CH_3)C(CH_3)_2COOCH_2CH_3$ |
| 175 | F | $CON(CH_3)OCH_2COOCH_3$ |
| 176 | F | $CON(CH_3)OH$ |
| 177 | F | $CH_3$ |
| 178 | F | $CH_2CH_3$ |
| 179 | F | $CH(OH)CH_3$ |
| 180 | F | $CH(OCH_2CH=CH_2)CH_3$ |
| 181 | F | $CH_2Cl$ |
| 182 | F | $CH_2OH$ |
| 183 | F | $CH_2OCOCH_3$ |
| 184 | F | $CHClCH_3$ |
| 185 | F | $CH_2CH_2CF_3$ |
| 186 | F | $CH=CHCF_3$ |
| 187 | F | $OH_2CH=CH_2$ |
| 188 | F | $CH=CHCH_3$ |
| 189 | F | $C\equiv CH$ |
| 190 | F | $CCCH_2OH$ |
| 191 | F | $CH_2CHClCOOH$ |
| 192 | F | $(R)-CH_2CHClCOOH$ |
| 193 | F | $(S)-CH_2CHClCOOH$ |

TABLE 1-continued

Compounds of the formulae $I_1$ to $I_{34}$

| | | |
|---|---|---|
| 194 | F | CH$_2$CH(CH$_3$)COOH |
| 195 | F | CH$_2$CH(CH$_3$)COOCH$_2$CH$_3$ |
| 196 | F | CH(Cl)CH$_2$COOCH$_3$ |
| 197 | F | CH(Cl)C(Cl)$_2$COOH |
| 198 | F | CH(Cl)CH(Cl)COOCH$_2$CH$_3$ |
| 199 | F | CH$_2$CH(CH$_3$)COOH |
| 200 | F | CH$_2$CH(CH$_3$)COCH$_2$CH=CH$_2$ |
| 201 | F | CH$_2$CH(CH$_3$)CONH(CH$_2$CH=CH$_2$) |
| 202 | F | CH$_2$CH(CH$_3$)CON(CH$_3$)$_2$ |
| 203 | F | CH$_2$CH(CH$_3$)COSCH(CH$_3$)$_2$ |
| 204 | F | CH$_2$CHClCOOC(CH$_3$)$_3$ |
| 205 | F | CH$_2$CHClCOOCH$_3$ |
| 206 | F | CH$_2$CHClCOOCH$_2$CH$_3$ |
| 207 | F | CH$_2$CHClCOOCH(CH$_3$)$_2$ |
| 208 | F | CH$_2$CHClCOOCH$_2$CH=CH$_2$ |
| 209 | F | CH$_2$CHClCOOCH$_2$C$_6$H$_5$ |
| 210 | F | CH$_2$CHClCOSCH$_3$ |
| 211 | F | CH$_2$CHClCOSCH(CH$_3$)$_2$ |
| 212 | F | CH$_2$CHClCOSCH$_2$C$_6$H$_5$) |
| 213 | F | CH$_2$CHClCONH$_2$ |
| 214 | F | CH$_2$CHClCONH(CH$_2$CH=CH$_2$) |
| 215 | F | CH$_2$CHClCON(CH$_2$CH$_3$)$_2$ |
| 216 | F | CH$_2$CHClCONH(CH$_2$C$_6$H$_5$) |
| 217 | F | CH$_2$CHClCON(CH$_3$)CH$_2$C$_6$H$_5$ |
| 218 | F | CH=CHCOOH |
| 219 | F | (E)-CH=CHCOOH |
| 220 | F | (Z)-CH=CHCOOH |
| 221 | F | CH=CHCOOCH$_3$ |
| 222 | F | CH=CHCOOCH$_2$C$_6$H$_5$ |
| 223 | F | CH=CHCONH$_2$ |
| 224 | F | CH=CHCONH(CH$_2$CH=CH$_2$) |
| 225 | F | CH=C(Cl)COOH |
| 226 | F | CH=C(Cl)CONH$_2$ |
| 227 | F | CH=C(Cl)CONH(CH$_2$CH$_3$) |
| 228 | F | CH=C(Cl)CON(CH$_2$CH$_3$)$_2$ |
| 229 | F | CH=C(Cl)CONH(CH$_2$C$_6$H$_5$) |
| 230 | F | CH=C(Cl)COSCH$_3$ |
| 231 | F | CH=C(Cl)COSCH(CH$_3$)$_2$ |
| 232 | F | CH=C(CH$_3$)COOH |
| 233 | F | CH=C(CH$_3$)CONH(CH$_2$CH=CH$_2$) |
| 234 | F | CH=C(CH$_3$)CON(CH$_3$)$_2$ |
| 235 | F | CH=C(CH$_3$)COSCH$_2$CH$_3$ |
| 236 | F | CH=C(CN)COOH |
| 237 | F | CH=C(CN)COOC(CH$_3$)$_3$ |
| 238 | F | CH=C(CN)CON(CH$_2$CH=CH$_2$)$_2$ |
| 239 | F | CH=C(COOH)$_2$ |
| 240 | F | CH=C(C$_6$H$_5$)COOH |
| 241 | F | CH=CHCH$_2$OH |
| 242 | Cl | F |
| 243 | Cl | H |
| 244 | Cl | Cl |
| 245 | Cl | NH$_2$ |
| 246 | Cl | OH |
| 247 | Cl | SH |
| 248 | Cl | Br |
| 249 | Cl | I |
| 250 | Cl | CN |
| 251 | Cl | SO$_2$Cl |
| 252 | Cl | NH(CH$_3$) |
| 253 | Cl | N(CH$_2$CH$_3$)$_2$ |
| 254 | Cl | NH(COCH$_3$) |
| 255 | Cl | NH(CH$_2$CH=CH$_2$) |
| 256 | Cl | N(CH$_3$)(CH$_2$C≡CH) |
| 257 | Cl | N(SO$_2$CH$_3$)$_2$ |
| 258 | Cl | NH(SO$_2$CH$_2$CH$_3$) |
| 259 | Cl | N(CH$_2$CH=CH$_2$)(SO$_2$CH$_2$CH$_3$) |
| 260 | Cl | N(CH$_2$C≡CH)(SO$_2$CH(CH$_3$)$_2$) |
| 261 | Cl | N(CH$_2$CF$_3$)(CHO) |
| 262 | Cl | NH(CH$_2$C$_6$H$_5$) |
| 263 | Cl | OCH$_3$ |
| 264 | Cl | OCH$_2$CH$_3$ |
| 265 | Cl | OCH(CH$_3$)$_2$ |
| 266 | Cl | OCH(CH$_3$)CH$_2$CH$_2$CH$_3$ |
| 267 | Cl | OCH$_2$CH=CH$_2$ |
| 268 | Cl | OCH(CH$_3$)CH=CH$_2$ |
| 269 | Cl | OCH$_2$C≡CH |
| 270 | Cl | OCH(CH$_3$)C≡CH |
| 271 | Cl | OCH(cyclopentyl) |
| 272 | Cl | OCH$_2$(C$_6$H$_5$) |
| 273 | Cl | OCH$_2$(2-F—C$_6$H$_5$) |
| 274 | Cl | OCH(CH$_3$)(4-CH$_3$—C$_6$H$_5$) |
| 275 | Cl | OC$_6$H$_5$ |
| 276 | Cl | O(4-pyrimidyl) |
| 277 | Cl | OCH$_2$CH$_2$Cl |
| 278 | Cl | OCH$_2$CH=CHCl |
| 279 | Cl | OCH$_2$CH$_2$OH |
| 280 | Cl | OCH$_2$OCH$_3$ |
| 281 | Cl | OCH$_2$CH$_2$OCH$_2$CH$_3$ |
| 282 | Cl | OCH$_2$CH$_2$OCH$_2$CH$_2$OCH$_2$CH$_3$ |
| 283 | Cl | OCH(CH$_3$)CH$_2$OCH$_2$CH=CH$_2$ |
| 284 | Cl | OCOCH$_3$ |
| 285 | Cl | OCOOCH$_3$ |
| 286 | Cl | OCOCH$_2$C$_6$H$_5$ |
| 287 | Cl | OCH$_2$SCH$_3$ |
| 288 | Cl | OCH$_2$CH$_2$SCH$_2$CH$_3$ |
| 289 | Cl | OCH$_2$COOH |
| 290 | Cl | OCH(CH$_3$)COOH |
| 291 | Cl | (R)—OCH(CH$_3$)COOH |
| 292 | Cl | (S)—OCH(CH$_3$)COOH |
| 293 | Cl | OCH$_2$COOCH$_2$CH$_3$ |
| 294 | Cl | OCH(CH$_3$)COOCH$_3$ |
| 295 | Cl | OCH(CH$_3$)COOCH$_2$CH=CH$_2$ |
| 296 | Cl | OCH(CH$_3$)COOCH$_2$(C$_6$H$_5$) |
| 297 | Cl | OCH(CH$_3$)CH$_2$COOH |
| 298 | Cl | OCH(CH$_3$)CH$_2$COOCH$_2$CH$_3$ |
| 299 | Cl | OCH$_2$COSCH$_3$ |
| 300 | Cl | OCH(CH$_3$)COSCH$_2$CH$_3$ |
| 301 | Cl | OCH(CH$_3$)COSCH(CH$_3$)$_2$ |
| 302 | Cl | OCH$_2$CONH$_2$ |
| 303 | Cl | OCH$_2$CON(CH$_2$CH$_3$)$_2$ |
| 304 | Cl | OCH(CH$_3$)CON(CH$_3$)$_2$ |
| 305 | Cl | OCH(CH$_3$)CONH(CH$_2$CH=CH$_2$) |
| 306 | Cl | OCH(CH$_3$)CON(CH$_3$)(CH$_2$C≡CH) |
| 307 | Cl | OCH(CH$_3$)CON(CH$_2$C$_6$H$_5$)$_2$ |
| 308 | Cl | OCH(CH$_3$)CON(CH$_3$)(C$_6$H$_5$) |
| 309 | Cl | OCH$_2$COOCH$_2$CH$_2$SCH$_3$ |
| 310 | Cl | OCH(CH(CH$_3$)$_2$)COOH |
| 311 | Cl | OCH(CH$_3$)COOCH$_2$CH$_2$OCH$_2$CH$_3$ |
| 312 | Cl | OCH(C$_6$H$_5$)COOH |
| 313 | Cl | (R)—OCH(C$_6$H$_5$)COOH |
| 314 | Cl | (S)—OCH(C$_6$H$_5$)COOH |
| 315 | Cl | OCH(C$_6$H$_5$)COOCH$_3$ |
| 316 | Cl | OCH(C$_6$H$_5$)COOCH(CH$_3$)C≡CH |
| 317 | Cl | OCH(C$_6$H$_5$)COOCH$_2$C$_6$H$_5$ |
| 318 | Cl | OCH(C$_6$H$_5$)COSCH(CH$_3$)$_2$ |
| 319 | Cl | OCH(C$_6$H$_5$)CONH$_2$ |
| 320 | Cl | OCH(C$_6$H$_5$)CONH(CH$_2$C≡CH) |
| 321 | Cl | OCH(C$_6$H$_5$)CON(CH$_2$CH=CH$_2$)$_2$ |
| 322 | Cl | OCH(C$_6$H$_5$)CON(CH$_3$)CH$_2$C$_6$H$_5$ |
| 323 | Cl | OCH(C$_6$H$_5$)CONH(CH$_2$(2-F—C$_6$H$_5$)) |
| 324 | Cl | OCH(C$_6$H$_5$)CONH(cyclopropyl) |
| 325 | Cl | OCH$_2$CH$_2$COOH |
| 326 | Cl | OCH$_2$CH$_2$COOCH$_2$CH$_3$ |
| 327 | Cl | OCH(CH$_3$)CH$_2$COOH |
| 328 | Cl | SCH$_3$ |
| 329 | Cl | SCH(CH$_3$)$_2$ |
| 330 | Cl | SCH$_2$CH=CH$_2$ |
| 331 | Cl | SCH$_2$C$_6$H$_5$ |
| 332 | Cl | SCH$_2$CH$_2$OCH$_3$ |
| 333 | Cl | SC$_6$H$_5$ |
| 334 | Cl | SCH$_2$COOH |
| 335 | Cl | SCH$_2$COOCH$_2$C$_6$H$_5$ |
| 336 | Cl | SCH(CH$_3$)COOH |
| 337 | Cl | SCH(CH$_3$)COOCH$_2$CH$_3$ |
| 338 | Cl | SCH(CH$_3$)COOCH$_2$CH=CH$_2$ |
| 339 | Cl | SCH(CH$_3$)COSCH$_3$ |
| 340 | Cl | SCH(CH$_3$)CON(CH$_3$)$_2$ |
| 341 | Cl | SCH(CH$_3$)CONH(CH$_2$CH=CH$_2$) |
| 342 | Cl | SOCH$_2$CH$_3$ |
| 343 | Cl | SO$_2$CH$_3$ |
| 344 | Cl | SO$_2$NH$_2$ |
| 345 | Cl | SO$_2$N(CH$_3$)$_2$ |
| 346 | Cl | SO$_2$N(CH$_2$CH$_3$)$_2$ |
| 347 | Cl | SO$_2$N(CH$_3$)(CH$_2$(4-CH$_3$—C$_6$H$_5$) |

TABLE 1-continued

Compounds of the formulae $I_1$ to $I_{34}$

| | | |
|---|---|---|
| 348 | Cl | SO$_2$NHCH$_2$CH$_2$OCH$_3$ |
| 349 | Cl | SCOOCH$_3$ |
| 350 | Cl | SCON(CH$_3$)$_2$ |
| 351 | Cl | SCONHCH$_2$CH=CH$_2$ |
| 352 | Cl | SCOOCH$_2$CH=CH$_2$ |
| 353 | Cl | SCON(CH$_2$CH$_3$)COCF$_3$ |
| 354 | Cl | CHO |
| 355 | Cl | COCH$_3$ |
| 356 | Cl | COOCH$_2$CH$_3$ |
| 357 | Cl | COOCH$_2$C$_6$H$_5$ |
| 358 | Cl | COCl |
| 359 | Cl | COCH$_2$CH$_2$Cl |
| 360 | Cl | COOH |
| 361 | Cl | COOCH$_3$ |
| 362 | Cl | COOCH$_2$CH$_3$ |
| 363 | Cl | COOCH(CH$_3$)$_2$ |
| 364 | Cl | COOCH$_2$CH=CH$_2$ |
| 365 | Cl | COO(CH$_2$)$_5$CH$_3$ |
| 366 | Cl | COOCH(CH$_3$)CH=CH$_2$ |
| 367 | Cl | COOCH$_2$(2-F—C$_6$H$_5$) |
| 368 | Cl | COOC$_6$H$_5$ |
| 369 | Cl | COOCH$_2$CH$_2$OCH$_2$CH$_3$ |
| 370 | Cl | COOCH(CH$_3$)CH$_2$SCH$_3$ |
| 371 | Cl | COO(oxetanyl) |
| 372 | Cl | COOCH$_2$(oxiranyl) |
| 373 | Cl | COO(cylopentyl) |
| 374 | Cl | COSCH$_3$ |
| 375 | Cl | COSCH(CH$_3$)$_2$ |
| 376 | Cl | COSCH$_2$C$_6$H$_5$ |
| 377 | Cl | CONH$_2$ |
| 378 | Cl | CONH(CH$_2$CH=CH$_2$) |
| 379 | Cl | CONHCH$_2$C$_6$H$_5$ |
| 380 | Cl | CON(CH$_2$CH=CH$_2$)$_2$ |
| 381 | Cl | CON(CH$_3$)OCH$_3$ |
| 382 | Cl | COOCH$_2$CH$_2$COOH |
| 383 | Cl | COOCH(CH$_3$)COOCH$_3$ |
| 384 | Cl | COOCH(CH$_3$)COOCH$_2$C$_6$H$_5$ |
| 385 | Cl | COOCH(CH$_3$)CH$_2$COOCH$_2$CH$_3$ |
| 386 | Cl | (S)—COOCH(CH$_3$)CH$_2$COOCH$_2$CH=CH$_2$ |
| 387 | Cl | (R)—COOCH(CH$_3$)CH$_2$COOCH$_2$CH=CH$_2$ |
| 388 | Cl | COOCH(CH$_3$)CH$_2$CONHCH$_2$CH$_3$ |
| 389 | Cl | COOCH(CH$_3$)CH$_2$CON(CH$_3$)$_2$ |
| 390 | Cl | COOCH(CH$_3$)CH$_2$COSCH$_3$ |
| 391 | Cl | COOCH(CH$_3$)CH$_2$COOCH$_2$CH=CH$_2$ |
| 392 | Cl | COOC(CH$_3$)$_2$COCH$_3$ |
| 393 | Cl | COOC(CH$_3$)$_2$COOH |
| 394 | Cl | COOC(CH$_3$)$_2$COOCH$_3$ |
| 395 | Cl | COOC(CH$_3$)$_2$COOCH$_2$CH$_3$ |
| 396 | Cl | COOC(CH$_3$)$_2$COOCH(CH$_3$)$_2$ |
| 397 | Cl | COOC(CH$_3$)$_2$COO(CH$_2$)$_4$CH$_3$ |
| 398 | Cl | COOC(CH$_3$)$_2$COOCH$_2$C$_6$H$_5$ |
| 399 | Cl | COOC(CH$_3$)$_2$COOCH$_2$(2-F—C$_6$H$_5$) |
| 400 | Cl | COOC(CH$_3$)$_2$COOCH$_2$CH=CH$_2$ |
| 401 | Cl | COOC(CH$_3$)$_2$COOCH(CH$_3$)CH=CH$_2$ |
| 402 | Cl | COOC(CH$_3$)$_2$COOCH$_2$C≡CH |
| 403 | Cl | COO(CH$_3$)$_2$COOCH$_2$CH$_2$OCH$_2$CH$_3$ |
| 404 | Cl | COOC(CH$_3$)$_2$COSCH$_3$ |
| 405 | Cl | COOC(CH$_3$)$_2$COSCH(CH$_3$)$_2$ |
| 406 | Cl | COOC(CH$_3$)$_2$COSCH$_2$C$_6$H$_5$ |
| 407 | Cl | COOC(CH$_3$)$_2$CONH$_2$ |
| 408 | Cl | COOC(CH$_3$)$_2$CONHCH$_2$CH=CH$_2$ |
| 409 | Cl | COOC(CH$_3$)$_2$CON(CH$_2$CH$_3$)$_2$ |
| 410 | Cl | COOC(CH$_3$)$_2$CON(CH$_3$)CH$_2$CH$_2$OCH$_3$ |
| 411 | Cl | COSCH(CH$_3$)COOH |
| 412 | Cl | COSCH(CH$_3$)COOCH$_3$ |
| 413 | Cl | COSCH(CH$_3$)CONHCH$_2$CH=CH$_2$ |
| 414 | Cl | CON(CH$_3$)CH$_2$COOH |
| 415 | Cl | CON(CH$_3$)C(CH$_3$)$_2$COOCH$_2$CH$_3$ |
| 416 | Cl | CON(CH$_3$)OCH$_2$COOCH$_3$ |
| 417 | Cl | CON(CH$_3$)OH |
| 418 | Cl | CH$_3$ |
| 419 | Cl | CH$_2$CH$_3$ |
| 420 | Cl | CH(OH)CH$_3$ |
| 421 | Cl | CH(OCH$_2$CH=CH$_2$)CH$_3$ |
| 422 | Cl | CH$_2$Cl |
| 423 | Cl | CH$_2$OH |
| 424 | Cl | CH$_2$OCOCH$_3$ |
| 425 | Cl | CHClCH$_3$ |
| 426 | Cl | CH$_2$CH$_2$CF$_3$ |
| 427 | Cl | CH=CHCF$_3$ |
| 428 | Cl | CH$_2$CH=CH$_2$ |
| 429 | Cl | CH=CH(CH$_3$) |
| 430 | Cl | C≡CH |
| 431 | Cl | C≡CCH$_2$OH |
| 432 | Cl | CH$_2$CHClCOOH |
| 433 | Cl | (R)—CH$_2$CHClCOOH |
| 434 | Cl | (S)—CH$_2$CHClCOOH |
| 435 | Cl | CH$_2$CH(CH$_3$)COOH |
| 436 | Cl | CH$_2$CH(CH$_3$)COOCH$_2$CH$_3$ |
| 437 | Cl | CH(Cl)CH$_2$COOCH$_3$ |
| 438 | Cl | CH(Cl)C(Cl)$_2$COOH |
| 439 | Cl | CH(Cl)CH(Cl)COOCH$_2$CH$_3$ |
| 440 | Cl | CH$_2$CH(CH$_3$)COOH |
| 441 | Cl | CH$_2$CH(CH$_3$)COCH$_2$CH=CH$_2$ |
| 442 | Cl | CH$_2$CH(CH$_3$)CONH(CH$_2$CH=CH$_2$) |
| 443 | Cl | CH$_2$CH(CH$_3$)CON(CH$_3$)$_2$ |
| 444 | Cl | CH$_2$CH(CH$_3$)COSCH(CH$_3$)$_2$ |
| 445 | Cl | CH$_2$CHClCOOC(CH$_3$)$_3$ |
| 446 | Cl | CH$_2$CHClCOOCH$_3$ |
| 447 | Cl | CH$_2$CHClCOOCH$_2$CH$_3$ |
| 448 | Cl | CH$_2$CHClCOOCH(CH$_3$)$_2$ |
| 449 | Cl | CH$_2$CHClCOOCH$_2$CH=CH$_2$ |
| 450 | Cl | CH$_2$CHClCOOCH$_2$C$_6$H$_5$ |
| 451 | Cl | CH$_2$CHClCOSCH$_3$ |
| 452 | Cl | CH$_2$CHClCOSCH(CH$_3$)$_2$ |
| 453 | Cl | CH$_2$CHClCOSCH$_2$C$_6$H$_5$ |
| 454 | Cl | CH$_2$CHClCONH$_2$ |
| 455 | Cl | CH$_2$CHClCONH(CH$_2$CH=CH$_2$) |
| 456 | Cl | CH$_2$CHClCON(CH$_2$CH$_3$)$_2$ |
| 457 | Cl | CH$_2$CHClCONH(CH$_2$C$_6$H$_5$) |
| 458 | Cl | CH$_2$CHClCON(CH$_3$)CH$_2$C$_6$H$_5$ |
| 459 | Cl | CH=CHCOOH |
| 460 | Cl | (E)-CH=CHCOOH |
| 461 | Cl | (Z)-CH=CHCOOH |
| 462 | Cl | CH=CHCOOCH$_3$ |
| 463 | Cl | CH=CHCOOCH$_2$C$_6$H$_5$ |
| 464 | Cl | CH=CHCOONH$_2$ |
| 465 | Cl | CH=CHCONH(CH$_2$CH=CH$_2$) |
| 466 | Cl | CH=C(Cl)COOH |
| 467 | Cl | CH=C(Cl)CONH$_2$ |
| 468 | Cl | CH=C(Cl)CONH(CH$_2$CH$_3$) |
| 469 | Cl | CH=C(Cl)CON(CH$_2$CH$_3$)$_2$ |
| 470 | Cl | CH=C(Cl)CONH(CH$_2$C$_6$H$_5$) |
| 471 | Cl | CH=C(Cl)COSCH$_3$ |
| 472 | Cl | CH=C(Cl)COSCH(CH$_3$)$_2$ |
| 473 | Cl | CH=C(CH$_3$)COOH |
| 474 | Cl | CH=C(CH$_3$)CONH(CH$_2$CH=CH$_2$) |
| 475 | Cl | CH=C(CH$_3$)CON(CH$_3$)$_2$ |
| 476 | Cl | CH=C(CH$_3$)COSCH$_2$CH$_3$ |
| 477 | Cl | CH=C(CN)COOH |
| 478 | Cl | CH=C(CN)COOC(CH$_3$)$_3$ |
| 479 | Cl | CH=C(CN)CON(CH$_2$CH=CH$_2$)$_2$ |
| 480 | Cl | CH=C(COOH)$_2$ |
| 481 | Cl | CH=C(C$_6$H$_5$)COOH |
| 482 | Cl | CH=CHCH$_2$OH |
| 483 | H | F |
| 484 | H | H |
| 485 | H | Cl |
| 486 | H | Br |
| 487 | H | I |
| 488 | H | NH$_2$ |
| 489 | H | OH |
| 490 | H | SH |
| 491 | H | SO$_2$Cl |
| 492 | H | CN |
| 493 | H | NH(CH$_2$C$_6$H$_5$) |
| 494 | H | N(CH$_2$CH=CH$_2$)$_2$ |
| 495 | H | N(SO$_2$CH$_3$)$_2$ |
| 496 | H | NH(SO$_2$CH$_2$CH$_3$ |
| 497 | H | NH(COCH$_3$) |
| 498 | H | OCH$_3$ |
| 499 | H | OCH$_2$CH$_3$ |
| 500 | H | OCH$_2$CH=CH$_2$ |
| 501 | H | OCH$_2$C≡CH |

TABLE 1-continued

Compounds of the formulae $I_1$ to $I_{34}$

| | | |
|---|---|---|
| 502 | H | $OCH_2C_6H_5$ |
| 503 | H | $OCH_2CH_2Cl$ |
| 504 | H | $OCH_2CH_2OH$ |
| 505 | H | $OCH_2OCH_3$ |
| 506 | H | $OCH_2CH_2OCH_2CH_3$ |
| 507 | H | $OCH_2CH_2OCH_2CH_2OCH_3$ |
| 508 | H | $OCOCH_3$ |
| 509 | H | $OCOOCH_3$ |
| 510 | H | $OCH_2SCH_3$ |
| 511 | H | $OCH_2CH_2SCH_3$ |
| 512 | H | $OCH_2COOH$ |
| 513 | H | $OCH_2COOCH_3$ |
| 514 | H | $OCH_2COOCH_2C_6H_5$ |
| 515 | H | $OCH_2CONH(CH_3)$ |
| 516 | H | $OCH(CH_3)COOH$ |
| 517 | H | $OCH(CH_3)COOCH_2CH_3$ |
| 518 | H | $OCH(CH_3)COOCH_2CH=CH_2$ |
| 519 | H | $OCH(CH_3)COOCH_2C_6H_5$ |
| 520 | H | $OCH(CH_3)CONH_2$ |
| 521 | H | $OCH(CH_3)CONH(CH_2CH=CH_2)$ |
| 522 | H | $OCH(CH_3)CON(CH_3)_2$ |
| 523 | H | $OCH(CH_3)COSCH(CH_3)_2$ |
| 524 | H | $OCH(C_6H_5)COOH$ |
| 525 | H | $OCH(C_6H_5)COOCH_3$ |
| 526 | H | $OCH(C_6H_5)COOCH_2CH=CH_2$ |
| 527 | H | $OCH(C_6H_5)CONH_2$ |
| 528 | H | $OCH(C_6H_5)CONH(CH_2CH_3)$ |
| 529 | H | $OCH(C_6H_5)CON(CH_3)_2$ |
| 530 | H | $OCH(C_6H_5)COSCH_3$ |
| 531 | H | $OCH(C_6H_5)COSCH(CH_3)_2$ |
| 532 | H | $OCH(CH_3)CH_2COOH$ |
| 533 | H | $OCH(CH_3)CH_2COOCH_2CH_3$ |
| 534 | H | $SCH_3$ |
| 535 | H | $SCH(CH_3)_2$ |
| 536 | H | $SCH_2C_6H_5$ |
| 537 | H | $SCH(CH_3)COOH$ |
| 538 | H | $SCH(CH_3)COOCH_2CH_3$ |
| 539 | H | $SO_2NH_2$ |
| 540 | H | $SO_2NH(CH_2CH=CH_2)$ |
| 541 | H | $SO_2N(CH_3)_2$ |
| 542 | H | $SCOCH_3$ |
| 543 | H | $SCOOCH_2CH_3$ |
| 544 | H | $CH_2OCOCH_3$ |
| 545 | H | $COOH$ |
| 546 | H | $COCl$ |
| 547 | H | $COOCH_3$ |
| 548 | H | $COOCH(CH_3)_2$ |
| 549 | H | $COOCH_2C_6H_5$ |
| 550 | H | $COSCH(CH_3)_2$ |
| 551 | H | $CONH_2$ |
| 552 | H | $CONHCH_2C_6H_5$ |
| 553 | H | $CON(CH_2CH=CH_2)_2$ |
| 554 | H | $CON(CH_3)OCH_3$ |
| 555 | H | $COOCH(CH_3)CH_2COOH$ |
| 556 | H | $COOCH(CH_3)COOCH_2CH_3$ |
| 557 | H | $COOCH(CH_3)CH_2COOCH_2CH=CH_2$ |
| 558 | H | $COOCH(CH_3)CH_2COSCH_2CH_3$ |
| 559 | H | $COOCH(CH_3)CH_2CONH_2$ |
| 560 | H | $COOCH(CH_3)CH_2CONH(CH_2CH=CH_2)$ |
| 561 | H | $COOCH(CH_3)COOH$ |
| 562 | H | $COOC(CH_3)_2COOH$ |
| 563 | H | $COOC(CH_3)_2COOCH_3$ |
| 564 | H | $COOC(CH_3)_2COOCH(CH_3)_2$ |
| 565 | H | $COOC(CH_3)_2COOCH_2CH_3$ |
| 566 | H | $COOC(CH_3)_2COOCH_2CH=CH_2$ |
| 567 | H | $COOC(CH_3)_2COOCH_2CH_2OCH_2CH_3$ |
| 568 | H | $COOC(CH_3)_2CONH_2$ |
| 569 | H | $COOC(CH_3)_2CON(CH_3)_2$ |
| 570 | H | $COOC(CH_3)_2CONH(CH_2CH=CH_2)$ |
| 571 | H | $COSCH(CH_3)COOH$ |
| 572 | H | $CON(CH_3)C(CH_3)_2COOH$ |
| 573 | H | $CH_3$ |
| 574 | H | $CH_2CH_3$ |
| 575 | H | $CH(OH)CH_3$ |
| 576 | H | $CH_2Cl$ |
| 577 | H | $CH_2OH$ |
| 578 | H | $CH_2OCOCH_3$ |
| 579 | H | $CH=CHCF_3$ |
| 580 | H | $CH_2CH_2CF_3$ |
| 581 | H | $CH_2CH=CH_2$ |
| 582 | H | $CH_2CHClCOOH$ |
| 583 | H | $CH_2CHClCOOCH_2CH_3$ |
| 584 | H | $CH_2CHClCOOCH_2C_6H_5$ |
| 585 | H | $CH_2CHClCOOCH_2CH=CH_2$ |
| 586 | H | $CH_2CHClCOOC(CH_3)_3$ |
| 587 | H | $CH_2CHClCOSCH(CH_3)_2$ |
| 588 | H | $CH_2CHClCONH_2$ |
| 589 | H | $CH_2CHClCONH(CH_2CH_3)$ |
| 590 | H | $CH_2CHClCON(CH_3)_2$ |
| 591 | H | $CH(Cl)CH(Cl)COOH$ |
| 592 | H | $CH_2C(CH_3)ClCOOH$ |
| 593 | H | $CH_2C(CH_3)ClCOOCH_2CH_3$ |
| 594 | H | $CH_2C(CH_3)ClCOSCH_3$ |
| 595 | H | $CH_2C(CH_3)ClCONH(CH_2CH=CH_2)$ |
| 596 | H | $CH_2C(CH_3)ClCON(CH_3)(CH_2CH=CH_2)$ |
| 597 | H | $CH=CHCOOH$ |
| 598 | H | $CH=C(CH_3)COOH$ |
| 599 | H | $CH=C(Cl)COOH$ |
| 600 | H | $CH=C(CN)COOH$ |
| 601 | H | $CH=C(CN)COOCH_2CH=CH_2$ |
| 602 | H | $CH=C(Cl)COOCH_2CH_3$ |
| 603 | H | $CH=C(CH_3)CONH(CH_2CH=CH_2)$ |
| 604 | H | $CH=C(Cl)COSCH_2CH_3$ |
| 605 | H | $CH=C(Cl)CON(CH_3)_2$ |
| 606 | $CH_3$ | F |
| 607 | $CH_3$ | H |
| 608 | $CH_3$ | Cl |
| 609 | $CH_3$ | Br |
| 610 | $CH_3$ | I |
| 611 | $CH_3$ | $NH_2$ |
| 612 | $CH_3$ | OH |
| 613 | $CH_3$ | SH |
| 614 | $CH_3$ | $SO_2Cl$ |
| 615 | $CH_3$ | CN |
| 616 | $CH_3$ | $NH(CH_2C_6H_5)$ |
| 617 | $CH_3$ | $N(CH_2CH=CH_2)_2$ |
| 618 | $CH_3$ | $N(SO_2CH_3)_2$ |
| 619 | $CH_3$ | $NH(SO_2CH_2CH_3)$ |
| 620 | $CH_3$ | $NH(COCH_3)$ |
| 621 | $CH_3$ | $OCH_3$ |
| 622 | $CH_3$ | $OCH_2CH_3$ |
| 623 | $CH_3$ | $OCH_2CH=CH_2$ |
| 624 | $CH_3$ | $OCH_2C\equiv CH$ |
| 625 | $CH_3$ | $OCH_2C_6H_5$ |
| 626 | $CH_3$ | $OCH_2CH_2Cl$ |
| 627 | $CH_3$ | $OCH_2CH_2OH$ |
| 628 | $CH_3$ | $OCH_2OCH_3$ |
| 629 | $CH_3$ | $OCH_2CH_2OCH_2CH_3$ |
| 630 | $CH_3$ | $OCH_2CH_2OCH_2CH_2OCH_3$ |
| 631 | $CH_3$ | $OCOCH_3$ |
| 632 | $CH_3$ | $OCOOCH_3$ |
| 633 | $CH_3$ | $OCH_2CH_3$ |
| 634 | $CH_3$ | $OCH_2CH_2SCH_3$ |
| 635 | $CH_3$ | $OCH_2COOH$ |
| 636 | $CH_3$ | $OCH_2COOCH_3$ |
| 637 | $CH_3$ | $OCH_2COOCH_2C_6H_5$ |
| 638 | $CH_3$ | $OCH_2CONH(CH_3)$ |
| 639 | $CH_3$ | $OCH(CH_3)COOH$ |
| 640 | $CH_3$ | $OCH(CH_3)COOCH_2CH_3$ |
| 641 | $CH_3$ | $OCH(CH_3)COOCH_2CH=CH_2$ |
| 642 | $CH_3$ | $OCH(CH_3)COOCH_2C_6H_5$ |
| 643 | $CH_3$ | $OCH(CH_3)CONH_2$ |
| 644 | $CH_3$ | $OCH(CH_3)CONH(CH_2CH=CH_2)$ |
| 645 | $CH_3$ | $OCH(CH_3)CON(CH_3)_2$ |
| 646 | $CH_3$ | $OCH(CH_3)COSCH(CH_3)_2$ |
| 647 | $CH_3$ | $OCH(C_6H_5)COOH$ |
| 648 | $CH_3$ | $OCH(C_6H_5)COOCH_3$ |
| 649 | $CH_3$ | $OCH(C_6H_5)COOCH_2CH=CH_2$ |
| 650 | $CH_3$ | $OCH(C_6H_5)CONH_2$ |
| 651 | $CH_3$ | $OCH(C_6H_5)CONH(CH_2CH_3)$ |
| 652 | $CH_3$ | $OCH(C_6H_5)CON(CH_3)_2$ |
| 653 | $CH_3$ | $OCH(C_6H_5)COSCH_3$ |
| 654 | $CH_3$ | $OCH(C_6H_5)COSCH(CH_3)_2$ |
| 655 | $CH_3$ | $OCH(CH_3)CH_2COOH$ |

TABLE 1-continued

Compounds of the formulae $I_1$ to $I_{34}$

| | | |
|---|---|---|
| 666 | $CH_3$ | $OCH(CH_3)CH_2COOCH_2CH_3$ |
| 657 | $CH_3$ | $SCH_3$ |
| 658 | $CH_3$ | $SCH(CH_3)_2$ |
| 659 | $CH_3$ | $SCH_2C_6H_5$ |
| 660 | $CH_3$ | $SCH(CH_3)COOH$ |
| 661 | $CH_3$ | $SCH(CH_3)COOCH_2CH_3$ |
| 662 | $CH_3$ | $SO_2NH_2$ |
| 663 | $CH_3$ | $SO_2NH(CH_2CH=CH_2)$ |
| 664 | $CH_3$ | $SO_2N(CH_3)_2$ |
| 665 | $CH_3$ | $SCOCH_3$ |
| 666 | $CH_3$ | $SCOOCH_2CH_3$ |
| 667 | $CH_3$ | $CH_2OCOCH_3$ |
| 668 | $CH_3$ | $COOH$ |
| 669 | $CH_3$ | $COCl$ |
| 670 | $CH_3$ | $COOCH_3$ |
| 671 | $CH_3$ | $COOCH(CH_3)_2$ |
| 672 | $CH_3$ | $COOCH_2C_6H_5$ |
| 673 | $CH_3$ | $COSCH(CH_3)_2$ |
| 674 | $CH_3$ | $CONH_2$ |
| 675 | $CH_3$ | $CONHCH_2C_6H_5$ |
| 676 | $CH_3$ | $CON(CH_2CH=CH_2)_2$ |
| 677 | $CH_3$ | $CON(CH_3)OCH_3$ |
| 678 | $CH_3$ | $COOCH(CH_3)CH_2COOH$ |
| 679 | $CH_3$ | $COOCH(CH_3)COOCH_2CH_3$ |
| 680 | $CH_3$ | $COOCH(CH_3)CH_2COOCH_2CH=CH_2$ |
| 681 | $CH_3$ | $COOCH(CH_3)CH_2COSCH_2CH_3$ |
| 682 | $CH_3$ | $COOCH(CH_3)CH_2CONH_2$ |
| 683 | $CH_3$ | $COOCH(CH_3)CH_2CONH(CH_2CH=CH_2)$ |
| 684 | $CH_3$ | $COOCH(CH_3)COOH$ |
| 685 | $CH_3$ | $COOC(CH_3)_2COOH$ |
| 686 | $CH_3$ | $COOC(CH_3)_2COOCH_3$ |
| 687 | $CH_3$ | $COOC(CH_3)_2COOCH(CH_3)_2$ |
| 688 | $CH_3$ | $COOC(CH_3)_2COOCH_2CH_3$ |
| 689 | $CH_3$ | $COOC(CH_3)_2COOCH_2CH=CH_2$ |
| 690 | $CH_3$ | $COOC(CH_3)_2COOCH_2CH_2OCH_2CH_3$ |
| 691 | $CH_3$ | $COOC(CH_3)_2CONH_2$ |
| 692 | $CH_3$ | $COOC(CH_3)_2CON(CH_3)_2$ |
| 693 | $CH_3$ | $COOC(CH_3)_2CONH(CH_2CH=CH_2)$ |
| 694 | $CH_3$ | $COSCH(CH_3)COOH$ |
| 695 | $CH_3$ | $CON(CH_3)C(CH_3)_2COOH$ |
| 696 | $CH_3$ | $CH_3$ |
| 697 | $CH_3$ | $CH_2CH_3$ |
| 698 | $CH_3$ | $CH(OH)CH_3$ |
| 699 | $CH_3$ | $CH_2Cl$ |
| 700 | $CH_3$ | $CH_2OH$ |
| 701 | $CH_3$ | $CH_2OCOCH_3$ |
| 702 | $CH_3$ | $CH=CHCF_3$ |
| 703 | $CH_3$ | $CH_2CH_2CF_3$ |
| 704 | $CH_3$ | $CH_2CH=CH_2$ |
| 705 | $CH_3$ | $CH_2CHClCOOH$ |
| 706 | $CH_3$ | $CH_2CHClCOOCH_2CH_3$ |
| 707 | $CH_3$ | $CH_2CHClCOOCH_2C_6H_5$ |
| 708 | $CH_3$ | $CH_2CHClCOOCH_2CH=CH_2$ |
| 709 | $CH_3$ | $CH_2CHC(COOC(CH_3)_3$ |
| 710 | $CH_3$ | $CH_2CHClCOSCH(CH_3)_2$ |
| 711 | $CH_3$ | $CH_2CHClCONH_2$ |
| 712 | $CH_3$ | $CH_2CHClCONH(CH_2CH_3)$ |
| 713 | $CH_3$ | $CH_2CHClCON(CH_3)_2$ |
| 714 | $CH_3$ | $CH(Cl)CH(Cl)COOH$ |
| 715 | $CH_3$ | $CH_2C(CH_3)ClCOOH$ |
| 716 | $CH_3$ | $CH_2C(CH_3)ClCOOCH_2CH_3$ |
| 717 | $CH_3$ | $CH_2C(CH_3)ClCOSCH_3$ |
| 718 | $CH_3$ | $CH_2C(CH_3)ClCONH(CH_2CH=CH_2)$ |
| 719 | $CH_3$ | $CH_2C(CH_3)ClCON(CH_3)(CH_2CH=CH_2)$ |
| 720 | $CH_3$ | $CH=CHCOOH$ |
| 721 | $CH_3$ | $CH=C(CH_3)COOH$ |
| 722 | $CH_3$ | $CH=C(Cl)COOH$ |
| 723 | $CH_3$ | $CH=C(CN)COOCH_2CH=CH_2$ |
| 724 | $CH_3$ | $CH=C(CN)COOH$ |
| 725 | $CH_3$ | $CH=C(Cl)COOCH_2CH_3$ |
| 726 | $CH_3$ | $CH=C(CH_3)CONH(CH_2CH=CH_2)$ |
| 727 | $CH_3$ | $CH=C(Cl)COSCH_2CH_3$ |
| 728 | $CH_3$ | $CH=C(Cl)CON(CH_3)_2$ |
| 729 | H | N-imidazolyl |
| 730 | F | N-imidazolyl |
| 731 | Cl | N-imidazolyl |
| 732 | $CH_3$ | N-imidazolyl |
| 733 | H | $COOCH_2CH_3$ |
| 734 | $CH_3$ | $COOCH_2CH_3$ |
| 735 | F | $N(CH_3)_2$ |
| 736 | F | $OCH_2CH_2OCH_2CH_2OCH_3$ |
| 737 | F | $OCH_2COOCH_2CH_3$ |
| 738 | F | $OCH(CH_3)COOCH_2CH_3$ |
| 739 | F | $OCH_2CH(OH)CH_2OH$ |
| 740 | F | $CH=CH_2$ |
| 741 | F | $COSCH_2CH_3$ |
| 742 | F | $COO^{-+}NH_2(CH(CH_3)_2)_2$ |
| 743 | F | $COO^{-+}NH(CH_2CH_2OH)_3$ |
| 744 | F | $COO^{-+}K$ |
| 745 | F | $OCH_2COOC(CH_3)_3$ |
| 746 | F | $OCH_2CH_2C_6H_5$ |
| 747 | F | $N(CH_2C\equiv CH)(SO_2CH_2CH_3)$ |
| 748 | F | $OCH_2CH_2CH_3$ |
| 749 | F | $OCH(C_6H_5)COOCH_2CH_3$ |
| 750 | F | $OCH_2CH_2CH_2COOCH_2CH_3$ |
| 751 | F | $COOCH_2CH(CH_3)CF_3$ |
| 752 | F | $COOCH(CH_3)COOCH_2CH_3$ |
| 753 | F | $CON(CH_2CH_2)_2$ |
| 754 | F | $COOCH_2CH_2CH_2CH_3$ |
| 755 | F | $COOCH_2CH_2SCH_2CH_2CH_2CH_3$ |
| 756 | F | $COOCH_2CN$ |
| 757 | F | $COOCH_2CH_2SCH(CH_3)_2$ |
| 758 | F | $COOCH_2CH_2C_6H_5$ |
| 759 | F | $COOCH(CH_3)CH_2CH_3$ |
| 760 | F | $COO(CH_2)_5COOCH_2CH_3$ |
| 761 | F | $COOC(CH_3)_3$ |
| 762 | F | $OCH_2CH_2CH_3$ |
| 763 | F | $OCH_2CH=CHCl$ |
| 764 | F | $CH=C(CH_3)COOCH_2CH_3$ |
| 765 | F | COO-cyclopropyl |
| 766 | F | COO-cyclohexyl |
| 767 | F | $COOCH_{2\text{-cyclopropyl}}$ |
| 768 | F | $COOCH_2C_6H_5$ |
| 769 | F | $COOCH_2CH_2OCH_3$ |
| 770 | F | $COOCH_2CH_3$ |
| 771 | F | $COOCH_2CH(CH_3)_2$ |
| 772 | F | $COOCH_2CH_2CH_3$ |
| 773 | F | $COOCH_2CH(CH_3)CH_2CH_3$ |
| 774 | F | $COOCH_2(p\text{-}Cl\text{—}C_6H_4)$ |
| 775 | F | $COOCH(CH_3)C_6H_4$ |
| 776 | F | $COSCH_2(o\text{-}F\text{—}C_6H_4)$ |
| 777 | F | $COSCH(CH_3)CH_2CH_3$ |
| 778 | F | $COSCH(CH_3)C_6H_5$ |
| 779 | F | $COSCH_2CH_3$ |
| 780 | F | $COSCH_2CH=CH_2$ |
| 781 | F | $CON(CH_2CH=CH_2)CH_2CH_3$ |
| 782 | F | $CON(SO_2CH_3)CH_3$ |
| 783 | F | $CON(SO_2CH_3)CH_2CH=CH_2$ |
| 784 | Cl | COO-cyclopropyl |
| 785 | Cl | COO-cyclohexyl |
| 786 | Cl | $COOCH_{2\text{-cyclopropyl}}$ |
| 787 | Cl | $COOCH_2C_6H_5$ |
| 788 | Cl | $COOCH_2CH_2OCH_3$ |
| 789 | Cl | $COOCH_2CH_2CH_3$ |
| 790 | Cl | $COOCH_2CH(CH_3)_2$ |
| 791 | Cl | $COOCH_2CH_2CH_2CH_3$ |
| 792 | Cl | $COOCH_2CH(CH_3)CH_2CH_3$ |
| 793 | Cl | $COOCH_2(p\text{-}Cl\text{—}C_6H_4)$ |
| 794 | Cl | $COOCH(CH_3)C_6H_5$ |
| 795 | Cl | $COOCH(CH_3)C_6H_5$ |
| 796 | Cl | $COSCH_2(o\text{-}F\text{—}C_6H_4)$ |
| 797 | Cl | $COSCH(CH_3)CH_2CH_3$ |
| 798 | Cl | $COSCH(CH_3)C_6H_5$ |
| 799 | Cl | $COSCH_2CH_3$ |
| 800 | Cl | $COSCH_2CH=CH_2$ |
| 801 | Cl | $CON(CH_2CH=CH_2)CH_2CH_3$ |
| 802 | Cl | $CON(SO_2CH_3)CH_3$ |
| 803 | Cl | $CON(SO_2CH_3)CH_2CH=CH_2$ |
| 804 | H | $COOC(CH_3)_2COCl$ |
| 805 | F | $CH=C(F)COOCH_2CH_3$ (E/Z) |
| 806 | F | $CH=C(Cl)COOCH_2CH_3$ (E/Z) |
| 807 | F | $OCH_2COOCH_2C_6H_5$ |
| 808 | F | $OCH_2CN$ |

TABLE 2
Compounds of the formulae I$_{35}$–I$_{67}$, I$_{147}$, I$_{148}$
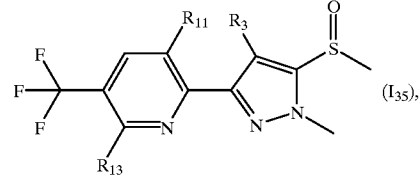 (I$_{35}$),
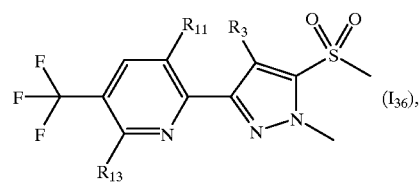 (I$_{36}$),
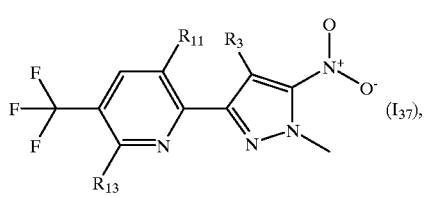 (I$_{37}$),
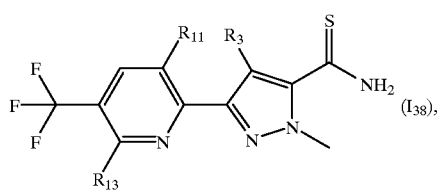 (I$_{38}$),
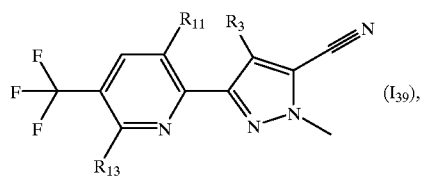 (I$_{39}$),
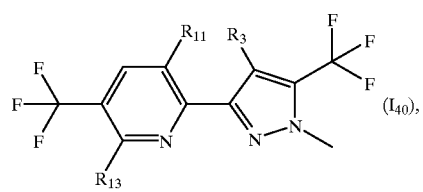 (I$_{40}$),
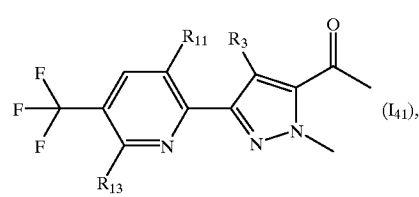 (I$_{41}$),
TABLE 2-continued
Compounds of the formulae I$_{35}$–I$_{67}$, I$_{147}$, I$_{148}$
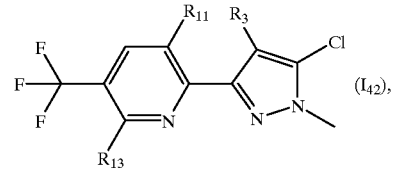 (I$_{42}$),
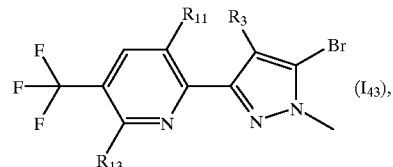 (I$_{43}$),
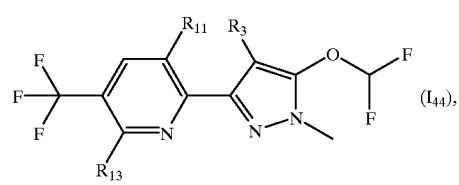 (I$_{44}$),
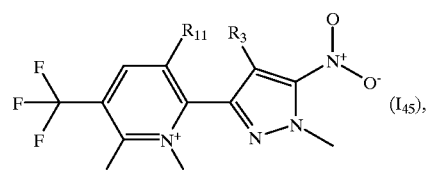 (I$_{45}$),
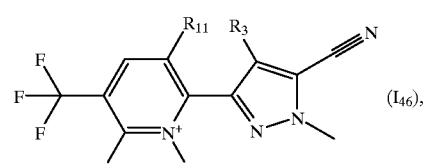 (I$_{46}$),
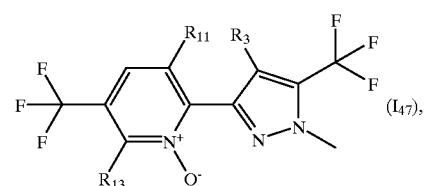 (I$_{47}$),
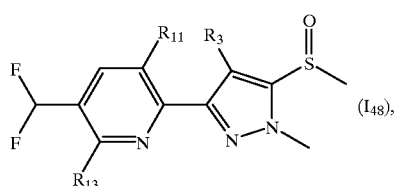 (I$_{48}$),
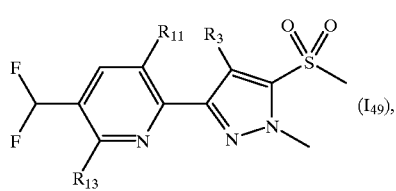 (I$_{49}$),

TABLE 2-continued
Compounds of the formulae $I_{35}$–$I_{67}$, $I_{147}$, $I_{148}$
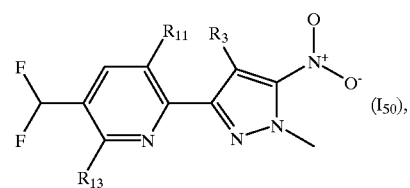
($I_{50}$),
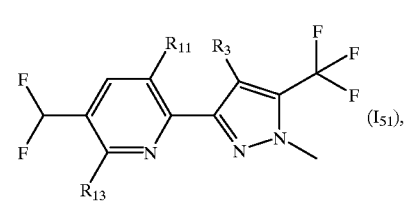
($I_{51}$),
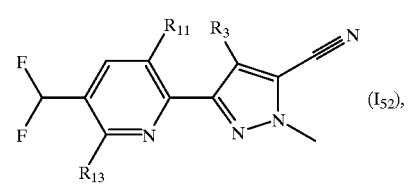
($I_{52}$),
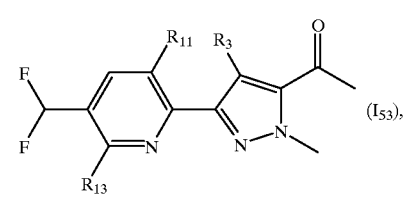
($I_{53}$),
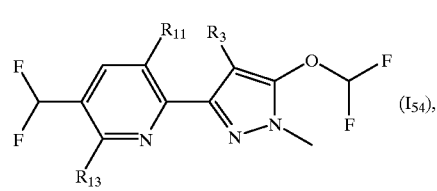
($I_{54}$),
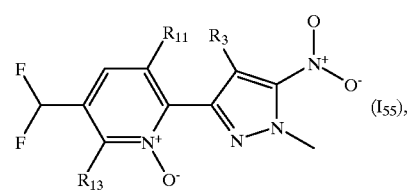
($I_{55}$),
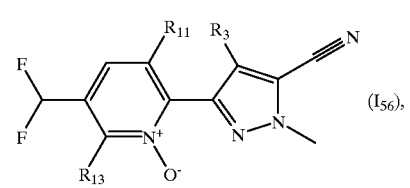
($I_{56}$),
TABLE 2-continued
Compounds of the formulae $I_{35}$–$I_{67}$, $I_{147}$, $I_{148}$
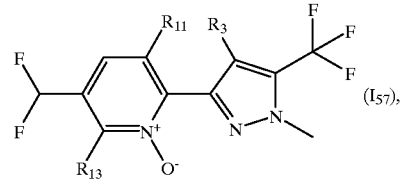
($I_{57}$),
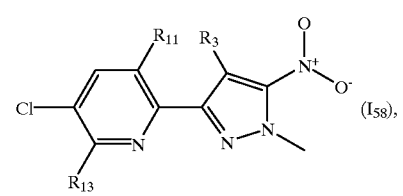
($I_{58}$),
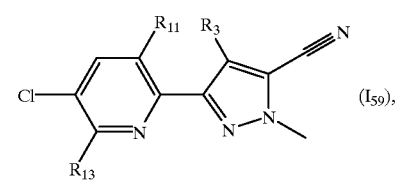
($I_{59}$),
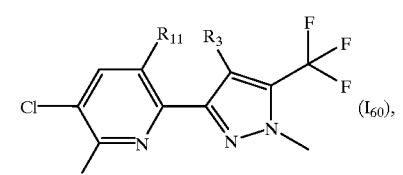
($I_{60}$),
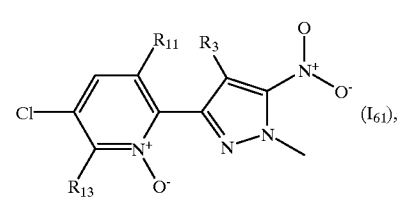
($I_{61}$),
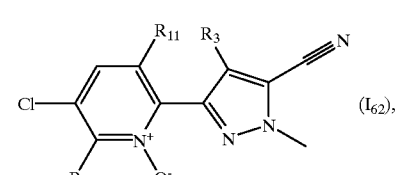
($I_{62}$),
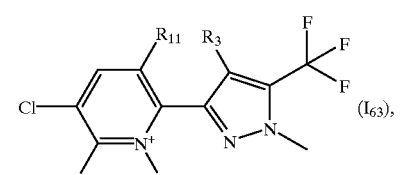
($I_{63}$), TABLE 2-continued Compounds of the formulae I$_{35}$–I$_{67}$, I$_{147}$, I$_{148}$ Structure (I$_{64}$): 5-bromo-pyridine with R$_{11}$, R$_{13}$ substituents, linked to pyrazole bearing R$_3$, NO$_2$, N-CH$_3$.

Structure (I$_{65}$): 5-bromo-pyridine with R$_{11}$, R$_{13}$, linked to pyrazole bearing R$_3$, CN, N-CH$_3$.

Structure (I$_{66}$): cyano-pyridine with R$_{11}$, R$_{13}$, linked to pyrazole bearing R$_3$, NO$_2$, N-CH$_3$.

Structure (I$_{67}$): cyano-pyridine with R$_{11}$, R$_{13}$, linked to pyrazole bearing R$_3$, CN, N-CH$_3$.

Structure (I$_{147}$): 5-chloro-pyridine with R$_{11}$, R$_{13}$, linked to pyrazole bearing R$_3$, OCHF$_2$, N-CH$_3$.

Structure (I$_{148}$): 5-bromo-pyridine with R$_{11}$, R$_{13}$, linked to pyrazole bearing R$_3$, OCHF$_2$, N-CH$_3$.

| Comp. No. I$_n$ n = 35–67, 147, 148 | R$_3$ | R$_{11}$ | R$_{13}$ |
|---|---|---|---|
| 001 | Cl | H | H |
| 002 | Br | H | H |
| 003 | NH$_2$ | H | H |
| 004 | NH(CH$_2$CH$_3$) | H | H |
| 005 | N(CH$_2$C≡CH)$_2$ | H | H |
| 006 | N(CH$_3$)(CH$_2$CH=CH$_2$) | H | H |
| 007 | NH(CH$_2$C$_6$H$_5$) | H | H |
| 008 | pyrrolidin-1-yl | H | H |
| 009 | NHCOCH$_3$ | H | H |
| 010 | NHCOCH$_2$CH$_3$ | H | H |
| 011 | NHCOCHClCH$_3$ | H | H |
| 012 | NHCOCH$_2$Cl | H | H |
| 013 | NHCOCHCl$_2$ | H | H |
| 014 | N(CH$_3$)COCHCl$_2$ | H | H |
| 015 | N(CH$_2$C≡CH)COCHCl$_2$ | H | H |
| 016 | NHCOCF$_3$ | H | H |
| 017 | N(COCF$_3$)$_2$ | H | H |
| 018 | NHCOCF$_2$CF$_3$ | H | H |
| 019 | NHCOCClF$_2$ | H | H |
| 020 | NHCOCF$_2$CF$_2$CF$_3$ | H | H |
| 021 | NHCO(2-thienyl) | H | H |
| 022 | NHCO(3-furanyl) | H | H |
| 023 | NHCO(3-tetrahydrofuranyl) | H | H |
| 024 | NHCO(2-furanyl) | H | H |
| 025 | NHCO(2-tetrahydrofuranyl) | H | H |
| 026 | NHSO$_2$CH$_3$ | H | H |
| 027 | N(SO$_2$CH$_3$)$_2$ | H | H |
| 028 | NHSO$_2$CH$_2$CH$_3$ | H | H |
| 029 | N(CH$_2$C≡CH)SO$_2$CH$_2$CH$_3$ | H | H |
| 030 | NHSO$_2$CF$_3$ | H | H |
| 031 | Cl | Cl | H |
| 032 | Br | Cl | H |
| 033 | NH$_2$ | Cl | H |
| 034 | NH(CH$_2$CH$_3$) | Cl | H |
| 035 | N(CH$_2$C≡CH)$_2$ | Cl | H |
| 036 | N(CH$_3$)(CH$_2$CH=CH$_2$) | Cl | H |
| 037 | NH(CH$_2$C$_6$H$_5$) | Cl | H |
| 038 | pyrrolidin-1-yl | Cl | H |
| 039 | NHCOCH$_3$ | Cl | H |
| 040 | NHCOCH$_2$CH$_3$ | Cl | H |
| 041 | NHCOCHClCH$_3$ | Cl | H |
| 042 | NHCOCH$_2$Cl | CJ | H |
| 043 | NHCOCHCl$_2$ | Cl | H |
| 044 | N(CH$_3$)COCHCl$_2$ | Cl | H |
| 045 | N(CH$_2$C≡CH)COCHCl$_2$ | Cl | H |
| 046 | NHCOCF$_3$ | Cl | H |
| 047 | N(COCF$_3$)$_2$ | Cl | H |
| 048 | NHCOCF$_2$CF$_3$ | Cl | H |
| 049 | NHCOCClF$_2$ | Cl | H |
| 050 | NHCOCF$_2$CF$_2$CF$_3$ | Cl | H |
| 051 | NHCO(2-thienyl) | Cl | H |
| 052 | NHCO(3-furanyl) | Cl | H |
| 053 | NHCO(3-tetrahydrofuranyl) | Cl | H |
| 054 | NHCO(2-furanyl) | Cl | H |
| 055 | NHCO(2-tetrahydrofuranyl) | Cl | H |
| 056 | NHSO$_2$CH$_3$ | Cl | H |
| 057 | N(SO$_2$CH$_3$)$_2$ | Cl | H |
| 058 | NHSO$_2$CH$_2$CH$_3$ | Cl | H |
| 059 | N(CH$_2$C≡CH)SO$_2$CH$_2$CH$_3$ | Cl | H |
| 060 | NHSO$_2$CF$_3$ | Cl | H |
| 061 | Cl | CH$_3$ | H |
| 062 | Br | CH$_3$ | H |
| 063 | NH$_2$ | CH$_3$ | H |
| 064 | NH(CH$_2$CH$_3$) | CH$_3$ | H |
| 065 | N(CH$_2$C≡CH)$_2$ | CH$_3$ | H |
| 066 | N(CH$_3$)(CH$_2$CH=CH$_2$) | CH$_3$ | H |
| 067 | NH(CH$_2$C$_6$H$_5$) | CH$_3$ | H |
| 068 | pyrrolidin-1-yl | CH$_3$ | H |
| 069 | NHCOCH$_3$ | CH$_3$ | H |
| 070 | NHCOCH$_2$CH$_3$ | CH$_3$ | H |
| 071 | NHCOCHClCH$_3$ | CH$_3$ | H |
| 072 | NHCOCH$_2$Cl | CH$_3$ | H |
| 073 | NHCOCHCl$_2$ | CH$_3$ | H |

TABLE 2-continued

Compounds of the formulae $I_{35}$–$I_{67}$, $I_{147}$, $I_{148}$

| | | | |
|---|---|---|---|
| 074 | N(CH$_3$)COCHCl$_2$ | CH$_3$ | H |
| 075 | N(CH$_2$C≡CH)COCHCl$_2$ | CH$_3$ | H |
| 076 | NHCOCF$_3$ | CH$_3$ | H |
| 077 | N(COCF$_3$)$_2$ | CH$_3$ | H |
| 078 | NHCOCF$_2$CF$_3$ | CH$_3$ | H |
| 079 | NHCOCClF$_2$ | CH$_3$ | H |
| 080 | NHCOCF$_2$CF$_2$CF$_3$ | CH$_3$ | H |
| 081 | NHCO(2-thienyl) | CH$_3$ | H |
| 082 | NHCO(3-furanyl) | CH$_3$ | H |
| 083 | NHCO(3-tetrahydrofuranyl) | CH$_3$ | H |
| 084 | NHCO(2-furanyl) | CH$_3$ | H |
| 085 | NHCO(2-tetrahydrofuranyl) | CH$_3$ | H |
| 086 | NHSO$_2$CH$_3$ | CH$_3$ | H |
| 087 | N(SO$_2$CH$_3$)$_2$ | CH$_3$ | H |
| 088 | NHSO$_2$CH$_2$CH$_3$ | CH$_3$ | H |
| 089 | N(CH$_2$C≡CH)SO$_2$CH$_2$CH$_3$ | CH$_3$ | H |
| 090 | NHSO$_2$CF$_3$ | CH$_3$ | H |
| 091 | Cl | F | H |
| 092 | Br | F | H |
| 093 | NH$_2$ | F | H |
| 094 | NH(CH$_2$CH$_3$) | F | H |
| 095 | N(CH$_2$C≡CH)$_2$ | F | H |
| 096 | N(CH$_3$)(CH$_2$CH=CH$_2$) | F | H |
| 097 | NH(CH$_2$C$_6$H$_5$) | F | H |
| 098 | (1-pyrrolidinyl) | F | H |
| 099 | NHCOCH$_3$ | F | H |
| 100 | NHCOCH$_2$CH$_3$ | F | H |
| 101 | NHCOCHClCH$_3$ | F | H |
| 102 | NHCOCH$_2$Cl | F | H |
| 103 | NHCOCHCl$_2$ | F | H |
| 104 | N(CH$_3$)COCHCl$_2$ | F | H |
| 105 | N(CH$_2$C≡CH)COCHCl$_2$ | F | H |
| 106 | NHCOCF$_3$ | F | H |
| 107 | N(COCF$_3$)$_2$ | F | H |
| 108 | NHCOCF$_2$CF$_3$ | F | H |
| 109 | NHCOCClF$_2$ | F | H |
| 110 | NHCOCF$_2$CF$_2$CF$_3$ | F | H |
| 111 | NHCO(2-thienyl) | F | H |
| 112 | NHCO(3-furanyl) | F | H |
| 113 | NHCO(3-tetrahydrofuranyl) | F | H |
| 114 | NHCO(2-furanyl) | F | H |
| 115 | NHCO(2-tetrahydrofuranyl) | F | H |
| 116 | NHSO$_2$CH$_3$ | F | H |
| 117 | N(SO$_2$CH$_3$)$_2$ | F | H |
| 118 | NHSO$_2$CH$_2$CH$_3$ | F | H |
| 119 | N(CH$_2$CCH)SO$_2$CH$_2$CH$_3$ | F | H |
| 120 | NHSO$_2$CF$_3$ | F | H |
| 121 | Cl | Cl | F |
| 122 | Br | Cl | F |
| 123 | NH$_2$ | Cl | F |
| 124 | NH(CH$_2$CH$_3$) | Cl | F |
| 125 | N(CH$_2$C≡CH)$_2$ | Cl | F |
| 126 | N(CH$_3$)(CH$_2$CH=CH$_2$) | Cl | F |
| 127 | NH(CH$_2$C$_6$H$_5$) | Cl | F |
| 128 | (1-pyrrolidinyl) | Cl | F |
| 129 | NHCOCH$_3$ | Cl | F |
| 130 | NHCOCH$_2$CH$_3$ | Cl | F |
| 131 | NHCOCHClCH$_3$ | Cl | F |
| 132 | NHCOCH$_2$Cl | Cl | F |
| 133 | NHCOCHCl$_2$ | Cl | F |
| 134 | N(CH$_3$)COCHCl$_2$ | Cl | F |
| 135 | N(CH$_2$C≡CH)COCHCl$_2$ | Cl | F |
| 138 | NHCOCF$_3$ | Cl | F |
| 137 | N(COCF$_3$)$_2$ | Cl | F |
| 138 | NHCOCF$_2$CF$_3$ | Cl | F |
| 139 | NHCOCClF$_2$ | Cl | F |
| 140 | NHCOCF$_2$CF$_2$CF$_3$ | Cl | F |
| 141 | NHCO(2-thienyl) | Cl | F |
| 142 | NHCO(3-furanyl) | Cl | F |
| 143 | NHCO(3-tetrahydrofuranyl) | Cl | F |
| 144 | NHCO(2-furanyl) | Cl | F |
| 145 | NHCO(2-tetrahydrofuranyl) | Cl | F |
| 146 | NHSO$_2$CH$_3$ | Cl | F |
| 147 | N(SO$_2$CH$_3$)$_2$ | Cl | F |
| 148 | NHSO$_2$CH$_2$CH$_3$ | Cl | F |
| 149 | N(CH$_2$C≡CH)SO$_2$CH$_2$CH$_3$ | C1 | F |
| 150 | NHSO$_2$CF$_3$ | Cl | F |
| 151 | Cl | Br | H |
| 152 | Br | Br | H |
| 153 | NH$_2$ | Br | H |
| 154 | NH(CH$_2$CH$_3$) | Br | H |
| 155 | N(CH$_2$C≡CH)$_2$ | Br | H |
| 156 | N(CH$_3$)(CH$_2$CH=CH$_2$) | Br | H |
| 157 | NH(CH$_2$C$_6$H$_5$) | Br | H |
| 158 | (1-pyrrolidinyl) | Br | H |
| 159 | NHCOCH$_3$ | Br | H |
| 160 | NHCOCH$_2$CH$_3$ | Br | H |
| 161 | NHCOCHClCH$_3$ | Br | H |
| 162 | NHCOCH$_2$Cl | Br | H |
| 163 | NHCOCHCl$_2$ | Br | H |
| 164 | N(CH$_3$)COCHCl$_2$ | Br | H |
| 165 | N(CH$_2$C≡CH)COCHCl$_2$ | Br | |
| 166 | NHCOCF$_3$ | Br | H |
| 167 | N(COCF$_3$)$_2$ | Br | H |
| 168 | NHCOCF$_2$CF$_3$ | Br | H |
| 169 | NHCOCClF$_2$ | Br | H |
| 170 | NHCOCF$_2$CF$_2$CF$_3$ | Br | H |
| 171 | NHCO(2-thienyl) | Br | H |
| 172 | NHCO(3-furanyl) | Br | H |
| 173 | NHCO(3-tetrahydrofuranyl) | Br | H |
| 174 | NHCO(2-furanyl) | Br | H |
| 175 | NHCO(2-tetrahydrofuranyl) | Br | H |
| 176 | NHSO$_2$CH$_3$ | Br | H |
| 177 | N(SO$_2$CH$_3$)$_2$ | Br | H |
| 178 | NHSO$_2$CH$_2$CH$_3$ | Br | H |
| 179 | N(CH$_2$C≡CH)SO$_2$CH$_2$CH$_3$ | Br | H |
| 180 | NHSO$_2$CF$_3$ | Br | H |
| 181 | NH$_2$ | Cl | Cl |
| 182 | NHCOCHCl$_2$ | Cl | Cl |
| 163 | NHCOCH$_2$Cl | Cl | Cl |
| 184 | NH$_2$ | F | Cl |
| 185 | NHCOCHCl$_2$ | F | Cl |

TABLE 3

Compounds of the formulae $I_{68}$–$I_{106}$, $I_{137}$–$I_{146}$ (I$_{68}$)

Structure: pyridine N-oxide with $R_{11}$, Cl substituents, $R_{13}$, linked to a pyrazole bearing Cl, OCHF$_2$, and N–CH$_3$.

TABLE 3-continued

Compounds of the formulae $I_{68}-I_{106}$, $I_{137}-I_{146}$ ($I_{69}$) through ($I_{81}$) — chemical structures.

TABLE 3-continued

Compounds of the formulae I₆₈–I₁₀₆, I₁₃₇–I₁₄₆

TABLE 3-continued

Compounds of the formulae $I_{68}$–$I_{106}$, $I_{137}$–$I_{146}$

TABLE 3-continued

Compounds of the formulae $I_{68}$–$I_{106}$, $I_{137}$–$I_{146}$ ($I_{106}$) [structure with OCH$_3$]

($I_{137}$) [structure with Br, OCH$_2$CF$_3$]

($I_{138}$) [structure with Cl, OCHF$_2$, CHF$_2$]

($I_{139}$) [structure with Cl, OCH$_2$F]

($I_{140}$) [structure with Cl, OCH$_2$CF$_3$]

($I_{141}$) [structure with Br, OCH$_2$CF$_3$]

($I_{142}$) [structure with Cl, OCHF$_2$, CHF$_2$]

($I_{143}$) [structure with Cl, OCH$_2$F]

($I_{144}$) [structure with CHO, OCHF$_2$]

($I_{145}$) [structure with CH$_2$F, OCHF$_2$]

($I_{146}$) [structure with CH$_2$Cl, OCHF$_2$]

| Comp. No. $I_n$ n = 68–106, 137–146 | $R_{11}$ | $R_{13}$ |
|---|---|---|
| 001 | F | F |
| 002 | F | H |
| 003 | F | Cl |
| 004 | F | NH$_2$ |
| 005 | F | OH |
| 006 | F | SH |
| 007 | F | Br |
| 008 | F | I |
| 009 | F | CN |
| 010 | F | SO$_2$Cl |
| 011 | F | NH(CH$_3$) |
| 012 | F | N(CH$_2$CH$_3$)$_2$ |
| 013 | F | NH(COCH$_3$) |
| 014 | F | N(SO$_2$CH$_3$)$_2$ |
| 015 | F | NH(SO$_2$CH$_2$CH$_3$) |
| 016 | F | N(CH$_2$CH=CH$_2$)(SO$_2$CH$_2$CH$_3$) |
| 017 | F | N(CH$_2$C≡CH)(SO$_2$CH(CH$_3$)$_2$) |
| 018 | F | OCH$_3$ |
| 019 | F | OCH$_2$CH$_3$ |
| 020 | F | OCH(CH$_3$)$_2$ |
| 021 | F | OCH$_2$CHCH$_2$ |
| 022 | F | OCH(CH$_3$)CH=CH$_2$ |
| 023 | F | OCH$_2$C≡CH |
| 024 | F | OCH(cyclopentyl) |
| 025 | F | OCH$_2$(2-F—C$_6$H$_5$) |
| 026 | F | OCH(CH$_3$)(4-CH$_3$—C$_6$H$_5$) |
| 027 | F | OC$_6$H$_5$ |
| 028 | F | OCH$_2$CH$_2$Cl |

TABLE 3-continued

Compounds of the formulae $I_{68}$–$I_{106}$, $I_{137}$–$I_{146}$

| | | |
|---|---|---|
| 029 | F | OCH$_2$CH=CHCl |
| 030 | F | OCH$_2$CH$_2$OH |
| 031 | F | OCH$_2$OCH$_3$ |
| 032 | F | OCH$_2$CH$_2$OCH$_2$CH$_3$ |
| 033 | F | OCH$_2$CH$_2$OCH$_2$CH$_2$OCH$_2$CH$_3$ |
| 034 | F | OCH(CH$_3$)CH$_2$OCH$_2$CH=CH$_2$ |
| 035 | F | OCOCH$_3$ |
| 036 | F | OCOOCH$_3$ |
| 037 | F | OCOCH$_2$C$_6$H$_5$ |
| 038 | F | OCH$_2$SCH$_3$ |
| 039 | F | OCH$_2$COOH |
| 040 | F | OCH(CH$_3$)COOH |
| 041 | F | OCH$_2$COOCH$_2$CH$_3$ |
| 042 | F | OCH(CH$_3$)COOCH$_3$ |
| 043 | F | OCH(CH$_3$)COOCH$_2$CH=CH$_2$ |
| 044 | F | OCH(CH$_3$)COOCH$_2$(C$_6$H$_5$) |
| 045 | F | OCH(CH$_3$)CH$_2$COOH |
| 046 | F | OCH(CH$_3$)CH$_2$COOCH$_2$CH$_3$ |
| 047 | F | OCH(CH$_3$)COSCH$_2$CH$_3$ |
| 048 | F | OCH$_2$CONH$_2$ |
| 049 | F | OCH$_2$CON(CH$_2$CH$_3$)$_2$ |
| 050 | F | OCH(CH$_3$)CON(CH$_3$)$_2$ |
| 051 | F | OCH(CH$_3$)CONH(CH$_2$CH=CH$_2$) |
| 052 | F | OCH(CH$_3$)CON(CH$_3$)(CH$_2$C≡CH) |
| 053 | F | OCH(CH$_3$)CON(CH$_3$)(C$_6$H$_5$) |
| 054 | F | OCH$_2$COOCH$_2$CH$_2$SCH$_3$ |
| 055 | F | OCH(CH(CH$_3$)$_2$)COOH |
| 056 | F | OCH(CH$_3$)COOCH$_2$CH$_2$OCH$_2$CH$_3$ |
| 057 | F | OCH(C$_6$H$_5$)COOH |
| 058 | F | OCH(C$_6$H$_5$)COOCH$_3$ |
| 059 | F | OCH(C$_6$H$_5$)COOCH(CH$_3$)C≡CH |
| 060 | F | OCH(C$_6$H$_5$)COOCH$_2$C$_6$H$_5$ |
| 061 | F | OCH(C$_6$H$_5$)COSCH(CH$_3$)$_2$ |
| 062 | F | OCH(C$_6$H$_5$)CONH$_2$ |
| 063 | F | OCH(C$_6$H$_5$)CONH(CH$_2$C≡CH) |
| 064 | F | OCH(C$_6$H$_5$)CON(CH$_2$CH=CH$_2$)$_2$ |
| 065 | F | OCH(C$_6$H$_5$)CON(CH$_3$)CH$_2$C$_6$H$_5$ |
| 066 | F | OCH(C$_6$H$_5$)CONH(cyclopropyl) |
| 067 | F | OCH$_2$CH$_2$COOH |
| 068 | F | OCH$_2$CH$_2$COOCH$_2$CH$_3$ |
| 069 | F | OCH(CH$_3$)CH$_2$COOH |
| 070 | F | SCH$_3$ |
| 071 | F | SCH(CH$_3$)$_2$ |
| 072 | F | SCH$_2$CH=CH$_2$ |
| 073 | F | SCH$_2$C$_6$H$_5$ |
| 074 | F | SCH$_2$CH$_2$OCH$_3$ |
| 075 | F | SCH$_2$COOH |
| 076 | F | SCH$_2$COOCH$_2$C$_6$H$_5$ |
| 077 | F | SCH(CH$_3$)COOH |
| 078 | F | SCH(CH$_3$)COOCH$_2$CH$_3$ |
| 079 | F | SCH(CH$_3$)COOCH$_2$CH=CH$_2$ |
| 080 | F | SCH(CH$_3$)CON(CH$_3$)$_2$ |
| 081 | F | SCH(CH$_3$)CONH(CH$_2$CH=CH$_2$) |
| 082 | F | SOCH$_2$CH$_3$ |
| 083 | F | SO$_2$CH$_3$ |
| 084 | F | SO$_2$NH$_2$ |
| 085 | F | SO$_2$N(CH$_3$)$_2$ |
| 086 | F | SO$_2$N(CH$_2$CH$_3$)$_2$ |
| 087 | F | SO$_2$N(CH$_3$)(CH$_2$(4-CH$_3$—C$_6$H$_5$)) |
| 088 | F | SO$_2$NHCH$_2$CH$_2$OCH$_3$ |
| 089 | F | SCOOCH$_3$ |
| 090 | F | SCON(CH$_3$)$_2$ |
| 091 | F | SCONHCH$_2$CH=CH$_2$ |
| 092 | F | SCOOCH$_2$CH=CH$_2$ |
| 093 | F | SCON(CH$_2$CH$_3$)COCF$_3$ |
| 094 | F | CHO |
| 095 | F | COCH$_3$ |
| 096 | F | COOCH$_2$CH$_3$ |
| 097 | F | COOCH$_2$C$_6$H$_5$ |
| 098 | F | COCl |
| 099 | F | COCH$_2$CH$_2$Cl |
| 100 | F | COOH |
| 101 | F | COOCH$_3$ |
| 102 | F | COOCH$_2$CH$_3$ |
| 103 | F | COOCH(CH$_3$)$_2$ |
| 104 | F | COOCH$_2$CH=CH$_2$ |
| 105 | F | COO(CH$_2$)5CH$_3$ |
| 106 | F | COOCH(CH$_3$)CH=CH$_2$ |
| 107 | F | COOCH$_2$CH$_2$OCH$_2$CH$_3$ |
| 108 | F | COOCH(CH$_3$)CH$_2$SCH$_3$ |
| 109 | F | COOCH$_2$(oxiranyl) |
| 110 | F | COO(cylopentyl) |
| 111 | F | COSCH$_3$ |
| 112 | F | COSCH(CH$_3$)$_2$ |
| 113 | F | COSCH$_2$C$_6$H$_5$ |
| 114 | F | CONH$_2$ |
| 115 | F | CONH(CH$_2$CH=CH$_2$) |
| 116 | F | CONHCH$_2$C$_6$H$_5$ |
| 117 | F | CON(CH$_2$CH=CH$_2$)$_2$ |
| 118 | F | CON(CH$_3$)OCH$_3$ |
| 119 | F | COOCH$_2$CH$_2$COOH |
| 120 | F | COOCH(CH$_3$)COOCH$_3$ |
| 121 | F | COOCH(CH$_3$)COOCH$_2$C$_6$H$_5$ |
| 122 | F | COOCH(CH$_3$)CH$_2$COOCH$_2$CH$_3$ |
| 123 | F | COOCH(CH$_3$)CH$_2$CONHCH$_2$CH$_3$ |
| 124 | F | COOCH(CH$_3$)CH$_2$CON(CH$_3$)$_2$ |
| 125 | F | COOCH(CH$_3$)CH$_2$COSCH$_2$CH$_3$ |
| 126 | F | COOCH(CH$_3$)CH$_2$COOCH$_2$CH=CH$_2$ |
| 127 | F | COOC(CH$_3$)$_2$COCH$_3$ |
| 128 | F | COOC(CH$_3$)$_2$COOH |
| 129 | F | COOC(CH$_3$)$_2$COOCH$_3$ |
| 130 | F | COOC(CH$_3$)$_2$COOCH$_2$CH$_3$ |
| 131 | F | COOC(CH$_3$)$_2$COOCH(CH$_3$)$_2$ |
| 132 | F | COOC(CH$_3$)COO(CH$_2$)$_4$CH$_3$ |
| 133 | F | COOC(CH$_3$)$_2$COOCH$_2$C$_6$H$_5$ |
| 134 | F | COOC(CH$_3$)$_2$COOCH$_2$(2-F—C$_6$H$_5$) |
| 135 | F | COOC(CH$_3$)$_2$COOCH$_2$CH=CH$_2$ |
| 136 | F | COOC(CH$_3$)$_2$COOCH(CH$_3$)CH=CH$_2$ |
| 137 | F | COOC(CH$_3$)$_2$COOCH$_2$C≡CH |
| 138 | F | COO(CH$_3$)$_2$COOCH$_2$CH$_2$OCH$_2$CH$_3$ |
| 139 | F | COOC(CH$_3$)$_2$COSCH$_3$ |
| 140 | F | COOC(CH$_3$)$_2$COSCH(CH$_3$)$_2$ |
| 141 | F | COOC(CH$_3$)$_2$COSCH$_2$C$_6$H$_5$ |
| 142 | F | COOC(CH$_3$)$_2$CONH$_2$ |
| 143 | F | COOC(CH$_3$)$_2$CONHCH$_2$CH=CH$_2$ |
| 144 | F | COOC(CH$_3$)$_2$CON(CH$_2$CH$_3$)$_2$ |
| 145 | F | COOC(CH$_3$)$_2$CON(CH$_3$)CH$_2$CH$_2$OCH$_3$ |
| 146 | F | COSCH(CH$_3$)COOH |
| 147 | F | COSCH(CH$_3$)COOCH$_3$ |
| 148 | F | COSCH(CH$_3$)CONHCH$_2$CH=CH$_2$ |
| 149 | F | CON(CH$_3$)CH$_2$COOH |
| 150 | F | CON(CH$_3$)C(CH$_3$)$_2$COOCH$_2$CH$_3$ |
| 151 | F | CON(CH$_3$)OCH$_2$COOCH$_3$ |
| 152 | F | CON(CH$_3$)OH |
| 153 | F | CH$_3$ |
| 154 | F | CH$_2$CH$_3$ |
| 155 | F | CH(OH)CH$_3$ |
| 156 | F | CH(OCH$_2$CH=CH$_2$)CH$_3$ |
| 157 | F | CH$_2$Cl |
| 158 | F | CH$_2$OH |
| 159 | F | CH$_2$OCOCH$_3$ |
| 160 | F | CHClCH$_3$ |
| 161 | F | CH$_2$CH$_2$CF$_3$ |
| 162 | F | CH=CHCF$_3$ |
| 163 | F | CH$_2$CH=CH$_2$ |
| 164 | F | CH=CHCH$_3$ |
| 165 | F | C≡CH |
| 166 | F | C≡CCH$_2$OH |
| 167 | F | CH$_2$CHClCOOH |
| 168 | F | (R)—CH$_2$CHClCOOH |
| 169 | F | (S)—CH$_2$CHClCOOH |
| 170 | F | CH$_2$CH(CH$_3$)COOH |
| 171 | F | CH$_2$CH(CH$_3$)COOCH$_2$CH$_3$ |
| 172 | F | CH(Cl)CH$_2$COOCH$_3$ |
| 173 | F | CH(Cl)C(Cl)$_2$COOH |
| 174 | F | CH(Cl)CH(Cl)COOCH$_2$CH$_3$ |
| 175 | F | CH$_2$CH(CH$_3$)COOH |
| 176 | F | CH$_2$CH(CH$_3$)COCH$_2$CH=CH$_2$ |
| 177 | F | CH$_2$CH(CH$_3$)CONH(CH$_2$CH=CH$_2$) |
| 178 | F | CH$_2$CH(CH$_3$)CON(CH$_3$)$_2$ |
| 179 | F | CH$_2$CH(CH$_3$)COSCH(CH$_3$)$_2$ |
| 180 | F | CH$_2$CHClCOOC(CH$_3$)$_3$ |
| 181 | F | CH$_2$CHClCOOCH$_3$ |
| 182 | F | CH$_2$CHClCOOCH$_2$CH$_3$ |

TABLE 3-continued

Compounds of the formulae $I_{68}$–$I_{106}$, $I_{137}$–$I_{146}$

| | | |
|---|---|---|
| 183 | F | $CH_2CHClCOOCH(CH_3)_2$ |
| 184 | F | $CH_2CHClCOOCH_2CH=CH_2$ |
| 185 | F | $CH_2CHClCOOCH_2C_6H_5$ |
| 186 | F | $CH_2CHClCOSCH(CH_3)_2$ |
| 187 | F | $CH_2CHClCOSCH_2C_6H_5$ |
| 188 | F | $CH_2CHClCONH_2$ |
| 189 | F | $CH_2CHClCONH(CH_2CH=CH_2)$ |
| 190 | F | $CH_2CHClCON(CH_2CH_3)_2$ |
| 191 | F | $CH_2CHClCONH(CH_2C_6H_5)$ |
| 192 | F | $CH_2CHClCON(CH_3)CH_2C_6H_5$ |
| 193 | F | $CH=CHCOOH$ |
| 194 | F | (E)-$CH=CHCOOH$ |
| 195 | F | (Z)-$CH=CHCOOH$ |
| 196 | F | $CH=CHCOOCH_3$ |
| 197 | F | $CH=CHCOOCH_2C_6H_5$ |
| 198 | F | $CH=CHCOONH_2$ |
| 199 | F | $CH=CHCONH(CH_2CH=CH_2)$ |
| 200 | F | $CH=C(Cl)COOH$ |
| 201 | F | $CH=C(Cl)CONH_2$ |
| 202 | F | $CH=C(Cl)CONH(CH_2CH_3)$ |
| 203 | F | $CH=C(Cl)CON(CH_2CH_3)_2$ |
| 204 | F | $CH=C(Cl)CONH(CH_2C_6H_5)$ |
| 205 | F | $CH=C(Cl)COSCH_3$ |
| 206 | F | $CH=C(Cl)COSCH(CH_3)_2$ |
| 207 | F | $CH=C(CH_3)COOH$ |
| 208 | F | $CH=C(CH_3)CONH(CH_2CH=CH_2)$ |
| 209 | F | $CH=C(CH_3)CON(CH_3)_2$ |
| 210 | F | $CH=C(CH_3)COSCH_2CH_3$ |
| 211 | F | $CH=C(CN)COOH$ |
| 212 | F | $CH=C(CN)COOC(CH_3)_3$ |
| 213 | F | $CH=C(CN)CON(CH_2CH=CH_2)_2$ |
| 214 | F | $CH=C(COOH)_2$ |
| 215 | F | $CH=C(C_6H_5)COOH$ |
| 216 | F | $CH=CHCH_2OH$ |
| 217 | Cl | F |
| 218 | Cl | H |
| 219 | Cl | Cl |
| 220 | Cl | $NH_2$ |
| 221 | Cl | OH |
| 222 | Cl | SH |
| 223 | Cl | Br |
| 224 | Cl | I |
| 225 | Cl | CN |
| 226 | Cl | $SO_2Cl$ |
| 227 | Cl | $NH(CH_3)$ |
| 228 | Cl | $N(CH_2CH_3)_2$ |
| 229 | Cl | $NH(COCH_3)$ |
| 230 | Cl | $NH(CH_2CH=CH_2)$ |
| 231 | Cl | $N(CH_3)(CH_2C\equiv CH)$ |
| 232 | Cl | $N(SO_2CH_3)_2$ |
| 233 | Cl | $NH(SO_2CH_2CH_3)$ |
| 234 | Cl | $N(CH_2CH=CH_2)(SO_2CH_2CH_3)$ |
| 235 | Cl | $N(CH_2C\equiv CH)(SO_2CH(CH_3)_2)$ |
| 236 | Cl | $N(CH_2CF_3)(CHO)$ |
| 237 | Cl | $NH(CH_2C_6H_5)$ |
| 238 | Cl | $OCH_3$ |
| 239 | Cl | $OCH_2CH_3$ |
| 240 | Cl | $OCH(CH_3)_2$ |
| 241 | Cl | $OCH(CH_3)CH_2CH_2CH_3$ |
| 242 | Cl | $OCH_2CH=CH_2$ |
| 243 | Cl | $OCH(CH_3)CH=CH_2$ |
| 244 | Cl | $OCH_2C\equiv CH$ |
| 245 | Cl | $OCH(CH_3)C\equiv CH$ |
| 246 | Cl | $OCH(cyclopentyl)$ |
| 247 | Cl | $OCH_2(C_6H_5)$ |
| 248 | Cl | $OCH_2(2\text{-}F\text{-}C_6H_5)$ |
| 249 | Cl | $OCH(CH_3)(4\text{-}CH_3\text{-}C_6H_5)$ |
| 250 | Cl | $OC_6H_5$ |
| 251 | Cl | O(4-pyrimidyl) |
| 252 | Cl | $OCH_2CH_2Cl$ |
| 253 | Cl | $OCH_2CH=CHCl$ |
| 254 | Cl | $OCH_2CH_2OH$ |
| 255 | Cl | $OCH_2OCH_3$ |
| 256 | Cl | $OCH_2CH_2OCH_2CH_3$ |
| 257 | Cl | $OCH_2CH_2OCH_2CH_2OCH_2CH_3$ |
| 258 | Cl | $OCH(CH_3)CH_2OCH_2CH=CH_2$ |
| 259 | Cl | $OCOCH_3$ |
| 260 | Cl | $OCOOCH_3$ |
| 261 | Cl | $OCOCH_2C_6H_5$ |
| 262 | Cl | $OCH_2SCH_3$ |
| 263 | Cl | $OCH_2CH_2SCH_2CH_3$ |
| 264 | Cl | $OCH_2COOH$ |
| 265 | Cl | $OCH(CH_3)COOH$ |
| 266 | Cl | (R)—$OCH(CH_3)COOH$ |
| 267 | Cl | (S)—$OCH(CH_3)COOH$ |
| 268 | Cl | $OCH_2COOCH_2CH_3$ |
| 269 | Cl | $OCH(CH_3)COOCH_3$ |
| 270 | Cl | $OCH(CH_3)COOCH_2CH=CH_2$ |
| 271 | Cl | $OCH(CH_3)COOCH_2(C_6H_5)$ |
| 272 | Cl | $OCH(CH_3)COSCH_3$ |
| 273 | Cl | $OCH(CH_3)CH_2COOCH_2CH_3$ |
| 274 | Cl | $OCH_2COSCH_3$ |
| 275 | Cl | $OCH(CH_3)COSCH_2CH_3$ |
| 276 | Cl | $OCH(CH_3)COSCH(CH_3)_2$ |
| 277 | Cl | $OCH_2CONH_2$ |
| 278 | Cl | $OCH_2CON(CH_2CH_3)_2$ |
| 279 | Cl | $OCH(CH_3)CON(CH_3)_2$ |
| 280 | Cl | $OCH(CH_3)CONH(CH_2CH=CH_2)$ |
| 281 | Cl | $OCH(CH_3)CON(CH_3)(CH_2C\equiv CH)$ |
| 282 | Cl | $OCH(CH_3)CON(CH_2C_6H_5)_2$ |
| 283 | Cl | $OCH(CH_3)CON(CH_3)(C_6H_5)$ |
| 284 | Cl | $OCH_2COOCH_2CH_2SCH_3$ |
| 285 | Cl | $OCH(CH_3)_2)COOH$ |
| 286 | Cl | $OCH(CH_3)COOCH_2CH_2OCH_2CH_3$ |
| 287 | Cl | $OCH(C_6H_5)COOH$ |
| 288 | Cl | (R)—$OCH(C_6H_5)COOH$ |
| 289 | Cl | (S)—$OCH(C_6H_5)COOH$ |
| 290 | Cl | $OCH(C_6H_5)COOCH_3$ |
| 291 | Cl | $OCH(C_6H_5)COOCH(CH_3)C\equiv CH$ |
| 292 | Cl | $OCH(C_6H_5)COOCH_2C_6H_5$ |
| 293 | Cl | $OCH(C_6H_5)COSCH(CH_3)_2$ |
| 294 | Cl | $OCH(C_6H_5)CONH_2$ |
| 295 | Cl | $OCH(C_6H_5)CONH(CH_2C\equiv CH)$ |
| 296 | Cl | $OCH(C_6H_5)CON(CH_2CH=CH_2)_2$ |
| 297 | Cl | $OCH(C_6H_5)CON(CH_3)CH_2C_6H_5$ |
| 298 | Cl | $OCH(C_6H_5)CONH(CH_2(2\text{-}F\text{-}C_6H_5))$ |
| 299 | Cl | $OCH(C_6H_5)CONH(cyclopropyl)$ |
| 300 | Cl | $OCH_2CH_2COOH$ |
| 301 | Cl | $OCH_2CH_2COOCH_2CH_3$ |
| 302 | Cl | $OCH(CH_3)CH_2COOH$ |
| 303 | Cl | $SCH_3$ |
| 304 | Cl | $SCH(CH_3)_2$ |
| 305 | Cl | $SCH_2CH=CH_2$ |
| 306 | Cl | $SCH_2C_6H_5$ |
| 307 | Cl | $SCH_2CH_2OCH_3$ |
| 308 | Cl | $SC_6H_5$ |
| 309 | Cl | $SCH_2COOH$ |
| 310 | Cl | $SCH_2COOCH_2C_6H_5$ |
| 311 | Cl | $SCH(CH_3)COOH$ |
| 312 | Cl | $SCH(CH_3)COOCH_2CH_3$ |
| 313 | Cl | $SCH(CH_3)COOCH_2CH=CH_2$ |
| 314 | Cl | $SCH(CH_3)COSCH_3$ |
| 315 | Cl | $SCH(CH_3)CON(CH_3)_2$ |
| 316 | Cl | $SCH(CH_3)CONH(CH_2CH=CH_2)$ |
| 317 | Cl | $SOCH_2CH_3$ |
| 318 | Cl | $SO_2CH_3$ |
| 319 | Cl | $SO_2NH_2$ |
| 320 | Cl | $SO_2N(CH_3)_2$ |
| 321 | Cl | $SO_2N(CH_2CH_3)_2$ |
| 322 | Cl | $SO_2N(CH_3)(CH_2(4\text{-}CH_3\text{-}C_6H_5))$ |
| 323 | Cl | $SO_2NHCH_2CH_2OCH_3$ |
| 324 | Cl | $SCOOCH_3$ |
| 325 | Cl | $SCON(CH_3)_2$ |
| 326 | Cl | $SCONHCH_2CH=CH_2$ |
| 327 | Cl | $SCOOCH_2CH=CH_2$ |
| 328 | Cl | $SCON(CH_2CH_3)COCF_3$ |
| 329 | Cl | CHO |
| 330 | Cl | $COCH_3$ |
| 331 | Cl | $COOCH_2CH_3$ |
| 332 | Cl | $COOCH_2C_6H_5$ |
| 333 | Cl | COCl |
| 334 | Cl | $COCH_2CH_2Cl$ |
| 335 | Cl | COOH |
| 336 | Cl | $COOCH_3$ |

TABLE 3-continued

Compounds of the formulae $I_{68}$–$I_{106}$, $I_{137}$–$I_{146}$

| | | |
|---|---|---|
| 337 | Cl | COOCH$_2$CH$_3$ |
| 338 | Cl | COOCH(CH$_3$)$_2$ |
| 339 | Cl | COOCH$_2$CH=CH$_2$ |
| 340 | Cl | COO(CH$_2$)$_5$CH$_3$ |
| 341 | Cl | COOCH(CH$_3$)CH=CH$_2$ |
| 342 | Cl | COOCH$_2$(2-F—C$_6$H$_5$) |
| 343 | Cl | COOC$_6$H$_5$ |
| 344 | Cl | COOCH$_2$CH$_2$OCH$_2$CH$_3$ |
| 345 | Cl | COOCH(CH$_3$)CH$_2$SCH$_3$ |
| 346 | Cl | COO(oxetanyl) |
| 347 | Cl | COOCH$_2$(oxiranyl) |
| 348 | Cl | COO(cylopentyl) |
| 349 | Cl | COSCH$_3$ |
| 350 | Cl | COSCH(CH$_3$)$_2$ |
| 351 | Cl | COSCH$_2$C$_6$H$_5$ |
| 352 | Cl | CONH$_2$ |
| 353 | Cl | CONH(CH$_2$CH=CH$_2$) |
| 354 | Cl | CONHCH$_2$C$_6$H$_5$ |
| 355 | Cl | CON(CH$_2$CH=CH$_2$)$_2$ |
| 356 | Cl | CON(CH$_3$)OCH$_3$ |
| 357 | Cl | COOCH$_2$CH$_2$COOH |
| 358 | Cl | COOCH(CH$_3$)COOCH$_3$ |
| 359 | Cl | COOCH(CH$_3$)COOCH$_2$C$_6$H$_5$ |
| 360 | Cl | COOCH(CH$_3$)CH$_2$COOCH$_2$CH$_3$ |
| 361 | Cl | (S)—COOCH(CH$_3$)CH$_2$COOCH$_2$CH=CH$_2$ |
| 362 | Cl | (R)—COOCH(CH$_3$)CH$_2$COOCH$_2$CH=CH$_2$ |
| 363 | Cl | COOCH(CH$_3$)CH$_2$CONHCH$_2$CH$_3$ |
| 364 | Cl | COOCH(CH$_3$)CH$_2$CON(CH$_3$)$_2$ |
| 365 | Cl | COOCH(CH$_3$)CH$_2$COSCH$_2$CH$_3$ |
| 366 | Cl | COOCH(CH$_3$)CH$_2$COOCH$_2$CH=CH$_2$ |
| 367 | Cl | COOC(CH$_3$)$_2$COCH$_3$ |
| 368 | Cl | COOC(CH$_3$)$_2$COOH |
| 369 | Cl | COOC(CH$_3$)$_2$COOCH$_3$ |
| 370 | Cl | COOC(CH$_3$)$_2$COOCH$_2$CH$_3$ |
| 371 | Cl | COOC(CH$_3$)$_2$COOCH(CH$_3$)$_2$ |
| 372 | Cl | COOC(CH$_3$)$_2$COO(CH$_2$)$_4$CH$_3$ |
| 373 | Cl | COOC(CH$_3$)$_2$COOCH$_2$C$_6$H$_5$ |
| 374 | Cl | COOC(CH$_3$)$_2$COOCH$_2$(2-F—C$_6$H$_5$) |
| 375 | Cl | COOC(CH$_3$)$_2$COOCH$_2$CH=CH$_2$ |
| 376 | Cl | COOC(CH$_3$)$_2$COOCH(CH$_3$)CH=CH$_2$ |
| 377 | Cl | COOC(CH$_3$)$_2$COOCH$_2$C≡CH |
| 378 | Cl | COO(CH$_3$)$_2$COOCH$_2$CH$_2$OCH$_2$CH$_3$ |
| 379 | Cl | COOC(CH$_3$)$_2$COSCH$_3$ |
| 380 | Cl | COOC(CH$_3$)$_2$COSCH(CH$_3$)$_2$ |
| 381 | Cl | COOC(CH$_3$)$_2$COSCH$_2$C$_6$H$_5$ |
| 382 | Cl | COOC(CH$_3$)$_2$CONH$_2$ |
| 383 | Cl | COOC(CH$_3$)$_2$CONHCH$_2$CH=CH$_2$ |
| 384 | Cl | COOC(CH$_3$)$_2$CON(CH$_2$CH$_3$)$_2$ |
| 385 | Cl | COOC(CH$_3$)$_2$CON(CH$_3$)CH$_2$CH$_2$OCH$_3$ |
| 386 | Cl | COSCH(CH$_3$)COOH |
| 387 | Cl | COSCH(CH$_3$)COOCH$_3$ |
| 388 | Cl | COSCH(CH$_3$)CONHCH$_2$CH=CH$_2$ |
| 389 | Cl | CON(CH$_3$)CH$_2$COOH |
| 390 | Cl | CON(CH$_3$)C(CH$_3$)$_2$COOCH$_2$CH$_3$ |
| 391 | Cl | CON(CH$_3$)OCH$_2$COOCH$_3$ |
| 392 | Cl | CON(CH$_3$)OH |
| 393 | Cl | CH$_3$ |
| 394 | Cl | CH$_2$CH$_3$ |
| 395 | Cl | CH(OH)CH$_3$ |
| 396 | Cl | CH(OCH$_2$CH=CH$_2$)CH$_3$ |
| 397 | Cl | CH$_2$Cl |
| 398 | Cl | CH$_2$OH |
| 399 | Cl | CH$_2$OCOCH$_3$ |
| 400 | Cl | CHClCH$_3$ |
| 401 | Cl | CH$_2$CH$_2$CF$_3$ |
| 402 | Cl | CH=CHCF$_3$ |
| 403 | Cl | CH$_2$CH=CH$_2$ |
| 404 | Cl | CH=CH(CH$_3$) |
| 405 | Cl | C≡CH |
| 406 | Cl | C≡CCH$_2$OH |
| 407 | Cl | CH$_2$CHClCOOH |
| 408 | Cl | (R)—CH$_2$CHClCOOH |
| 409 | Cl | (S)—CH$_2$CHClCOOH |
| 410 | Cl | CH$_2$CH(CH$_3$)COOH |
| 411 | Cl | CH$_2$CH(CH$_3$)COOCH$_2$CH$_3$ |
| 412 | Cl | CH(Cl)CH$_2$COOCH$_3$ |
| 413 | Cl | CH(Cl)C(Cl)$_2$COOH |
| 414 | Cl | CH(Cl)CH(Cl)COOCH$_2$CH$_3$ |
| 415 | Cl | CH$_2$CH(CH$_3$)COOH |
| 416 | Cl | CH$_2$CH(CH$_3$)COCH$_2$CH=CH$_2$ |
| 417 | Cl | CH$_2$CH(CH$_3$)CONH(CH$_2$CH=CH$_2$) |
| 418 | Cl | CH$_2$CH(CH$_3$)CON(CH$_3$)$_2$ |
| 419 | Cl | CH$_2$CH(CH$_3$)COSCH(CH$_3$)$_2$ |
| 420 | Cl | CH$_2$CHClCOOC(CH$_3$)$_3$ |
| 421 | Cl | CH$_2$CHClCOOCH$_3$ |
| 422 | Cl | CH$_2$CHClCOOCH$_2$CH$_3$ |
| 423 | Cl | CH$_2$CHClCOOCH(CH$_3$)$_2$ |
| 424 | Cl | CH$_2$CHClCOOCH$_2$CH=CH$_2$ |
| 425 | Cl | CH$_2$CHClCOOCH$_2$C$_6$H$_5$ |
| 426 | Cl | CH$_2$CHClCOSCH$_3$ |
| 427 | Cl | CH$_2$CHClCOSCH(CH$_3$)$_2$ |
| 428 | Cl | CH$_2$CHClCOSCH$_2$C$_6$H$_5$ |
| 429 | Cl | CH$_2$CHClCONH$_2$ |
| 430 | Cl | CH$_2$CHClCONH(CH$_2$CH=CH$_2$) |
| 431 | Cl | CH$_2$CHClCON(CH$_2$CH$_3$)$_2$ |
| 432 | Cl | CH$_2$CHClCONH(CH$_2$C$_6$H$_5$) |
| 433 | Cl | CH$_2$CHClCON(CH$_3$)CH$_2$C$_6$H$_5$ |
| 434 | Cl | CH=CHCOOH |
| 435 | Cl | (E)-CH=CHCOOH |
| 436 | Cl | (Z)-CH=CHCOOH |
| 437 | Cl | CH=CHCOOCH$_3$ |
| 438 | Cl | CH=CHCOOCH$_2$C$_6$H$_5$ |
| 439 | Cl | CH=CHCOONH$_2$ |
| 440 | Cl | CH=CHCONH(CH$_2$CH=CH$_2$) |
| 441 | Cl | CH=C(Cl)COOH |
| 442 | Cl | CH=C(Cl)CONH$_2$ |
| 443 | Cl | CH=C(Cl)CONH(CH$_2$CH$_3$) |
| 444 | Cl | CH=C(Cl)CON(CH$_2$CH$_3$)$_2$ |
| 445 | Cl | CH=C(Cl)CONH(CH$_2$C$_6$H$_5$) |
| 446 | Cl | CH=C(Cl)COSCH$_3$ |
| 447 | Cl | CH=C(Cl)COSCH(CH$_3$) |
| 448 | Cl | CH=C(CH$_3$)COOH |
| 449 | Cl | CH=C(CH$_3$)CONH(CH$_2$CH=CH$_2$) |
| 450 | Cl | CH=C(CH$_3$)CON(CH$_3$)$_2$ |
| 451 | Cl | CH=C(CH$_3$)COSCH$_2$CH$_3$ |
| 452 | Cl | CH=C(CN)COOH |
| 453 | Cl | CH=C(CN)COOC(CH$_3$)$_3$ |
| 454 | Cl | CH=C(CN)CON(CH$_2$CH=CH$_2$)$_2$ |
| 455 | Cl | CH=C(COOH)$_2$ |
| 456 | Cl | CH=C(C$_6$H$_5$)COOH |
| 457 | Cl | CH=CHCH$_2$OH |
| 458 | H | F |
| 459 | H | H |
| 460 | H | Cl |
| 461 | H | Br |
| 462 | H | I |
| 463 | H | NH$_2$ |
| 464 | H | OH |
| 465 | H | SH |
| 466 | H | SO$_2$Cl |
| 467 | H | CN |
| 468 | H | NH(CH$_2$C$_6$H$_5$) |
| 469 | H | N(CH$_2$CH=CH$_2$)$_2$ |
| 470 | H | N(SO$_2$CH$_3$)$_2$ |
| 471 | H | NH(SO$_2$CH$_2$CH$_3$) |
| 472 | H | NH(COCH$_3$) |
| 473 | H | OCH$_3$ |
| 474 | H | OCH$_2$CH$_3$ |
| 475 | H | OCH$_2$CH=CH$_2$ |
| 476 | H | OCH$_2$C≡CH |
| 477 | H | OCH$_2$C$_6$H$_5$ |
| 478 | H | OCH$_2$CH$_2$Cl |
| 479 | H | OCH$_2$CH$_2$OH |
| 480 | H | OCH$_2$OCH$_3$ |
| 481 | H | OCH$_2$CH$_2$OCH$_2$CH$_3$ |
| 482 | H | OCH$_2$CH$_2$OCH$_2$CH$_2$OCH$_3$ |
| 483 | H | OCOCH$_3$ |
| 484 | H | OCOOCH$_3$ |
| 485 | H | OCH$_2$SCH$_3$ |
| 486 | H | OCH$_2$CH$_2$SCH$_3$ |
| 487 | H | OCH$_2$COOH |
| 488 | H | OCH$_2$COOCH$_3$ |
| 489 | H | OCH$_2$COOCH$_2$C$_6$H$_5$ |
| 490 | H | OCH$_2$CONH(CH$_3$) |

TABLE 3-continued

Compounds of the formulae I$_{68}$–I$_{106}$, I$_{137}$–I$_{146}$

| | | |
|---|---|---|
| 491 | H | OCH(CH$_3$)COOH |
| 492 | H | OCH(CH$_3$)COOCH$_2$CH$_3$ |
| 493 | H | OCH(CH$_3$)COOCH$_2$CH=CH$_2$ |
| 494 | H | OCH(CH$_3$)COOCH$_2$C$_6$H$_5$ |
| 495 | H | OCH(CH$_3$)CONH$_2$ |
| 496 | H | OCH(CH$_3$)CONH(CH$_2$CH=CH$_2$) |
| 497 | H | OCH(CH$_3$)CON(CH$_3$)$_2$ |
| 498 | H | OCH(CH$_3$)COSCH(CH$_3$)$_2$ |
| 499 | H | OCH(C$_6$H$_5$)COOH |
| 500 | H | OCH(C$_6$H$_5$)COOCH$_3$ |
| 501 | H | OCH(C$_6$H$_5$)COOCH$_2$CH=CH$_2$ |
| 502 | H | OCH(C$_6$H$_5$)CONH$_2$ |
| 503 | H | OCH(C$_6$H$_5$)CONH(CH$_2$CH$_3$) |
| 504 | H | OCH(C$_6$H$_5$)CON(CH$_3$)$_2$ |
| 505 | H | OCH(C$_6$H$_5$)COSCH$_3$ |
| 506 | H | OCH(C$_6$H$_5$)COSCH(CH$_3$)$_2$ |
| 507 | H | OCH(CH$_3$)CH$_2$COOH |
| 508 | H | OCH(CH$_3$)CH$_2$COOCH$_2$CH$_3$ |
| 509 | H | SCH$_3$ |
| 510 | H | SCH(CH$_3$)$_2$ |
| 511 | H | SCH$_2$C$_6$H$_5$ |
| 512 | H | SCH(CH$_3$)COOH |
| 513 | H | SCH(CH$_3$)COOCH$_2$CH$_3$ |
| 514 | H | SO$_2$NH$_2$ |
| 515 | H | SO$_2$NH(CH$_2$CH=CH$_2$) |
| 516 | H | SO$_2$N(CH$_3$)$_2$ |
| 517 | H | SCOCH$_3$ |
| 518 | H | SCOOCH$_2$CH$_3$ |
| 519 | H | CHOCOCH$_3$ |
| 520 | H | COOH |
| 521 | H | COCl |
| 522 | H | COOCH$_3$ |
| 523 | H | COOCH(CH$_3$)$_2$ |
| 524 | H | COOCH$_2$C$_6$H$_5$ |
| 525 | H | COSCH(CH$_3$)$_2$ |
| 526 | H | CONH$_2$ |
| 527 | H | CONHCH$_2$C$_6$H$_5$ |
| 528 | H | CON(CH$_2$CH=CH$_2$)$_2$ |
| 529 | H | CON(CH$_3$)OCH$_3$ |
| 530 | H | COOCH(CH$_3$)CH$_2$COOH |
| 531 | H | COOCH(CH$_3$)COOCH$_2$CH$_3$ |
| 532 | H | COOCH(CH$_3$)CH$_2$COOCH$_2$CH=CH$_2$ |
| 533 | H | COOCH(CH$_3$)CH$_2$COSCH$_2$CH$_3$ |
| 534 | H | COOCH(CH$_3$)CH$_2$CONH$_2$ |
| 535 | H | COOCH(CH$_3$)CH$_2$CONH(CH$_2$CH=CH$_2$) |
| 536 | H | COOCH(CH$_3$)COOH |
| 537 | H | COOC(CH$_3$)$_2$COOH |
| 538 | H | COOC(CH$_3$)$_2$COOCH$_3$ |
| 539 | H | COOC(CH$_3$)$_2$COOCH(CH$_3$)$_2$ |
| 540 | H | COOC(CH$_3$)$_2$COOCH$_2$CH$_3$ |
| 541 | H | COOC(CH$_3$)$_2$COOCH$_2$CH=CH$_2$ |
| 542 | H | COOC(CH$_3$)$_2$COOCH$_2$CH$_2$OCH$_2$CH$_3$ |
| 543 | H | COOC(CH$_3$)$_2$CONH$_2$ |
| 544 | H | COOC(CH$_3$)$_2$CON(CH$_3$)$_2$ |
| 545 | H | COOC(CH$_3$)$_2$CONH(CH$_2$CH=CH$_2$) |
| 546 | H | COSCH(CH$_3$)COOH |
| 547 | H | CON(CH$_3$)C(CH$_3$)$_2$COOH |
| 548 | H | CH$_3$ |
| 549 | H | CH$_2$CH$_3$ |
| 550 | H | CH(OH)CH$_3$ |
| 551 | H | CH$_2$Cl |
| 552 | H | CH$_2$OH |
| 553 | H | CH$_2$OCOCH$_3$ |
| 554 | H | CH=CHCF$_3$ |
| 555 | H | CH$_2$CH$_2$CF$_3$ |
| 556 | H | CH$_2$CHCH$_2$ |
| 557 | H | CH$_2$CHClCOOH |
| 558 | H | CH$_2$CHClCOOCH$_2$CH$_3$ |
| 559 | H | CH$_2$CHClCOOCH$_2$C$_6$H$_5$ |
| 560 | H | CH$_2$CHClCOOCH$_2$CH=CH$_2$ |
| 561 | H | CH$_2$CHClCOOC(CH$_3$)$_3$ |
| 562 | H | CH$_2$CHClCOSCH(CH$_3$)$_2$ |
| 563 | H | CH$_2$CHClCONH$_2$ |
| 564 | H | CH$_2$CHClCONH(CH$_2$CH$_3$) |
| 565 | H | CH$_2$CHClCON(CH$_3$)$_2$ |
| 566 | H | CH(Cl)CH(Cl)COOH |
| 567 | H | CH$_2$C(CH$_3$)ClCOOH |
| 568 | H | CH$_2$C(CH$_3$)ClCOOCH$_2$CH$_3$ |
| 569 | H | CH$_2$C(CH$_3$)ClCOSCH$_3$ |
| 570 | H | CH$_2$C(CH$_3$)ClCONH(CH$_2$CH=CH$_2$) |
| 571 | H | CH$_2$C(CH$_3$)ClCON(CH$_3$)(CH$_2$CH=CH$_2$) |
| 572 | H | CH=CHCOOH |
| 573 | H | CH=C(CH$_3$)COOH |
| 574 | H | CH=C(Cl)COOH |
| 575 | H | CH=C(CN)COOH |
| 576 | H | CH=C(CN)COOCH$_2$CH=CH$_2$ |
| 577 | H | CH=C(Cl)COOCH$_2$CH$_3$ |
| 578 | H | CH=C(CH$_3$)CONH(CH$_2$CH=CH$_2$) |
| 579 | H | CH=C(Cl)COSCH$_2$CH$_3$ |
| 580 | H | CH=C(Cl)CON(CH$_3$)$_2$ |
| 581 | CH$_3$ | F |
| 582 | CH$_3$ | H |
| 583 | CH$_3$ | Cl |
| 584 | CH$_3$ | Br |
| 585 | CH$_3$ | I |
| 586 | CH$_3$ | NH$_2$ |
| 587 | CH$_3$ | OH |
| 588 | CH$_3$ | SH |
| 589 | CH$_3$ | SO$_2$Cl |
| 590 | CH$_3$ | CN |
| 591 | CH$_3$ | NH(CH$_2$C$_6$H$_5$) |
| 592 | CH$_3$ | N(CH$_2$CH=CH$_2$)$_2$ |
| 593 | CH$_3$ | N(SO$_2$CH$_3$)$_2$ |
| 594 | CH$_3$ | NH(SO$_2$CH$_2$CH$_3$ |
| 595 | CH$_3$ | NH(COCH$_3$) |
| 596 | CH$_3$ | OCH$_3$ |
| 597 | CH$_3$ | OCH$_2$CH$_3$ |
| 598 | CH$_3$ | OCH$_2$CH=CH$_2$ |
| 599 | CH$_3$ | OCH$_2$C≡CH |
| 600 | CH$_3$ | OCH$_2$C$_6$H$_5$ |
| 601 | CH$_3$ | OCH$_2$CH$_2$Cl |
| 602 | CH$_3$ | OCH$_2$CH$_2$OH |
| 603 | CH$_3$ | OCH$_2$OCH$_3$ |
| 604 | CH$_3$ | OCH$_2$CH$_2$OCH$_2$CH$_3$ |
| 605 | CH$_3$ | OCH$_2$CH$_2$OCH$_2$CH$_2$OCH$_3$ |
| 606 | CH$_3$ | OCOCH$_3$ |
| 607 | CH$_3$ | OCOOCH$_3$ |
| 608 | CH$_3$ | OCH$_2$SCH$_3$ |
| 609 | CH$_3$ | OCH$_2$CH$_2$SCH$_3$ |
| 610 | CH$_3$ | OCH$_2$COOH |
| 611 | CH$_3$ | OCH$_2$COOCH$_3$ |
| 612 | CH$_3$ | OCH$_2$COOCH$_2$C$_6$H$_5$ |
| 613 | CH$_3$ | OCH$_2$CONH(CH$_3$) |
| 614 | CH$_3$ | OCH(CH$_3$)COOH |
| 615 | CH$_3$ | OCH(CH$_3$)COOCH$_2$CH$_3$ |
| 616 | CH$_3$ | OCH(CH$_3$)COOCH$_2$CH=CH$_2$ |
| 617 | CH$_3$ | OCH(CH$_3$)COOCH$_2$C$_6$H$_5$ |
| 618 | CH$_3$ | OCH(CH$_3$)CONH$_2$ |
| 619 | CH$_3$ | OCH(CH$_3$)CONH(CH$_2$CH=CH$_2$) |
| 620 | CH$_3$ | OCH(CH$_3$)CON(CH$_3$)$_2$ |
| 621 | CH$_3$ | OCH(CH$_3$)COSCH(CH$_3$)$_2$ |
| 622 | CH$_3$ | OCH(C$_6$H$_5$)COOH |
| 623 | CH$_3$ | OCH(C$_6$H$_5$)COOCH$_3$ |
| 624 | CH$_3$ | OCH(C$_6$H$_5$)COOCH$_2$CH=CH$_2$ |
| 625 | CH$_3$ | OCH(C$_6$H$_5$)CONH$_2$ |
| 626 | CH$_3$ | OCH(C$_6$H$_5$)CONH(CH$_2$CH$_3$) |
| 627 | CH$_3$ | OCH(C$_6$H$_5$)CON(CH$_3$)$_2$ |
| 628 | CH$_3$ | OCH(C$_6$H$_5$)COSCH$_3$ |
| 629 | CH$_3$ | OCH(C$_6$H$_5$)COSCH(CH$_3$)$_2$ |
| 630 | CH$_3$ | OCH(CH$_3$)CH$_2$COOH |
| 631 | CH$_3$ | OCH(CH$_3$)CH$_2$COOCH$_2$CH$_3$ |
| 632 | CH$_3$ | SCH$_3$ |
| 633 | CH$_3$ | SCH(CH$_3$)$_2$ |
| 634 | CH$_3$ | SCH$_2$C$_6$H$_5$ |
| 635 | CH$_3$ | SCH(CH$_3$)COOH |
| 636 | CH$_3$ | SCH(CH$_3$)COOCH$_2$CH$_3$ |
| 637 | CH$_3$ | SO$_2$NH$_2$ |
| 638 | CH$_3$ | SO$_2$NH(CH$_2$CH=CH$_2$) |
| 639 | CH$_3$ | SO$_2$N(CH$_3$)$_2$ |
| 640 | CH$_3$ | SCOCH$_3$ |
| 641 | CH$_3$ | SCOOCH$_2$CH$_3$ |
| 642 | CH$_3$ | CHOCOCH$_3$ |
| 643 | CH$_3$ | COOH |
| 644 | CH$_3$ | COCl |

TABLE 3-continued

Compounds of the formulae $I_{68}$–$I_{106}$, $I_{137}$–$I_{146}$

| | | |
|---|---|---|
| 645 | $CH_3$ | $COOCH_3$ |
| 646 | $CH_3$ | $COOCH(CH_3)_2$ |
| 647 | $CH_3$ | $COOCH_2C_6H_5$ |
| 648 | $CH_3$ | $COSCH(CH_3)_2$ |
| 649 | $CH_3$ | $CONH_2$ |
| 650 | $CH_3$ | $CONHCH_2C_6H_5$ |
| 651 | $CH_3$ | $CON(CH_2CH=CH_2)_2$ |
| 652 | $CH_3$ | $CON(CH_3)OCH_3$ |
| 653 | $CH_3$ | $COOCH(CH_3)CH_2COOH$ |
| 654 | $CH_3$ | $COOCH(CH_3)COOCH_2CH_3$ |
| 655 | $CH_3$ | $COOCH(CH_3)CH_2COOCH_2CH=CH_2$ |
| 656 | $CH_3$ | $COOCH(CH_3)CH_2COSCH_2CH_3$ |
| 657 | $CH_3$ | $COOCH(CH_3)CH_2CONH_2$ |
| 658 | $CH_3$ | $COOCH(CH_3)CH_2CONH(CH_2CH=CH_2)$ |
| 659 | $CH_3$ | $COOCH(CH_3)COOH$ |
| 660 | $CH_3$ | $COOC(CH_3)_2COOH$ |
| 661 | $CH_3$ | $COOC(CH_3)_2COOCH_3$ |
| 662 | $CH_3$ | $COOC(CH_3)_2COOCH(CH_3)_2$ |
| 663 | $CH_3$ | $COOC(CH_3)_2COOCH_2CH_3$ |
| 664 | $CH_3$ | $COOC(CH_3)_2COOCH_2CH=CH_2$ |
| 665 | $CH_3$ | $COOC(CH_3)_2COOCH_2CH_2OCH_2CH_3$ |
| 666 | $CH_3$ | $COOC(CH_3)_2CONH_2$ |
| 667 | $CH_3$ | $COOC(CH_3)_2CON(CH_3)_2$ |
| 668 | $CH_3$ | $COOC(CH_3)_2CONH(CH_2CH=CH_2)$ |
| 669 | $CH_3$ | $COSCH(CH_3)COOH$ |
| 670 | $CH_3$ | $CON(CH_3)C(CH_3)_2COOH$ |
| 671 | $CH_3$ | $CH_3$ |
| 672 | $CH_3$ | $CH_2CH_3$ |
| 673 | $CH_3$ | $CH(OH)CH_3$ |
| 674 | $CH_3$ | $CH_2Cl$ |
| 675 | $CH_3$ | $CH_2OH$ |
| 676 | $CH_3$ | $CH_2OCOCH_3$ |
| 677 | $CH_3$ | $CH=CHCF_3$ |
| 678 | $CH_3$ | $CH_2CH_2CF_3$ |
| 679 | $CH_3$ | $CH_2CH=CH_2$ |
| 680 | $CH_3$ | $CH_2CHClCOOH$ |
| 681 | $CH_3$ | $CH_2CHClCOOCH_2CH_3$ |
| 682 | $CH_3$ | $CH_2CHClCOOCH_2C_6H_5$ |
| 683 | $CH_3$ | $CH_2CHClCOOCH_2CH=CH_2$ |
| 684 | $CH_3$ | $CH_2CHClCOOC(CH_3)_3$ |
| 685 | $CH_3$ | $CH_2CHClCOSCH(CH_3)_2$ |
| 686 | $CH_3$ | $CH_2CHClCONH_2$ |
| 687 | $CH_3$ | $CH_2CHClCONH(CH_2CH_3)$ |
| 688 | $CH_3$ | $CH_2CHClCON(CH_3)_2$ |
| 689 | $CH_3$ | $CH(Cl)CH(Cl)COOH$ |
| 690 | $CH_3$ | $CH_2C(CH_3)ClCOOH$ |
| 691 | $CH_3$ | $CH_2C(CH_3)ClCOOCH_2CH_3$ |
| 692 | $CH_3$ | $CH_2C(CH_3)ClCOSCH_3$ |
| 693 | $CH_3$ | $CH_2C(CH_3)ClCONH(CH_2CH=CH_2)$ |
| 694 | $CH_3$ | $CH_2C(CH_3)ClCON(CH_3)(CH_2CH=CH_2)$ |
| 695 | $CH_3$ | $CH=CHCOOH$ |
| 696 | $CH_3$ | $CH=C(CH_3)COOH$ |
| 697 | $CH_3$ | $CH=C(Cl)COOH$ |
| 698 | $CH_3$ | $CH=C(CN)COOCH_2CH=CH_2$ |
| 699 | $CH_3$ | $CH=C(CN)COOH$ |
| 700 | $CH_3$ | $CH=C(Cl)COOCH_2CH_3$ |
| 701 | $CH_3$ | $CH=C(CH_3)CONH(CH_2CH=CH_2)$ |
| 702 | $CH_3$ | $CH=C(Cl)COSCH_2CH_3$ |
| 703 | $CH_3$ | $CH=C(Cl)CON(CH_3)_2$ |

TABLE 4

Compounds of the formulae $I_{107}$–$I_{136}$, $I_{149}$–$I_{156}$, $II_1$–$II_{13}$, $III_1$–$III_9$, $IV_1$, $IV_2$, $V_1$ and $V_2$

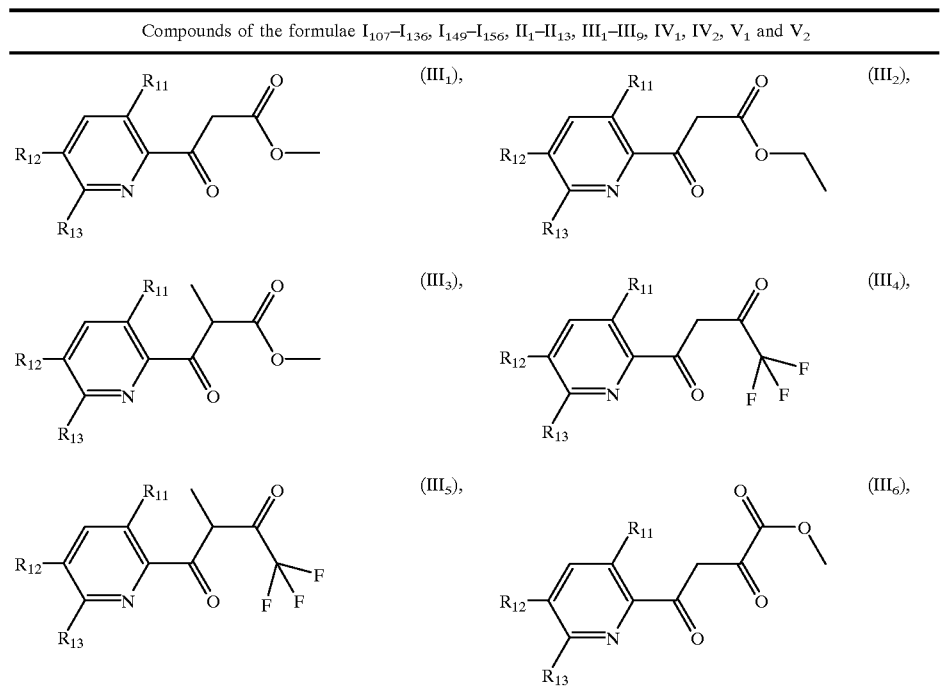

TABLE 4-continued
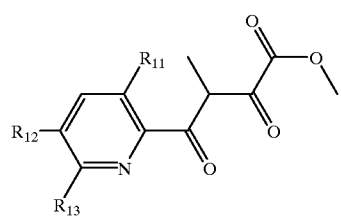 (III₇),
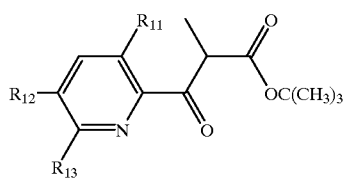 (III₈),
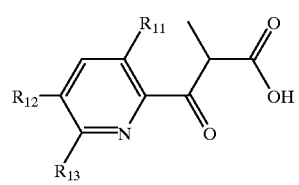 (III₉),
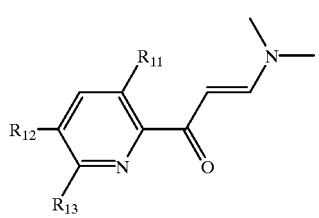 (IV₁),
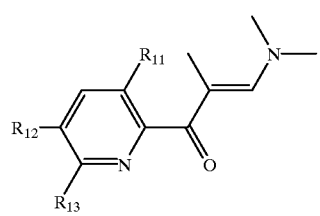 (IV₂),
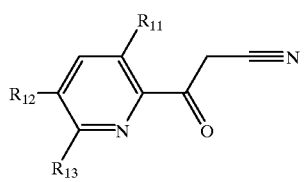 (V₁),
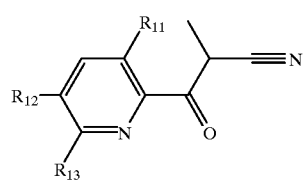 (V₂),
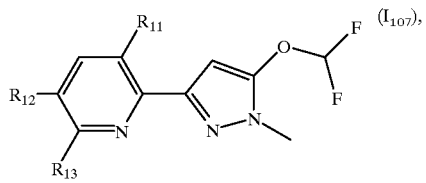 (I₁₀₇),
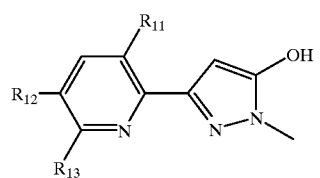 (I₁₀₈),
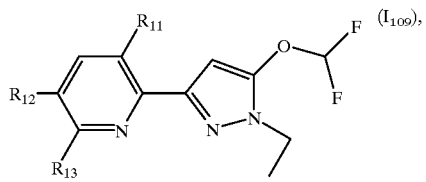 (I₁₀₉),
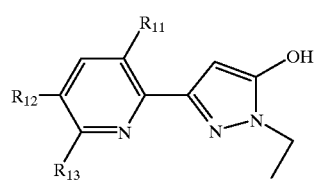 (I₁₁₀),
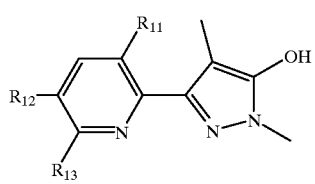 (I₁₁₁),
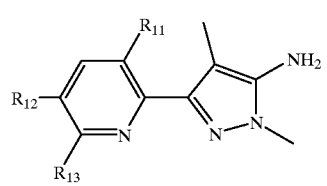 (I₁₁₂),
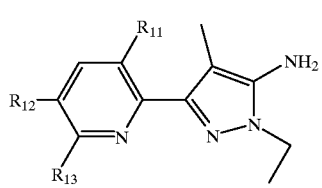 (I₁₁₃),

TABLE 4-continued
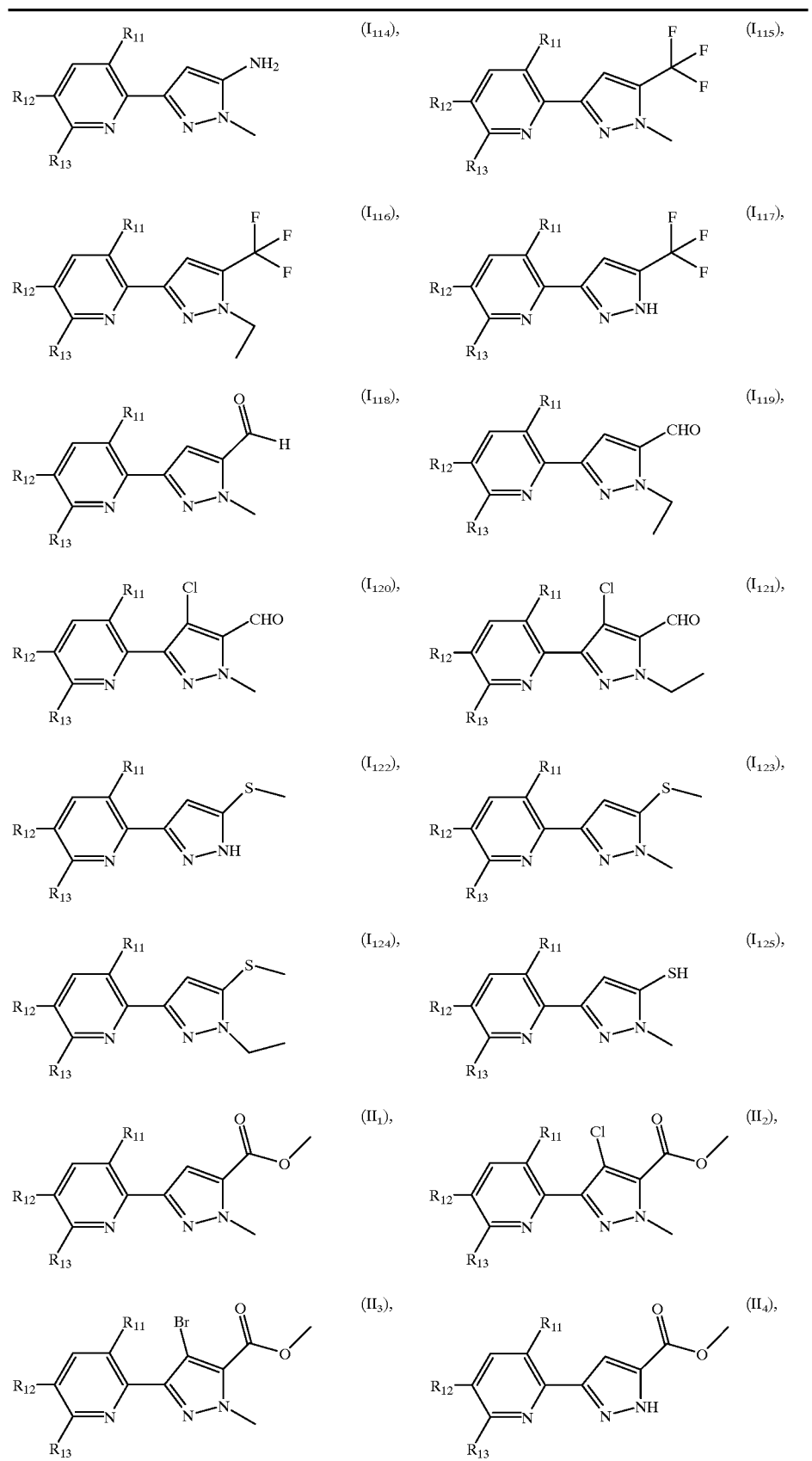

TABLE 4-continued
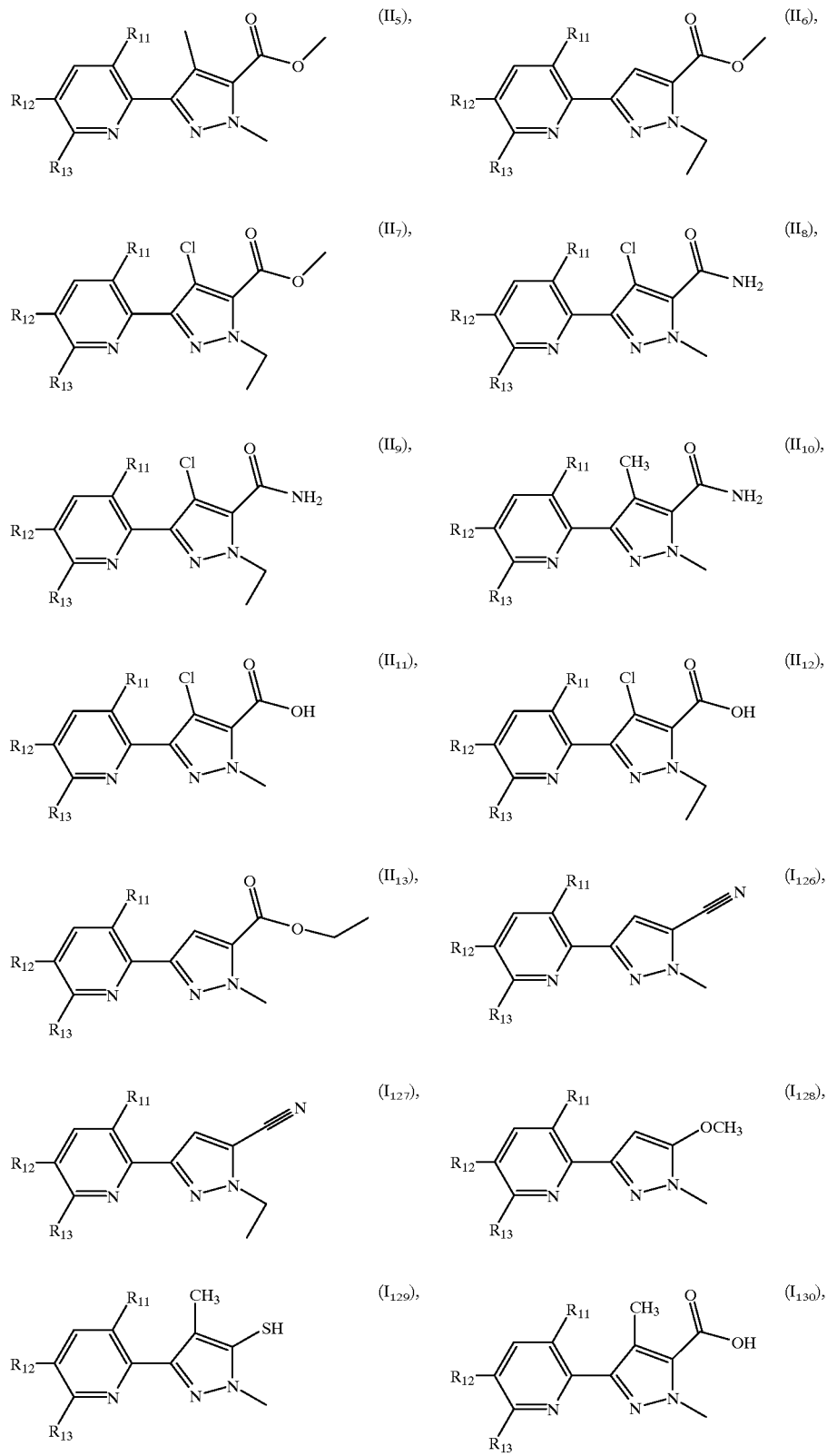

TABLE 4-continued
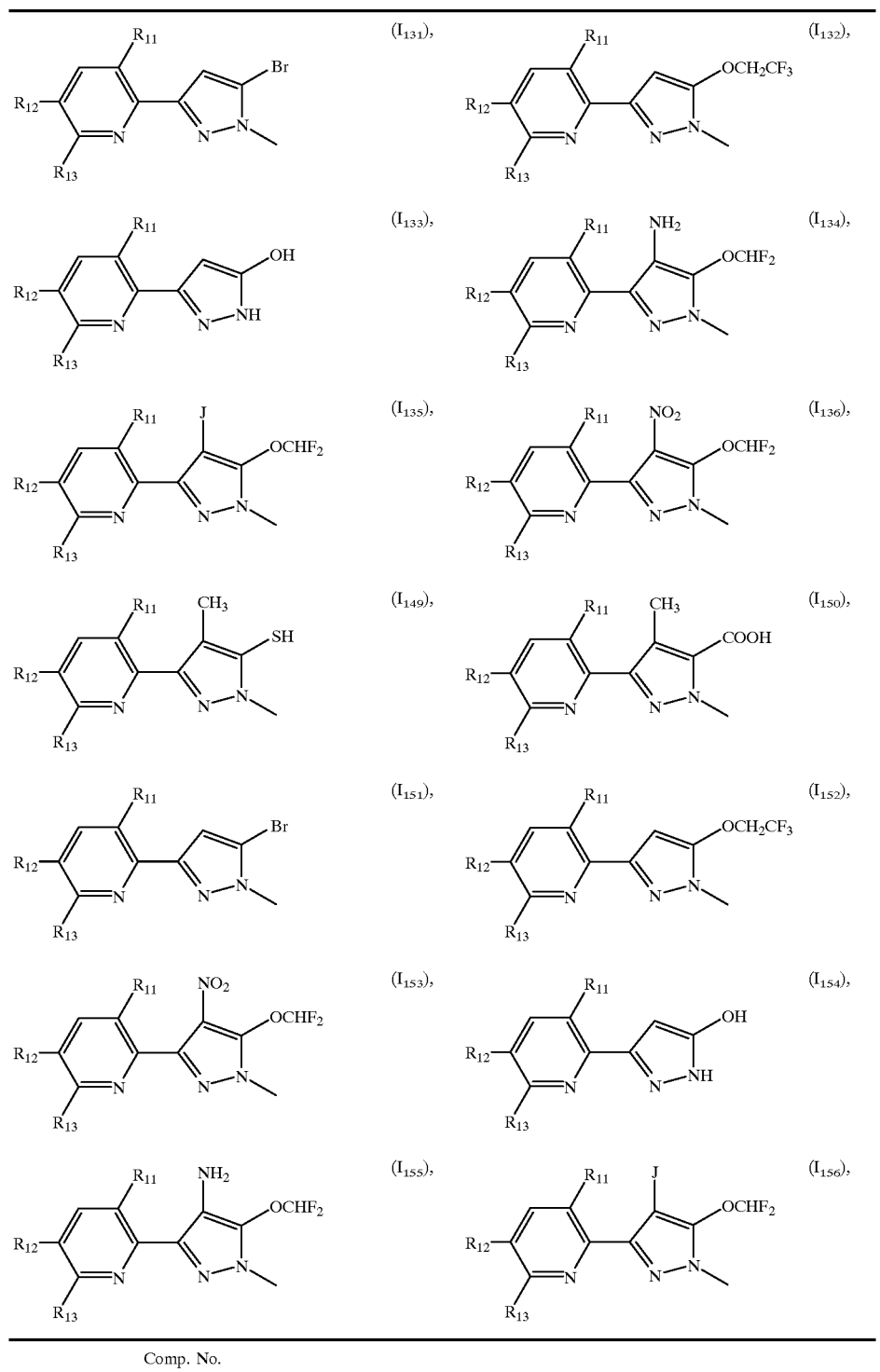
| Comp. No.<br>$I_{107}$–$I_{136}$; $I_{149}$–$I_{156}$;<br>$II_1$–$II_{13}$; $III_1$–$III_9$;<br>$IV_1$, $IV_2$; $V_1$, $V_2$ | $R_{11}$ | $R_{12}$ | $R_{13}$ |
|---|---|---|---|
| 001 | H | Cl | H |
| 002 | H | Cl | $CH_3$ |
| 003 | H | Cl | COOH |
| 004 | H | Cl | $COOCH_3$ |
| 005 | H | Cl | $COOCH_2CH_3$ |
| 006 | H | Cl | $COOCH_2C_6H_5$ |
| 007 | H | Cl | OH |

TABLE 4-continued

| | | | |
|---|---|---|---|
| 008 | H | Cl | OCH$_3$ |
| 009 | H | Cl | OCH$_2$C$_6$H$_5$ |
| 010 | H | Cl | OCH$_2$COOH |
| 011 | H | Cl | F |
| 012 | H | Cl | Cl |
| 013 | H | Cl | Br |
| 014 | H | Cl | NH$_2$ |
| 015 | H | Cl | NHCOCH$_3$ |
| 016 | H | Cl | SH |
| 017 | H | Cl | SCH$_3$ |
| 018 | H | Br | H |
| 019 | H | Br | CH$_3$ |
| 020 | H | Br | COOH |
| 021 | H | Br | COOCH$_3$ |
| 022 | H | Br | COOCH$_2$CH$_3$ |
| 023 | H | Br | COOCH$_2$C$_6$H$_5$ |
| 024 | H | Br | OH |
| 025 | H | Br | OCH$_3$ |
| 026 | H | Br | OCH$_2$C$_6$H$_5$ |
| 027 | H | Br | OCH$_2$COOH |
| 028 | H | Br | F |
| 029 | H | Br | Cl |
| 030 | H | Br | Br |
| 031 | H | Br | NH$_2$ |
| 032 | H | Br | NHCOCH$_3$ |
| 033 | H | Br | SH |
| 034 | H | Br | SCH$_3$ |
| 035 | F | Cl | H |
| 036 | F | Cl | CH$_3$ |
| 037 | F | Cl | COOH |
| 038 | F | Cl | COOCH$_3$ |
| 039 | F | Cl | COOCH$_2$CH$_3$ |
| 040 | F | Cl | COOCH$_2$C$_6$H$_5$ |
| 041 | F | Cl | OH |
| 042 | F | Cl | OCH$_3$ |
| 043 | F | Cl | OCH$_2$C$_6$H$_5$ |
| 044 | F | Cl | OCH$_2$COOH |
| 045 | F | Cl | F |
| 046 | F | Cl | Cl |
| 047 | F | Cl | Br |
| 048 | F | Cl | NH$_2$ |
| 049 | F | Cl | NHCOCH$_3$ |
| 050 | F | Cl | SH |
| 051 | F | Cl | SCH$_3$ |
| 052 | Cl | Cl | H |
| 053 | Cl | Cl | CH$_3$ |
| 054 | Cl | Cl | COOH |
| 055 | Cl | Cl | COOCH$_3$ |
| 056 | Cl | Cl | COOCH$_2$CH$_3$ |
| 057 | Cl | Cl | COOCH$_2$C$_6$H$_5$ |
| 058 | Cl | Cl | OH |
| 059 | Cl | Cl | OCH$_3$ |
| 060 | Cl | Cl | OCH$_2$C$_6$H$_5$ |
| 061 | Cl | Cl | OCH$_2$COOH |
| 062 | Cl | Cl | F |
| 063 | Cl | Cl | Cl |
| 064 | Cl | Cl | Br |
| 065 | Cl | Cl | NH$_2$ |
| 066 | Cl | Cl | NHCOCH$_3$ |
| 067 | Cl | Cl | SH |
| 068 | Cl | Cl | SCH$_3$ |
| 069 | F | Br | H |
| 070 | F | Br | CH$_3$ |
| 071 | F | Br | COOH |
| 072 | F | Br | COOCH$_3$ |
| 073 | F | Br | COOCH$_2$CH$_3$ |
| 074 | F | Br | COOCH$_2$C$_6$H$_5$ |
| 075 | F | Br | OH |
| 076 | F | Br | OCH$_3$ |
| 077 | F | Br | OCH$_2$C$_6$H$_5$ |
| 078 | F | Br | OCH$_2$COOH |
| 079 | F | Br | F |
| 080 | F | Br | Cl |
| 081 | F | Br | Br |
| 082 | F | Br | NH$_2$ |
| 083 | F | Br | NHCOCH$_3$ |
| 084 | F | Br | SH |
| 085 | F | Br | SCH$_3$ |
| 086 | F | CH$_3$ | H |

TABLE 4-continued

| | | | |
|---|---|---|---|
| 087 | F | $CH_3$ | $CH_3$ |
| 088 | F | $CH_3$ | COOH |
| 089 | F | $CH_3$ | $COOCH_3$ |
| 090 | F | $CH_3$ | $COOCH_2CH_3$ |
| 091 | F | $CH_3$ | $COOCH_2C_6H_5$ |
| 092 | F | $CH_3$ | OH |
| 093 | F | $CH_3$ | $OCH_3$ |
| 094 | F | $CH_3$ | $OCH_2C_6H_5$ |
| 095 | F | $CH_3$ | $OCH_2COOH$ |
| 096 | F | $CH_3$ | F |
| 097 | F | $CH_3$ | Cl |
| 098 | F | $CH_3$ | Br |
| 099 | F | $CH_3$ | $NH_2$ |
| 100 | F | $CH_3$ | $NHCOCH_3$ |
| 101 | F | $CH_3$ | SH |
| 102 | F | $CH_3$ | $SCH_3$ |
| 103 | Cl | $CF_3$ | H |
| 104 | Cl | $CF_3$ | $CH_3$ |
| 105 | Cl | $CF_3$ | COOH |
| 106 | Cl | $CF_3$ | $COOCH_3$ |
| 107 | Cl | $CF_3$ | $COOCH_2CH_3$ |
| 108 | Cl | $CF_3$ | $COOCH_2C_6H_5$ |
| 109 | Cl | $CF_3$ | OH |
| 110 | Cl | $CF_3$ | $OCH_3$ |
| 111 | Cl | $CF_3$ | $OCH_2C_6H_5$ |
| 112 | Cl | $CF_3$ | $OCH_2COOH$ |
| 113 | Cl | $CF_3$ | F |
| 114 | Cl | $CF_3$ | Cl |
| 115 | Cl | $CF_3$ | Br |
| 116 | Cl | $CF_3$ | $NH_2$ |
| 117 | Cl | $CF_3$ | $NHCOCH_3$ |
| 118 | Cl | $CF_3$ | SH |
| 119 | Cl | $CF_3$ | $SCH_3$ |
| 120 | Cl | $CHF_2$ | H |
| 121 | Cl | $CHF_2$ | $CH_3$ |
| 122 | Cl | $CHF_2$ | COOH |
| 123 | Cl | $CHF_2$ | $COOCH_3$ |
| 124 | Cl | $CHF_2$ | $COOCH_2CH_3$ |
| 125 | Cl | $CHF_2$ | $COOCH_2C_6H_5$ |
| 126 | Cl | $CHF_2$ | OH |
| 127 | Cl | $CHF_2$ | $OCH_3$ |
| 128 | Cl | $CHF_2$ | $OCH_2C_6H_5$ |
| 129 | Cl | $CHF_2$ | $OCH_2COOH$ |
| 130 | Cl | $CHF_2$ | F |
| 131 | Cl | $CHF_2$ | Cl |
| 132 | Cl | $CHF_2$ | Br |
| 133 | Cl | $CHF_2$ | $NH_2$ |
| 134 | Cl | $CHF_2$ | $NHCOCH_3$ |
| 135 | Cl | $CHF_2$ | SH |
| 136 | Cl | $CHF_2$ | $SCH_3$ |
| 137 | Cl | $CH_3$ | H |
| 138 | Cl | $CH_3$ | $CH_3$ |
| 139 | Cl | $CH_3$ | COOH |
| 140 | Cl | $CH_3$ | $COOCH_3$ |
| 141 | Cl | $CH_3$ | $COOCH_2CH_3$ |
| 142 | Cl | $CH_3$ | $COOCH_2C_6H_5$ |
| 143 | Cl | $CH_3$ | OH |
| 144 | Cl | $CH_3$ | $OCH_3$ |
| 145 | Cl | $CH_3$ | $OCH_2C_6H_5$ |
| 146 | Cl | $CH_3$ | $OCH_2COOH$ |
| 147 | Cl | $CH_3$ | F |
| 148 | Cl | $CH_3$ | Cl |
| 149 | Cl | $CH_3$ | Br |
| 150 | Cl | $CH_3$ | $NH_2$ |
| 151 | Cl | $CH_3$ | $NHCOCH_3$ |
| 152 | Cl | $CH_3$ | SH |
| 153 | Cl | $CH_3$ | $SCH_3$ |
| 154 | Cl | CHO | H |
| 155 | Cl | CHO | $CH_3$ |
| 156 | Cl | CHO | COOH |
| 157 | Cl | CHO | $COOCH_3$ |
| 158 | Cl | CHO | $COOCH_2CH_3$ |
| 159 | Cl | CHO | $COOCH_2C_6H_5$ |
| 160 | Cl | CHO | OH |
| 161 | Cl | CHO | $OCH_3$ |
| 162 | Cl | CHO | $OCH_2C_6H_5$ |
| 163 | Cl | CHO | $OCH_2COOH$ |
| 164 | Cl | CHO | F |
| 165 | Cl | CHO | Cl |

TABLE 4-continued

| | | | |
|---|---|---|---|
| 166 | Cl | CHO | Br |
| 167 | Cl | CHO | $NH_2$ |
| 168 | Cl | CHO | $NHCOCH_3$ |
| 169 | Cl | CHO | SH |
| 170 | Cl | CHO | $SCH_3$ |
| 171 | F | CHO | H |
| 172 | F | CHO | $CH_3$ |
| 173 | F | CHO | COOH |
| 174 | F | CHO | $COOCH_3$ |
| 175 | F | CHO | $COOCH_2CH_3$ |
| 176 | F | CHO | $COOCH_2C_6H_5$ |
| 177 | F | CHO | OH |
| 178 | F | CHO | $OCH_3$ |
| 179 | F | CHO | $OCH_2C_6H_5$ |
| 180 | F | CHO | $OCH_2COOH$ |
| 181 | F | CHO | F |
| 182 | F | CHO | Cl |
| 183 | F | CHO | Br |
| 184 | F | CHO | $NH_2$ |
| 185 | F | CHO | $NHCOCH_3$ |
| 186 | F | CHO | SH |
| 187 | F | CHO | $SCH_3$ |

TABLE 5

Compounds prepared, from the preceding Tables 1–4, with physico-chemical data.

| Comp.No. | Physico-chemical data |
|---|---|
| $I_1.002$ | Melting point 95–96° C. |
| $I_1.003$ | Melting point 63–67° C. |
| $I_1.005$ | Melting point 126–128° C. |
| $I_1.007$ | Melting point 76–77° C. |
| $I_1.009$ | Melting point 133–134° C. |
| $I_1.022$ | Melting point 149–150° C. |
| $I_1.023$ | Melting point 82–83° C. |
| $I_1.024$ | Melting point 80–81° C. |
| $I_1.026$ | Solid |
| $I_1.028$ | Melting point 122–123° C. |
| $I_1.031$ | Melting point 71–75° C. |
| $I_1.046$ | Melting point 78–79° C. |
| $I_1.088$ | Melting point 63–64° C. |
| $I_1.113$ | Melting point 120–121° C. |
| $I_1.114$ | Melting point 114–115° C. |
| $I_1.115$ | Melting point 82–85° C. |
| $I_1.119$ | Solid |
| $I_1.120$ | Melting point 83–84° C. |
| $I_1.121$ | $^1$H-NMR (CDCl$_3$): 7.70 ppm (d, 1H); 6.73 ppm (t, 1H); 4.48 ppm (q, 2H); 3.89 ppm (s, 3H); 1.43 ppm (t, 3H); solid |
| $I_1.122$ | Resin |
| $I_1.132$ | Resin |
| $I_1.134$ | Melting point 108–110° C. |
| $I_1.154$ | Amorphous |
| $I_1.157$ | Resin |
| $I_1.159$ | Melting point 79–81° C. |
| $I_1.164$ | Melting point 81–82° C. |
| $I_1.168$ | Solid |
| $I_1.177$ | Melting point 94–95° C. |
| $I_1.190$ | Melting point 92–94° C. |
| $I_1.243$ | Melting point 88–89° C. |
| $I_1.393$ | Melting point 133–134° C. |
| $I_1.735$ | Meltng point 81–84° C. |
| $I_1.736$ | Melting point 74–76° C. |
| $I_1.737$ | Solid |
| $I_1.738$ | Melting point 76–79° C. |
| $I_1.739$ | Resin |
| $I_1.740$ | Melting point 75–77° C. |
| $I_1.741$ | Melting point 115–116° C. |
| $I_1.742$ | Solid |
| $I_1.743$ | Solid |
| $I_1.744$ | Solid |
| $I_1.745$ | Melting point 79–80° C. |
| $I_1.746$ | Melting point 83–84° C. |
| $I_1.747$ | Melting point 138–139° C. |
| $I_1.748$ | Melting point 76–77° C. |
| $I_1.749$ | Melting point 147–149° C. |
| $I_1.750$ | Melting point 57–62° C. |
| $I_1.751$ | Resin |
| $I_1.752$ | Resin |
| $I_1.753$ | Melting point 134–136° C. |
| $I_1.754$ | Resin |
| $I_1.755$ | Melting point 42–44° C. |
| $I_1.756$ | Melting point 115–116° C. |
| $I_1.757$ | Melting point 57–59° C. |
| $I_1.758$ | Resin |
| $I_1.759$ | Resin |
| $I_1.760$ | Resin |
| $I_1.761$ | Melting point 83–84° C. |
| $I_1.764$ | Isomer A: resin; isomer B: melting point 89–91° C. |
| $I_1.805$ | Amorphous |
| $I_1.806$ | Melting point 84–88° C. |
| $I_1.807$ | Melting point 84–86° C. |
| $I_1.808$ | Melting point 108–109° C. |
| $I_4.002$ | Melting point 76–78° C. |
| $I_4.022$ | Solid |
| $I_4.028$ | Melting point 98–101° C. |
| $I_4.121$ | Melting point 82–83° C. |
| $I_4.243$ | Resin |
| $I_4.484$ | Solid |
| $I_4.485$ | Solid |
| $I_4.498$ | Solid |
| $I_4.566$ | Solid |
| $I_4.570$ | Solid |
| $I_4.729$ | Solid |
| $I_4.733$ | Solid |
| $I_6.002$ | Melting point 80–81° C. |
| $I_6.028$ | Melting point 108–110° C. |
| $I_6.121$ | Melting point 88–89° C. |
| $I_9.002$ | Melting point 130–132° C. |
| $I_9.121$ | Melting point 137–140° C. |
| $I_{10}.002$ | Melting point 144–146° C. |
| $I_{18}.002$ | Melting point 61–64° C. |
| $I_{18}.243$ | Oil |
| $I_{19}.002$ | Melting point 112–114° C. |
| $I_{19}.243$ | Melting point 92–93° C. |
| $I_{20}.002$ | Melting point 145–147° C. |
| $I_{20}.243$ | Melting point 120–135° C. |
| $I_{30}.002$ | Oil |

TABLE 5-continued

Compounds prepared, from the preceding Tables 1–4, with physico-chemical data.

| Comp.No. | Physico-chemical data |
| --- | --- |
| $I_{30}.243$ | Melting point 49–53° C. |
| $I_{31}.243$ | Melting point 105–108° C. |
| $I_{32}.002$ | Melting point 154–157° C. |
| $I_{32}.243$ | Melting point 107–112° C. |
| $I_{63}.001$ | Solid |
| $I_{68}.002$ | Melting point 115–117° C. |
| $I_{68}.003$ | Melting point 114–118° C. |
| $I_{70}.153$ | Melting point 85–89° C. |
| $I_{71}.002$ | Melting point 81–83° C. |
| $I_{71}.023$ | Melting point 108–110° C. |
| $I_{73}.002$ | Melting point 56–58° C. |
| $I_{73}.023$ | Melting point 100–102° C. |
| $I_{75}.002$ | Melting point 159–161° C. |
| $I_{75}.473$ | Solid |
| $I_{76}.002$ | Solid |
| $I_{97}.002$ | Melting point 174–176° C. |
| $I_{103}.002$ | Melting point 79–80° C. |
| $I_{104}.002$ | Melting point 111–116° C. |
| $I_{105}.002$ | Melting point 77–79° C. |
| $I_{106}.002$ | Melting point 96–97° C. |
| $I_{107}.035$ | Melting point 86–88° C. |
| $I_{108}.035$ | Solid |
| $I_{108}.052$ | Melting point 148–152° C. |
| $I_{109}.035$ | Melting point 83–85° C. |
| $I_{110}.035$ | Melting point 161–163° C. |
| $I_{110}.052$ | Solid |
| $I_{115}.035$ | Melting point 92–94° C. |
| $I_{128}.035$ | Melting point 84–86° C. |
| $I_{129}.103$ | Resin |
| $I_{129}.052$ | Melting point 104–105° C. |
| $I_{130}.035$ | Melting point 194–196° C. |
| $I_{131}.035$ | Melting point 110–111° C. |
| $I_{132}.035$ | Melting point 72–73° C. |
| $I_{133}.035$ | Solid |
| $I_{134}.035$ | Melting point 92–94° C. |
| $I_{135}.035$ | Melting point 77–78° C. |
| $I_{136}.035$ | Melting point 108–109° C. |
| $I_{137}.002$ | Melting point 80–82° C. |
| $I_{138}.002$ | Melting point 47–49° C. |
| $I_{139}.002$ | Melting point 118–122° C. |
| $I_{144}.002$ | Melting point 132–133° C. |
| $I_{145}.002$ | Melting point 83–84° C. |
| $I_{146}.002$ | Melting point 95–96° C. |
| $I_{147}.101$ | Melting point 153–154° C. |
| $II_5.035$ | Melting point 99–100° C. |
| $II_{10}.035$ | Melting point 201–204° C. |
| $II_{13}.035$ | Melting point 117–118° C. |
| $III_1.035$ | TLC analysis (silica gel 60 $F_{254}$; n-hexane/AcOEt/AcOH 20/20/1: Rf-value 0.59 |
| $III_1.052$ | TLC analysis (silica gel 60 $F_{254}$; n-hexane/AcOEt/AcOH 20/20/1: Rf-value 0.67 |
| $III_4.001$ | TLC analysis (silica gel 60 $F_{254}$; n-hexane/AcOEt/AcOH 40/20/1: Rf-value 0.33 |
| $III_4.103$ | TLC analysis (silica gel 60 $F_{254}$; n-hexane/AcOEt/AcOH 20/20/1: Rf-value 0.47 |

Formulation examples for active substances of the formula I (%=per cent by weight

| F1. Emulsion concentrates | a) | b) | c) | d) |
| --- | --- | --- | --- | --- |
| Active substance according to Tables 1–4 | 5% | 10% | 25% | 50% |
| Calcium dodecylbenzene-sulfonate | 6% | 8% | 6% | 8% |
| Castor oil polyglycol ether (36 mol of EO) | 4% | — | 4% | 4% |
| Octylphenol polyglycol ether (7–8 mol of EO) | — | 4% | — | 2% |
| Cyclohexanone | — | — | 10% | 20% |
| Aromatic hydrocarbon mixture $C_9$–$C_{12}$ | 85% | 78% | 55% | 16% |

Emulsions of any desired concentration can be prepared from such concentrates by dilution with water.

| F2. Solutions | a) | b) | c) | d) |
| --- | --- | --- | --- | --- |
| Active substance according to Tables 1–4 | 5% | 10% | 25% | 50% |
| 1-Methoxy-3-(3-methoxy-propoxy)propane | — | 20% | 20% | — |
| Polyethylene glycol molecular weight 400 | 20% | 10% | — | — |
| N-Methyl-2-pyrrolidone | — | — | 30% | 10% |
| Aromatic hydrocarbon mixture $C_9$–$C_{12}$ | 75% | 60% | — | — |

The solutions are suitable for use in the form of tiny drops.

| F3. Wettable powders | a) | b) | c) | d) |
| --- | --- | --- | --- | --- |
| Active substance according to Tables 1–4 | 5% | 25% | 50% | 80% |
| Sodium ligninsulfonate | 4% | — | 3% | — |
| Sodium lauryl sulfate | 2% | 3% | — | 4% |
| Sodium diisobutyl-naphthalene-sulfonate | — | 6% | 5% | 6% |
| Octytphenol polyglycol ether (7–8 mol of EO) | — | 1% | 2% | — |
| Highly disperse silicic acid | 1% | 3% | 5% | 10% |
| Kaolin | 88% | 62% | 35% | — |

The active substance is mixed thoroughly with the additives and the mixture is ground thoroughly in a suitable mill. Wettable powders which can be diluted with water to give suspensions of any desired concentration are obtained.

| F4. Coated granules | a) | b) | c) |
| --- | --- | --- | --- |
| Active substance according to Tables 1–4 | 0.1% | 5% | 15% |
| Highly disperse silicic acid | 0.9% | 2% | 2% |
| Inorganic carrier material (Ø 0.1–1 mm), for example $CaCO_3$ or $SiO_2$ | 9.0% | 93% | 83% |

The active substance is dissolved in methylene chloride, the solution is sprayed onto the carrier and the solvent is then evaporated off in vacuo.

| F5. Coated granules | a) | b) | c) |
| --- | --- | --- | --- |
| Active substance according to Tables 1–4 | 0.1% | 5% | 15% |
| Polyethylene glycol molecular weight 200 | 1.0% | 2% | 3% |
| Highly disperse silicic acid | 0.9% | 1% | 2% |

-continued

| F5. Coated granules | a) | b) | c) |
|---|---|---|---|
| Inorganic carrier material (Ø 0.1–1 mm) for example $CaCO_3$ or $SiO_2$ | 98.0% | 92% | 80% |

The finely ground active substance is applied uniformly to the carrier material, which has been moistened with polyethylene glycol, in a mixer. Dust-free coated granules are obtained in this manner.

| F6. Extruded granules | a) | b) | c) | d) |
|---|---|---|---|---|
| Active substance according to Tables 1–4 | 0.1% | 3% | 5% | 15% |
| Sodium ligninsulfonate | 1.5% | 2% | 3% | 4% |
| Carboxymethylcellulose | 1.4% | 2% | 2% | — |
| Kaolin | 97.0% | 93% | 90% | 79% |

The active substance is mixed with the additives and the mixture is ground and moistened with water. This mixture is extruded and then dried in a stream of air.

| F7. Dusts | a) | b) | c) |
|---|---|---|---|
| Active substance according to Tables 1–4 | 0.1% | 1% | 5% |
| Talc | 39.9% | 49% | 35% |
| Kaolin | 60.0% | 50% | 60% |

Ready-to use dusts are obtained by mixing the active substance with the carriers and grinding the mixture on a suitable mill.

| F8. Suspension concentrates | a) | b) | c) | d) |
|---|---|---|---|---|
| Active substance according to Tables 1–4 | 3% | 10% | 25% | 50% |
| Ethylene glycol | 5% | 5% | 5% | 5% |
| Nonylphenol polyglycol ether (15 mol of EO) | — | 1% | 2% | — |
| Sodium ligninsulfonate | 3% | 3% | 4% | 5% |
| Carboxymethylcellulose | 1% | 1% | 1% | 1% |
| 37% aqueous formaldehyde solution | 0.2% | 0.2% | 0.2% | 0.2% |
| Silicone oil emulsion | 0.8% | 0.8% | 0.8% | 0.8% |
| Water | 87% | 79% | 62% | 38% |

The finely ground active substance is mixed intimately with the additives. A suspension concentrate from which suspensions of any desired concentration can be prepared by dilution with water is thus obtained.

BIOLOGICAL EXAMPLES

Example B1

Herbicidal action before emergence of the plants (pre-emergence action)

Monocotyledon and dicotyledon test plants are sown in standard soil in plastic pots. Immediately after sowing, the test substances are sprayed on (500 l of water/ha) as an aqueous suspension or emulsion prepared from a 25% emulsion concentrate (Example F1, c)), corresponding to a dosage of 2000 g of AS/ha. The test plants are then grown under optimum conditions in a greenhouse. After a test period of 3 weeks, the test is evaluated with a 9-level scale of ratings (1=complete damage, 9=no action). Ratings of 1 to 4 (in particular 1 to 3) mean a good to very good herbicidal action.

Test plants: Setaria, Solanum

The compounds according to the invention show a good herbicidal action.

Table B1 gives examples of the good herbicidal activity of the compounds of the formual I.

TABLE B1

Pre-emergence action:

| Test plants: | Setaria | Solanum | Dose [g of AS/ha] |
|---|---|---|---|
| Active substance No. | | | |
| $I_1.002$ | 1 | 1 | 2000 |
| $I_1.003$ | 1 | 1 | 500 |
| $I_1.005$ | 2 | 1 | 2000 |
| $I_1.007$ | 1 | 1 | 2000 |
| $I_1.009$ | 1 | 1 | 2000 |
| $I_1.022$ | 1 | 1 | 2000 |
| $I_1.023$ | 1 | 1 | 2000 |
| $I_1.024$ | 1 | 1 | 2000 |
| $I_1.026$ | 1 | 1 | 2000 |
| $I_1.028$ | 1 | 1 | 2000 |
| $I_1.031$ | 1 | 1 | 2000 |
| $I_1.046$ | 1 | 1 | 2000 |
| $I_1.088$ | 1 | 1 | 2000 |
| $I_1.113$ | 1 | 1 | 2000 |
| $I_1.119$ | 1 | 1 | 2000 |
| $I_1.120$ | 1 | 1 | 2000 |
| $I_1.121$ | 1 | 1 | 2000 |
| $I_1.122$ | 1 | 1 | 2000 |
| $I_1.134$ | 1 | 1 | 2000 |
| $I_1.154$ | 1 | 1 | 2000 |
| $1_1.157$ | 1 | 1 | 2000 |
| $I_1.159$ | 1 | 1 | 2000 |
| $I_1.164$ | 1 | 1 | 2000 |
| $I_1.168$ | 1 | 1 | 2000 |
| $I_1.243$ | 1 | 1 | 2000 |
| $I_1.393$ | 1 | 1 | 2000 |
| $I_1.735$ | 1 | 2 | 2000 |
| $I_1.736$ | 1 | 1 | 2000 |
| $I_1.737$ | 3 | 1 | 2000 |
| $I_1.738$ | 1 | 1 | 2000 |
| $I_1.739$ | 1 | 1 | 2000 |
| $I_1.740$ | 1 | 1 | 2000 |
| $I_1.741$ | 1 | 1 | 2000 |
| $I_1.745$ | 1 | 1 | 2000 |
| $I_1.746$ | 1 | 4 | 2000 |
| $I_1.747$ | 1 | 1 | 2000 |
| $I_1.748$ | 1 | 1 | 2000 |
| $I_1.749$ | 5 | 2 | 2000 |
| $I_1.750$ | 1 | 1 | 2000 |
| $I_4.002$ | 1 | 1 | 2000 |
| $I_4.028$ | 1 | 1 | 2000 |
| $I_4.121$ | 1 | 1 | 2000 |
| $I_4.484$ | 1 | 1 | 2000 |
| $I_4.485$ | 1 | 1 | 2000 |
| $I_4.498$ | 2 | 1 | 2000 |
| $I_4.566$ | 2 | 1 | 2000 |
| $I_4.570$ | 1 | 1 | 2000 |
| $I_6.002$ | 1 | 1 | 2000 |
| $I_6.028$ | 1 | 1 | 2000 |
| $I_6.121$ | 1 | 1 | 2000 |
| $I_9.002$ | 1 | 1 | 2000 |
| $I_9.121$ | 2 | 3 | 2000 |
| $I_{10}.002$ | 1 | 1 | 2000 |
| $I_{20}.002$ | 1 | 1 | 2000 |
| $I_{63}.001$ | 1 | 1 | 2000 |
| $I_{68}.002$ | 1 | 1 | 2000 |
| $I_{68}.003$ | 1 | 1 | 2000 |
| $I_{71}.002$ | 1 | 1 | 2000 |
| $I_{73}.002$ | 1 | 1 | 2000 |

TABLE B1-continued

Pre-emergence action:

| Test plants: | Setaria | Solanum | Dose [g of AS/ha] |
|---|---|---|---|
| $I_{75}$.002 | 2 | 1 | 2000 |
| $I_{75}$.473 | 1 | 1 | 2000 |
| $I_{76}$.002 | 1 | 1 | 2000 |
| $I_{97}$.002 | 3 | 2 | 2000 |
| $I_{103}$.002 | 1 | 1 | 2000 |
| $I_{105}$.002 | 2 | 1 | 2000 |
| $I_{106}$.002 | 2 | 1 | 2000 |
| $I_{136}$.035 | 2 | 3 | 2000 |
| $I_{137}$.002 | 1 | 1 | 2000 |

The same results are obtained if the compounds of the formula I are formulated according to Examples F2 to F8.

Example B2

Post-emergence herbicidal action

Monocotyledon and dicotyledon test plants are grown in plastic pots with standard soil in a greenhouse and, in the 4- to 6-leaf stage, are sprayed with an aqueous suspension or emulsion of the test substances of the formula 1, prepared from a 25% emulsion concentrate (Example F1, c)), corresponding to a dosage of 2000 g of AS/ha (500 l of water/ha). The test plants are then grown further under optimum conditions in a greenhouse. After a test period of about 18 days, the test is evaluated with a 9-level scale of rating (1=complete damage, 9=no action). Ratings of 1 to 4 (in particular 1 to 3) mean a good to very good herbicidal action. Test plants: Setaria, Sinapis, Solanum, Ipomoea The compounds of the formula I also show a potent herbicidal action in this test.

Table B2 gives examples of the good herbicidal activity of the compounds of the formula I.

TABLE B2

Post-emergence action:

| Test plant: | Setaria | Sinapis | Solanum | Ipomoea | Dose [g of AS/ha] |
|---|---|---|---|---|---|
| Active substance No. | | | | | |
| $I_1$.002 | 1 | 1 | 1 | 1 | 2000 |
| $I_1$.003 | 2 | 1 | 1 | 1 | 500 |
| $I_1$.005 | 1 | 1 | 1 | 1 | 2000 |
| $I_1$.007 | 1 | 1 | 1 | 1 | 2000 |
| $I_1$.009 | 5 | 1 | 1 | 1 | 2000 |
| $I_1$.022 | 3 | 1 | 1 | 1 | 2000 |
| $I_1$.023 | 1 | 1 | 1 | 1 | 2000 |
| $I_1$.024 | 2 | 1 | 1 | 1 | 2000 |
| $I_1$.026 | 1 | 1 | 1 | 1 | 2000 |
| $I_1$.028 | 1 | 1 | 1 | 1 | 2000 |
| $I_1$.031 | 3 | 1 | 1 | 1 | 2000 |
| $I_1$.046 | 1 | 1 | 1 | 1 | 2000 |
| $I_1$.088 | 1 | 1 | 1 | 1 | 2000 |
| $I_1$.113 | 1 | 1 | 1 | 1 | 2000 |
| $I_1$.119 | 1 | 1 | 1 | 1 | 2000 |
| $I_1$.120 | 1 | 1 | 1 | 1 | 2000 |
| $I_1$.121 | 1 | 1 | 1 | 1 | 2000 |
| $I_1$.122 | 1 | 1 | 1 | 1 | 2000 |
| $I_1$.134 | 1 | 1 | 1 | 1 | 2000 |
| $I_1$.154 | 1 | 1 | 1 | 1 | 2000 |
| $I_1$.157 | 1 | 1 | 1 | 1 | 2000 |
| $I_1$.159 | 2 | 1 | 1 | 1 | 2000 |
| $I_1$.164 | 1 | 1 | 1 | 1 | 2000 |
| $I_1$.168 | 2 | 1 | 1 | 1 | 2000 |
| $I_1$.243 | 1 | 1 | 1 | 1 | 2000 |

TABLE B2-continued

Post-emergence action:

| Test plant: | Setaria | Sinapis | Solanum | Ipomoea | Dose [g of AS/ha] |
|---|---|---|---|---|---|
| $I_1$.393 | 1 | 1 | 1 | 1 | 2000 |
| $I_1$.735 | 3 | 2 | 1 | 1 | 2000 |
| $I_1$.736 | 1 | 1 | 1 | 1 | 2000 |
| $I_1$.737 | 2 | 1 | 1 | 1 | 2000 |
| $I_1$.738 | 1 | 1 | 1 | 1 | 2000 |
| $I_1$.739 | 1 | 1 | 1 | 1 | 2000 |
| $I_1$.740 | 1 | 1 | 1 | 1 | 2000 |
| $I_1$.741 | 1 | 1 | 1 | 1 | 2000 |
| $I_1$.742 | 1 | 1 | 1 | 1 | 2000 |
| $I_1$.743 | 1 | 1 | 1 | 1 | 2000 |
| $I_1$.744 | 1 | 1 | 1 | 1 | 2000 |
| $I_1$.745 | 4 | 1 | 1 | 1 | 2000 |
| $I_1$.746 | 3 | 2 | 1 | 1 | 2000 |
| $I_1$.747 | 1 | 1 | 1 | 1 | 2000 |
| $I_1$.748 | 3 | 1 | 1 | 1 | 2000 |
| $I_1$.749 | 5 | 2 | 1 | 1 | 2000 |
| $I_1$.750 | 1 | 1 | 1 | 1 | 2000 |
| $I_4$.002 | 6 | 5 | 1 | 1 | 2000 |
| $I_4$.028 | 2 | 1 | 1 | 1 | 2000 |
| $I_4$.121 | 1 | 1 | 1 | 1 | 2000 |
| $I_4$.484 | 4 | 6 | 1 | 1 | 2000 |
| $I_4$.485 | 6 | 2 | 1 | 2 | 2000 |
| $I_4$.570 | 3 | 4 | 1 | 1 | 2000 |
| $I_6$.002 | 6 | 3 | 1 | 1 | 2000 |
| $I_6$.028 | 3 | 1 | 1 | 1 | 2000 |
| $I_6$.121 | 1 | 1 | 1 | 1 | 2000 |
| $I_9$.002 | 2 | 3 | 1 | 1 | 2000 |
| $I_9$.121 | 3 | 3 | 1 | 1 | 2000 |
| $I_{10}$.002 | 5 | 6 | 1 | 1 | 2000 |
| $I_{20}$.002 | 4 | 2 | 1 | 1 | 2000 |
| $I_{63}$.001 | 3 | 1 | 1 | 1 | 2000 |
| $I_{68}$.002 | 1 | 1 | 1 | 1 | 2000 |
| $I_{68}$.003 | 2 | 1 | 1 | 1 | 2000 |
| $I_{71}$.002 | 1 | 1 | 1 | 1 | 2000 |
| $I_{73}$.002 | 1 | 4 | 1 | 1 | 2000 |
| $I_{75}$.002 | 6 | 3 | 2 | 1 | 2000 |
| $I_{75}$.473 | 5 | 4 | 1 | 2 | 2000 |
| $I_{97}$.002 | 5 | 2 | 1 | 1 | 2000 |
| $I_{103}$.002 | 6 | 5 | 1 | 3 | 2000 |
| $I_{105}$.002 | 6 | 5 | 1 | 1 | 2000 |
| $I_{106}$.002 | 3 | 2 | 1 | 1 | 2000 |
| $I_{137}$.002 | 4 | 1 | 1 | 1 | 2000 |

The same results are obtained if the compounds of the formula I are formulated according to Examples F2 to F8.

What is claimed is:

1. A compound of the formula I

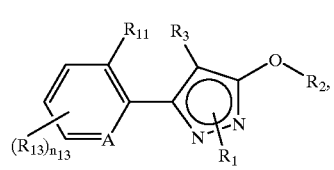

(I)

in which

A is =N— or

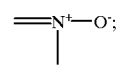

$n_{13}$ is 1, 2 or 3;

$R_1$ is hydrogen, $C_1$–$C_4$alkyl, $C_1$–$C_4$halogenoalkyl, cyano-$C_1$–$C_4$alkyl, $C_3$- or $C_4$alkenyl, $C_3$- or $C_4$halogenoalkenyl, $C_3$- or $C_4$alkynyl or $C_3$–$C_6$cycloalkyl;

$R_2$ is $C_1$–$C_4$halogenoalkyl;

$R_3$ is hydrogen, $C_1$–$C_4$alkyl, $C_1$–$C_4$halogenoalkyl, $C_1$–$C_4$hydroxyalkyl, $C_2$–$C_6$alkenyl, $C_2$–$C_6$halogenoalkenyl, $C_2$–$C_6$alkynyl, halogen, cyano, $NH_2C(S)$—, nitro, OHC— or $R_{18}R_{19}N$—;

$R_{18}$ and $R_{19}$ independently of one another are hydrogen, $C_1$–$C_4$alkyl, $C_1$–$C_4$halogenoalkyl, $C_3$–$C_4$alkenyl, $C_3$–$C_4$halogenoalkenyl, $C_3$–$C_6$cycloalkyl, $C_3$–$C_6$alkynyl, $C_1$–$C_6$alkylcarbonyl, $C_1$–$C_6$halogenoalkylcarbonyl, $C_2$–$C_6$alkenylcarbonyl, $C_2$–$C_6$halogenoalkenylcarbonyl, $C_1$–$C_6$alkylsulfonyl or $C_1$–$C_6$halogenoalkylsulfonyl;

$R_{11}$ is hydrogen, fluorine, chlorine, bromine or methyl;

$R_{13}$ is hydrogen, halogen, cyano, $ClS(O)_2$—, $ClC(O)$—, nitro, amino,

, HS—,

HS—, $R_{20}NH$— or $R_{20}R_{21}N$—;

$R_{20}$ and $R_{21}$ independently of one another are $C_1$–$C_8$alkyl, $C_3$–$C_8$alkenyl, $C_3$–$C_8$alkynyl, $C_3$–$C_6$cycloalkyl, $C_1$–$C_8$halogenoalkyl, $C_3$–$C_8$halogenoalkenyl, $C_1$–$C_4$alkylcarbonyl, $C_1$–$C_4$-halogenoalkylcarbonyl, $C_1$–$C_4$alkylsulfonyl, $C_1$–$C_4$halogenalkylsulfonyl, benzyl or benzyl which is substituted on the phenyl ring once to three times by halogen, $C_1$–$C_4$alkyl or $C_1$–$C_4$halogenoalkyl; or $R_{13}$ is $R_{30}O$—;

$R_{30}$ is hydrogen, $C_1$–$C_8$alkyl, $C_3$–$C_8$alkenyl, $C_3$–$C_8$alkynyl, $C_3$–$C_6$cycloalkyl, $C_1$–$C_8$halogenoalkyl, $C_3$–$C_8$halogenoalkenyl, $C_1$–$C_4$alkoxy-$C_1$–$C_4$alkyl, $C_3$–$C_6$alkenyloxy-$C_1$–$C_4$alkyl, $C_3$–$C_6$alkynyloxy-$C_1$–$C_4$alkyl, $C_1$–$C_4$alkoxy-$C_1$–$C_4$alkoxy-$C_1$–$C_4$alkyl, $C_1$–$C_4$alkylthio-$C_1$–$C_4$alkyl, $C_1$–$C_8$alkoxycarbonyl, $C_3$–$C_8$alkenyloxycarbonyl, benzyloxycarbonyl, phenyl, benzyl, pyridyl, pyrimidinyl, pyrazinyl or pyridazinyl, where these aromatic and heteroaromatic rings mentioned can be unsubstituted or substituted once to three times by halogen, $C_1$–$C_4$alkyl or $C_1$–$C_4$halogenoalkyl; or $R_{30}$ is $R_{31}X_1C(O)$—$C_1$–$C_8$alkyl- or

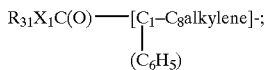

$X_1$ is oxygen, sulfur or

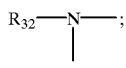;

$R_{31}$ is hydrogen, $C_1$–$C_8$alkyl, $C_3$–$C_8$alkenyl, $C_3$–$C_8$alkynyl, $C_3$–$C_6$cycloalkyl, $C_1$–$C_8$halogenoalkyl, $C_3$–$C_8$halogenoalkenyl, $C_1$–$C_4$alkoxy-$C_1$–$C_4$alkyl, $C_3$–$C_6$alkenyloxy-$C_1$–$C_4$alkyl, $C_1$–$C_4$alkylthio-$C_1$–$C_4$alkyl, phenyl, phenyl which is substituted once to three times by halogen, $C_1$–$C_4$alkyl or $C_1$–$C_4$halogenoalkyl, benzyl or benzyl which is substituted once to three times on the phenyl ring by halogen, $C_1$–$C_4$alkyl or $C_1$–$C_4$halogenoalkyl;

$R_{32}$ is hydrogen, $C_1$–$C_8$alkyl, $C_3$–$C_8$alkenyl, $C_3$–$C_8$alkynyl, $C_3$–$C_6$cycloalkyl or $C_1$–$C_8$-halogenoalkyl; or $R_{13}$ is $R_{33}S(O)_{n2}$—;

$n_2$ is 0, 1 or 2;

$R_{33}$ is $C_1$–$C_8$alkyl, $C_3$–$C_8$alkenyl, $C_3$–$C_8$alkynyl, $C_3$–$C_6$cycloalkyl, $C_1$–$C_8$halogenoalkyl, $C_3$–$C_8$halogenoalkenyl, $C_1$–$C_4$alkoxy-$C_1$–$C_4$alkyl, $C_3$–$C_6$alkenyloxy-$C_1$–$C_4$alkyl, $C_1$–$C_4$alkylthio-$C_1$–$C_4$alkyl, phenyl, phenyl which is substituted once to three times by halogen, $C_1$–$C_4$alkyl or $C_1$–$C_4$halogenoalkyl, benzyl or benzyl which is substituted once to three times on the phenyl ring by halogen, $C_1$–$C_4$alkyl or $C_1$–$C_4$halogenoalkyl, and, if $n_2$ is 0, $R_{33}$ is hydrogen, $C_1$–$C_8$alkylcarbonyl or $R_{34}X_2C(O)$—;

$X_2$ is oxygen, sulfur or

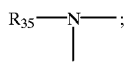

$R_{34}$ is hydrogen, $C_1$–$C_8$alkyl, $C_3$–$C_8$alkenyl, $C_3$–$C_8$alkynyl, $C_3$–$C_6$cycloalkyl, $C_1$–$C_8$-halogenoalkyl, $C_3$–$C_8$halogenoalkenyl, $C_1$–$C_4$alkoxy-$C_1$–$C_4$alkyl, $C_3$–$C_6$alkenyloxy-$C_1$–$C_4$alkyl, $C_1$–$C_4$alkylthio-$C_1$–$C_4$alkyl, phenyl, phenyl which is substituted once to three times by halogen, $C_1$–$C_4$alkyl or $C_1$–$C_4$halogenoalkyl, benzyl or benzyl which is substituted once to three times on the phenyl ring by halogen, $C_1$–$C_4$alkyl or $C_1$–$C_4$halogenoalkyl;

$R_{35}$ is hydrogen, $C_1$–$C_8$alkyl or $C_3$–$C_8$alkenyl; or $R_{13}$ is $R_{36}R_{37}NS(O)_2$—;

$R_{36}$ is hydrogen, $C_1$–$C_8$alkyl, $C_2$–$C_8$alkenyl, $C_3$–$C_8$alkynyl or $C_3$–$C_6$cycloalkyl;

$R_{37}$ is hydrogen, $C_1$–$C_8$alkyl, $C_3$–$C_8$alkenyl, $C_3$–$C_8$alkynyl, $C_1$–$C_8$halogenoalkyl, $C_1$–$C_4$-alkylcarbonyl, $C_1$–$C_4$halogenoalkylcarbonyl, benzoyl or benzoyl which is substituted once to three times on the phenyl ring by halogen, $C_1$–$C_4$alkyl or $C_1$–$C_4$halogenoalkyl;

$R_{13}$ is $R_{40}C(O)$—;

$R_{40}$ is hydrogen, fluorine, chlorine, $C_1$–$C_8$alkyl, $C_2$–$C_8$alkenyl, $C_2$–$C_8$alkynyl, $C_3$–$C_6$cycloalkyl, $C_1$–$C_8$halogenoalkyl, cyano-$C_1$–$C_4$alkyl, $C_2$–$C_8$halogenoalkenyl, $C_1$–$C_4$alkoxy-$C_1$–$C_4$alkyl, $C_3$–$C_6$alkenyloxy-$C_1$–$C_4$alkyl, $C_1$–$C_4$alkylthio-$C_1$–$C_4$alkyl, phenyl, phenyl which is substituted once to three times by halogen, $C_1$–$C_4$alkyl or $C_1$–$C_4$halogenoalkyl, benzyl or benzyl which is substituted once to three times on the phenyl ring by halogen, $C_1$–$C_4$alkyl or $C_1$–$C_4$-halogeno-alkyl; or $R_{13}$ is $R_{50}X_3C(O)$—;

$X_3$ is oxygen, sulfur,

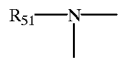 or 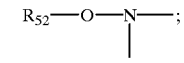

$R_{50}$ is hydrogen, $C_1$–$C_8$alkyl, $C_3$–$C_8$alkenyl, $C_3$–$C_8$alkynyl, $C_3$–$C_6$cycloalkyl, $C_1$–$C_8$-halogenoalkyl, $C_3$–$C_8$halogenoalkenyl, cyano-$C_1$–$C_4$alkyl, $C_1$–$C_4$alkoxy-$C_1$–$C_4$alkyl, $C_3$–$C_6$alkenyloxy-$C_1$–$C_4$alkyl, (oxiranyl)—$CH_2$—, oxetanyl-, $C_1$–$C_4$alkylthio-$C_1$–$C_4$alkyl, phenyl, phenyl which is substituted once to three times by halogen, $C_1$–$C_4$alkyl or $C_1$–$C_4$halogenoalkyl, benzyl or benzyl which is substituted once to three times on the phenyl ring by halogen, $C_1$–$C_4$alkyl or $C_1$–$C_4$halogenoalkyl, phenyl-$C_2$–$C_6$alkyl, $C_1$–$C_6$alkyl-CO—$C_1$–$C_4$alkyl,

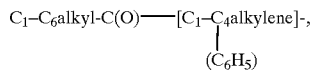

$R_{53}X_4C(O)$—$C_1$—$C_6$alkyl,

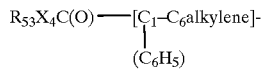

or $R_{53}X_4C(O)$—$C_3$–$C_6$cycloalkyl;

$X_4$ is oxygen, sulfur,

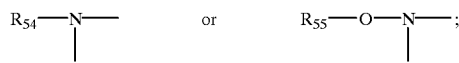

$R_{53}$ is hydrogen, $C_1$–$C_8$alkyl, $C_3$–$C_8$alkenyl, $C_3$–$C_8$alkynyl, $C_3$–$C_6$cycloalkyl, $C_1$–$C_8$-halogenoalkyl, $C_3$–$C_8$halogenoalkenyl, cyano-$C_1$–$C_4$alkyl, $C_1$–$C_4$alkoxy-$C_1$–$C_4$alkyl, $C_3$–$C_6$-alkenyloxy-$C_1$–$C_4$alkyl, (oxiranyl)—$CH_2$—, oxetanyl-, $C_1$–$C_4$alkylthio-$C_1$–$C_4$alkyl, phenyl, phenyl which is substituted once to three times by halogen, $C_1$–$C_4$alkyl or $C_1$–$C_4$halogenoalkyl, benzyl, benzyl which is substituted once to three times on the phenyl ring by halogen, $C_1$–$C_4$alkyl or $C_1$–$C_4$halogenoalkyl, or phenyl-$C_2$–$C_6$alkyl;

$R_{51}$, $R_{52}$, $R_{54}$ and $R_{55}$ independently of one another are hydrogen, $C_1$–$C_8$alkyl, $C_3$–$C_8$alkenyl, $C_3$–$C_8$alkynyl, $C_1$–$C_8$halogenoalkyl or benzyl; or $R_{13}$ is $B_1$-$C_1$–$C_8$alkyl, $B_1$-$C_2$–$C_8$alkenyl, $B_1$-$C_2$–$C_8$alkynyl, $B_1$-$C_1$–$C_8$halogenoalkyl, $B_1$-$C_2$–$C_8$halogenoalkenyl, $B_1$-$C_1$–$C_4$alkoxy-$C_1$–$C_4$alkyl, $B_1$-$C_1$–$C_4$alkylthio-$C_1$–$C_4$alkyl or $B_1$-$C_3$–$C_6$cycloalkyl;

$B_1$ is hydrogen, cyano, hydroxyl, $C_1$–$C_8$alkoxy, $C_3$–$C_8$alkenyloxy, $R_{60}X_5C(O)$—, $C_1$–$C_4$-alkylcarbonyl or $C_1$–$C_4$halogenoalkylcarbonyl;

$X_5$ has the meaning of $X_4$;

$R_{60}$ has the meaning of $R_{53}$; or $R_{13}$ is $B_2$-$C(R_{70})$═CH—;

$B_2$ is nitro, cyano or $R_{71}X_6C(O)$—;

$R_{70}$ is cyano or $R_{72}X_7C(O)$—;

$X_6$ and $X_7$ have the meaning of $X_4$; and $R_{71}$ and $R_{72}$ have the meaning of $R_{53}$, or a pyrazole N-oxide, agrochemically tolerated salt or stereoisomer of this compound of the formula I.

2. A compound of the formula I according to claim 1, in which $R_3$ is hydrogen, $C_1$–$C_4$alkyl, $C_1$–$C_4$halogenoalkyl, $C_2$–Cralkenyl, $C_2$–$C_6$halogenoalkenyl, $C_2$–$C_6$alkynyl, halogen, cyano, $NH_2C(S)$—, nitro or $R_{18}R_{19}N$—.

3. A compound of the formula I according to claim 1, which has the formula Ia

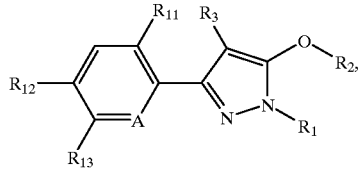

in which $R_1$, $R_2$, $R_3$, $R_{11}$, and $R_{13}$ are as defined in claim 1; and $R_{12}$ is hydrogen, halogen, $C_1$–$C_4$alkyl, $C_2$–$C_4$alkenyl, $C_2$–$C_4$alkynyl, $C_1$–$C_4$halogenoalkyl, $C_2$–$C_4$-halogenoalkenyl, nitro, amino, CHO, $C_1$–$C_4$halogenoalkoxy, cyano, $C_3$–$C_6$cycloalkyl, phenoxy, phenoxy which is substituted once to three times by halogen, $C_1$–$C_4$alkyl or $C_1$–$C_4$-halogenoalkyl, benzyloxy or benzyloxy which is substituted once to three times on the phenyl ring by halogen, $C_1$–$C_4$alkyl or $C_1$–$C_4$halogenoalkyl.

4. A compound according to claim 3, in which $R_3$ is methyl, $C_1$–$C_4$halogenoalkyl, chlorine or bromine.

5. A compound according to claim 4, in which $R_1$ is $C_1$–$C_4$alkyl; $R_2$ is $C_1$- or $C_2$halogenoalkyl; $R_3$ is chlorine or bromine; A is ═N—; $R_{11}$ is fluorine, chlorine or bromine; $R_{12}$ is halogen; and $R_{13}$ is hydrogen.

6. A compound according to claim 5, in which $R_1$ is methyl or ethyl; $R_2$ is halogenomethyl; $R_3$ is chlorine; $R_1$, is fluorine; and $R_{12}$ is chlorine.

7. A compound according to claim 6, in which $R_1$ is methyl; and $R_2$ is difluoromethyl.

8. A process for the preparation of a compound of the formula I

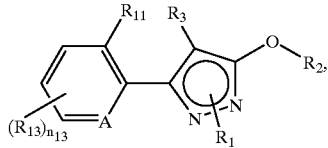

in which $R_1$, $R_2$, $R_1$, $R_{13}$, A and $n_{13}$ are as defined in claim 1, and $R_3$ is hydrogen, halogen, $C_1$–$C_4$alkyl or $C_1$–$C_4$halogenoalkyl, which comprises reacting a compound of the formula X

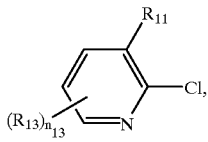

in which $R_{11}$, $R_{13}$ and $n_{13}$ are as defined, in an alcohol of the formula XV $R_8$—OH        (XV), in which $R_8$ is $C_1$–$C_4$alkyl, in the presence of a suitable palladium or nickel catalyst and a base under an increased pressure of carbon monoxide to give the compound of the formula XI

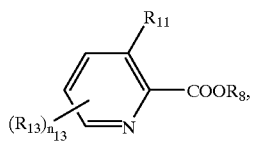
(XI)

in which $R_8$, $R_{11}$, $R_{13}$ and $n_{13}$ are as defined, hydrolysing this under acid or basic conditions to give the corresponding carboxylic acid of the formula XII

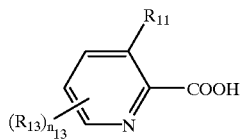
(XII)

and converting this with a carboxylic acid halogenating reagent into the corresponding carboxylic acid halide of the formula XIII

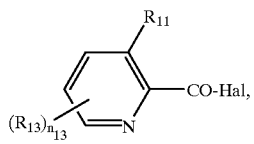
(XIII)

in which $R_{11}$, $R_{13}$ and $n_{13}$ are as defined; and Hal is halogen, and reacting this in a solvent in the presence of an alkaline earth metal salt and a base with the malonic acid monoester salt of the formula XVI

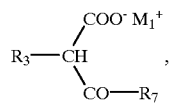
(XVI)

in which $R_3$ is hydrogen, $C_1$–$C_4$alkyl or $C_1$–$C_4$halogenoalkyl; $M_1^+$ is an alkali metal ion and $R_7$ is $C_1$–$C_4$alkoxy, to give the keto ester of the formula III

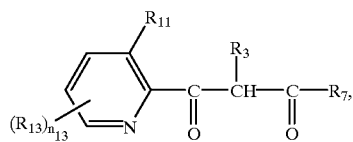
(III)

in which $R_3$, $R_7$, $R_{11}$, $R_{13}$ and $n_{13}$ are as defined, and cyclizing this in a solvent with the compound of the formula XIV $$NH_2NH\text{—}R_1 \quad (XIV),$$

in which $R_1$ is as defined in claim 1, to give the compound of the formula Ic

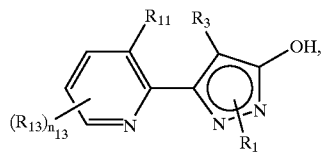
(Ic)

in which $R_1$, $R_3$, $R_{11}$, $R_{13}$ and $n_{13}$ are as defined, and then, functionalizing the hydroxyl group, according to the definition of $R_2$, if appropriate halogenating the pyrazole ring ($R_3$ halogen), or oxidizing the compound to the corresponding pyridine N-oxide.

9. A herbicidal and plant growth-inhibiting composition which comprises a herbicidally active content of a compound of the formula I according to claim 1 and an inert carrier.

10. A composition according to claim 9, which comprises between 0.1% and 95% of an active substance of the formula I.

11. A method of controlling undesirable plant growth, which comprises applying an active substance of the formula I according to claim 1, or a composition comprising this active substance, to the crops of useful plants or their environment in a herbicidally active amount.

12. A method according to claim 11, wherein an amount of active substance of between 0.001 and 4 kg per hectare is applied.

13. A method of inhibiting plant growth, which comprises applying an active substance of the formula I, according to claim 1 or a composition comprising this active substance, to the plants or their environment in an active amount.

14. A method according to claim 13, wherein the crops of useful plants are cereals, maize, rice, cotton, soya, oilseed rape, sorghum, sugarcane, sugarbeet, sunflowers, vegetables, plantations and fodder plants.

* * * * *